(12) United States Patent
Poreddy et al.

(10) Patent No.: US 8,697,033 B2
(45) Date of Patent: Apr. 15, 2014

(54) MODIFIED PYRAZINE DERIVATIVES AND USES THEREOF

(75) Inventors: Amruta Poreddy, St. Louis, MO (US); William L. Neumann, St. Louis, MO (US)

(73) Assignee: Medibeacon, LLC, St. Louis, MO (US)

( * ) Notice: Subject to any disclaimer, the term of this patent is extended or adjusted under 35 U.S.C. 154(b) by 169 days.

(21) Appl. No.: 13/140,107

(22) PCT Filed: Dec. 17, 2009

(86) PCT No.: PCT/US2009/068463
§ 371 (c)(1),
(2), (4) Date: Jun. 16, 2011

(87) PCT Pub. No.: WO2010/078028
PCT Pub. Date: Jul. 8, 2010

(65) Prior Publication Data
US 2011/0250140 A1  Oct. 13, 2011

Related U.S. Application Data

(60) Provisional application No. 61/138,149, filed on Dec. 17, 2008, provisional application No. 61/139,911, filed on Dec. 22, 2008.

(51) Int. Cl.
*A61K 49/00* (2006.01)
*A61P 13/12* (2006.01)
*A61P 13/10* (2006.01)
*C07D 241/20* (2006.01)
*A61K 31/4965* (2006.01)

(52) U.S. Cl.
USPC ............ 424/9.1; 514/255.06; 544/407

(58) Field of Classification Search
USPC ............ 424/9.1; 514/255.06; 544/407
See application file for complete search history.

(56) References Cited

U.S. PATENT DOCUMENTS

| | | | |
|---|---|---|---|
| 3,814,757 | A | 6/1974 | Donald |
| 3,948,895 | A | 4/1976 | Donald |
| 6,440,389 | B1 | 8/2002 | Rabito |
| 8,115,000 | B2 * | 2/2012 | Rajagopalan et al. ........ 544/407 |
| 2008/0312539 | A1 | 12/2008 | Dorshow et al. |
| 2011/0250139 | A1 * | 10/2011 | Poreddy et al. ............... 424/9.1 |

FOREIGN PATENT DOCUMENTS

| WO | 2007149479 | 12/2007 | |
|---|---|---|---|
| WO | WO 2007/149479 | * 12/2007 | ............ C07D 241/26 |

OTHER PUBLICATIONS

Patani, et al., Chem. Rev., 1996, 96, 3147-3176.*
Nally et al. (2002) "Acute renal failure in hospitalized patients." Cleveland Clinic Journal of Medicine, 69(7), 569-574.
Rabito et al. (1993) "Renal function in patients at risk with contrast material-induced acute renal failure: Noninvasive real-time monitoring" Radiology, 186, 851-854.
Tilney et al. (1983) "Acute renal failure in surgical patients: Causes, clinical patterns, and care" Surgical Clinics of North America, 63, 357-377.
VanZee et al. (1978) "Renal injury associated with intravenous pyelography in non-diabetic and diabetic patients" Annals of Internal Medicine, 89, 51-54.
Lundqvist et al. (1996) "Iohexol clearance for renal function measurement in gynecologic cancer patients" Acta Radiologica, 37, 582-586.
Guesry et al. (1975) "Measurement of glomerolar filtration rate by fluorescent excitation of non-radioactive meglumine iothalamate", Clinical Nephrology, 3, 134-138.
Baker et al. (1980) "Epidemiology of Trauma Deaths", American Journal of Surgery, 140, 144-150.
Lobenhoffer et al. (1995) "Treatment Results of Patients with Multiple Traumas: An Analysis of 3406 Cases Treated Between 1972 and 1991 at a German Level I Trauma Center" Journal of Trauma, 38, 70-77.
Coalson et al. (1986) Pathology of Sepsis, Septic Shock, and Multiple Organ Failure. In New Horizons: Multiple Organ Failure, D.J. Bihari and F.B. Cerra (Eds.) Society of Critical Care Medicine, Fullerton, CA, pp. 27-59.
Cerra et al. (1989) Multiple Organ Failure Syndrome. In New Horizons: Multiple Organ Failure, D.J. Bihari and F.B. Cerra, (Eds). Society of Critical Care Medicine, Fullerton, CA, pp. 1-24.
Muller-Suur et al. (1989) "Glomerular filtration and tubular secretion of MAG3 rat kidney" Journal of Nuclear Medicine, 30, 1986-1991.
Doolan et al. (1962) "A clinical appraisal of the plasma concentration and endogeneous clearance of creatinine" American Journal of Medicine, 32, 65-79.

(Continued)

*Primary Examiner* — Joseph Kosack
(74) *Attorney, Agent, or Firm* — Dennis A. Bennett; Gale W. Starkey

(57) ABSTRACT

In some embodiments, the invention provides modified pyrazine derivatives containing a central pyrazine ring with two secondary amine groups attached directly to the central pyrazine ring and two amino carbonyl groups attached directly to the central pyrazine ring. The secondary amine groups are terminated by alkyl groups containing from 1 to 6 carbons. The amino carbonyl groups can be terminated by a wide range of substituents including, but not limited to, alkyl and alkylene groups, polyether groups, including poly(ethylene glycol) groups, secondary and tertiary amine groups, polyhydroxylated alkyl groups, amino carbonyl groups, amino thioketone groups, and combinations thereof. In some embodiments, the invention provides modified pyrazine derivatives useful as optical agents in a wide variety of biomedical imaging procedures, including diagnostic and imaging procedures. In an embodiment, for example, modified pyrazine derivatives are provided which are useful in monitoring organ and system functioning, for example in monitoring renal system functioning.

20 Claims, 9 Drawing Sheets

(56) References Cited

OTHER PUBLICATIONS

Henry's Clinical Diagnosis and Management by Laboratory Methods, 21st edition, Ch. 14, W.B. Saunders, Philidelphia, PA, 2006, pp. 147-169.
Roch-Ramel et al. (1992) "Renal excretion and tubular transport of organic anions and cations" Handbook of Physiology, Section 8, Neurological Physiology, vol. II, E.E. Windhager, Editor, pp. 2189-2262, Oxford University Press: New York.
Nosco et al. (1999) "Chemistry of technetium radiopharmaceuticals 1: Chemistry behind the development of technetium-99m compounds to determine kindey function" Coordination Chemistry Reviews 184, 91-123.
Choyke et al. (1992) "Hydrated clearance of gadolinium-DTPA as a measurement of glomerular filtration rate" Kidney International, 41, 1595-1598.
Lewis et al. (1989) "Comparative evaluation of urographic contrast media, insulin, and 99mTc-DTPA clearance methods for determination of glomerular filtration rate in clinical transplantation" Transplantation, 48, 790-796.
Tauxe et al. (1985) Tubular Function. In Nuclear Medicine in Clinical Urology and Nephrology, W.N. Tauxe and E.V. Dubovsky, Editors, pp. 77-105, Appleton Century Crofts: East Norwalk.
Fritzberg et al (1986) "Mercaptoacetylglycylglycyglycine" Journal of Nuclear Medicine, 27, 111-120.
Ekanoyan et al. (2002) "In Clinical Practice Guidelines for Chronic Kidney Disease: Evaluation, Classification, and Stratification (K/DOQI)" National Kidney Foundation: Washington DC, pp. 1-22.
Ozaki et al. (2000) "Sensitization of europium (III) luminescence by DTPA derivatives" Chemistry Letters, 312-313.
Rajagopalan et al. (2000) "Polyionic fluorescent bioconjugates as composition agents for continuous monitoring of renal function" In Molecular Imaging: Reporters, Dyes, Markers, and Instrumetnation, A. Priezzhev, T. Asakura, and J. D. Briers, Editors, Proceedings of SPIE, 3924, 1-7.
Dorshow et al. (1998) "Noninvasive renal function assessment by fluorescence detection. In Biomedical Optical Spectroscopy and Diagnostics, Trends in Optics and Photonics Series 22", E.M. Sevick-Muraca, J.A. Izatt, and M.N. Ediger, Editors, Optical Society of America, Washington DC pp. 54-56.
Shirai et al. (1998) "Synthesis and fluorescent properties of 2,5-diamino-3,6-dicyanopyrazine dyes. Dyes and Pigments" 39(1), 49-68.
Kim et al. (1998) "Self-assembling of aminopyrazine fluorescent dyes their solid state spectra" Dyes and Pigments, 39 (4), 341-357.
Barlin et al. (1982) "The pyrazines, In Chemistry of Heterocyclic Compounds" A. Weissberger and E.C. Taylor, Eds John Wiley & Sons, New York, pp. 247-297.
Muller et al. (1993) "Medical Optical Tomography" SPIE vol. IS11, pp. 147-165, pp. 263-282, pp. 397-424, and pp. 485-512.
Dorshow et al. (1998) "Non-Invasive Fluorescence Detection of Hepatic and Renal Function" Journal of Biomedical Optics, 3(3), 340-345.
Dorshow et al. (1999) "Monitoring Physiological Function by Detection of Exogeneous Fluorescent Contrast Agents, In Optical Diagnostics of Biological Fluids IV" A. Priezzhevand, T. Asakura, Editors, Proceedings of SPIE, 3599, 2-8.
Stahl et al. (2002) Handbook of Pharmaceutical Salts: Properties, Selection, and Use, Wiley-VCH; Verlag Helvetica Chimica Acta, Zurich, pp. 161-189 and pp. 249-263.
Poreddy et al. (2009) "N-Alkylated aminopyrazines for use as hydrophilic optical agents" Proc. of SPIE vol. 7190 71900P-1-71900P-10.
Larsen et al. (2010) "Prodrugs: Design and Development" Textbook of Drug Design and Discovery; Ch.9, pp. 135-149.
Florence et al.(2009) "Tablet Dosage Forms", Modern Pharmaceutics vol. 1, Basic Principles and Systems, Ch. 13, pp. 481-497.
Bundgaard (1992) "Prodrugs as a means to improve the delivery of peptide drugs" Advanced Drug Delivery Reviews, vol. 8, pp. 1-38.
Bundgaard et al, (1988) "Glycolamide Esters as Biolabile Prodrugs of Carboxylic Acid Agents", Journal of Pharmaceutical Sciences, vol. 77, No. 4, p. 285.
J.G. Nairn, (1985), "Solutions, Emulsions, Suspension, and Extractives", Remington's Pharmaceutical Science, pp. 1492-1517.
Spiegel et al. (1963) "Use of Nonaqueous Solvents in Parenteral Products", Journal of Pharmaceutical Sciences, vol. 52, No. 10, pp. 917-927.
Braun et al (1992) "Liposome Production: Historic Aspects", The British Library, pp. 69-81; 91-117.
Nogrady (1988) "Medicinal Chemistry A Biochemical Approach", 2nd edition, pp. 467-472.

* cited by examiner

Creatinine
MW: 113 o-Iodohippurate
MW: 327

$^{99m}$Tc-DTPA
MW: 487

$^{99m}$Tc-MAG3
MW: 364

US 8,697,033 B2

MODIFIED PYRAZINE DERIVATIVES AND USES THEREOF

CROSS REFERENCE TO RELATED APPLICATIONS

This application is a national stage application of PCT/US2009/068463, filed Dec. 17, 2009, which claims the benefit of U.S. Provisional Application No. 61/139,911 filed Dec. 22, 2008 and U.S. Provisional Application No. 61/138,149 filed Dec. 17, 2008.

BACKGROUND

Various publications are referenced throughout this disclosure by Arabic numerals in brackets. A citation corresponding to each reference number is listed following the Examples.

Acute renal failure (ARF) is a common ailment in patients admitted to general medical-surgical hospitals. Approximately half of the patients who develop ARF die, and survivors face marked increases in morbidity and prolonged hospitalization [1]. Early diagnosis is generally believed to be important, because renal failure is often asymptomatic and typically requires careful tracking of renal function markers in the blood. Dynamic monitoring of patient renal function is desirable in order to reduce the risk of acute renal failure brought about by various clinical, physiological and pathological conditions [2-6]. Such dynamic monitoring might be particularly desirable in the case of critically ill or injured patients, because a large percentage of these patients tend to face risk of multiple organ failure (MOF) potentially resulting in death [7, 8]. MOF is a sequential failure of the lungs, liver and kidneys and is incited by one or more of acute lung injury (ALI), adult respiratory distress syndrome (ARDS), hypermetabolism, hypotension, persistent inflammatory focus and sepsis syndrome. Common histological features of hypotension and shock leading to MOF generally include tissue necrosis, vascular congestion, interstitial and cellular edema, hemorrhage and microthrombi. These changes generally affect the lungs, liver, kidneys, intestine, adrenal glands, brain, and pancreas in descending order of frequency [9]. The transition from early stages of trauma to clinical MOF generally corresponds with a particular degree of liver and renal failure as well as a change in mortality risk from about 30% up to about 50% [10].

Traditionally, renal function of a patient has been determined using crude measurements of the patient's urine output and plasma creatinine levels [11-13]. These values can be misleading because such values are affected by age, state of hydration, renal perfusion, muscle mass, dietary intake, and many other clinical and anthropometric variables. In addition, a single value obtained several hours after sampling can be difficult to correlate with other physiologic events such as blood pressure, cardiac output, state of hydration, and other specific clinical events (e.g., hemorrhage, bacteremia, ventilator settings and others).

With regard to conventional renal monitoring procedures, an approximation of a patient's glomerular filtration rate (GFR) can be made via a 24 hour urine collection procedure that (as the name suggests) typically requires about 24 hours for urine collection, several more hours for analysis, and a meticulous bedside collection technique. Unfortunately, the undesirably late timing and significant duration of this conventional procedure can reduce the likelihood of effectively treating the patient and/or saving the kidney(s). As a further drawback to this type of procedure, repeat data tends to be equally as cumbersome to obtain as the originally acquired data.

Occasionally, changes in serum creatinine of a patient are adjusted based on measurement values such as the patient's urinary electrolytes and osmolality as well as derived calculations such as "renal failure index" and/or "fractional excretion of sodium." Such adjustments of serum creatinine undesirably tend to require contemporaneous collection of additional samples of serum and urine and, after some delay, further calculations. Frequently, dosing of medication is adjusted for renal function and thus can be equally as inaccurate, equally delayed, and as difficult to reassess as the measurement values and calculations upon which the dosing is based. Finally, clinical decisions in the critically ill population are often equally as important in their timing as they are in their accuracy.

It is known that hydrophilic, anionic substances are generally capable of being excreted by the kidneys [14]. Renal clearance typically occurs via two pathways: glomerular filtration and tubular secretion. Tubular secretion can be characterized as an active transport process, and hence, the substances clearing via this pathway typically exhibit specific properties with respect to size, charge and lipophilicity.

Most of the substances that pass through the kidneys are filtered through the glomerulus (a small intertwined group of capillaries in the malpighian body of the kidney). Examples of exogenous substances capable of clearing the kidney via glomerular filtration (hereinafter referred to as "GFR agents") are shown in FIG. 1 and include creatinine, o-iodohippuran, and $^{99m}$Tc-DTPA [15-17]. Examples of exogenous substances that are capable of undergoing renal clearance via tubular secretion include $^{99m}$Tc-MAG3 and other substances known in the art [15, 18, 19]. $^{99m}$Tc-MAG3 is also widely used to assess renal function though gamma scintigraphy as well as through renal blood flow measurement. As one drawback to the substances illustrated in FIG. 1, o-iodohippuran, $^{99m}$Tc-DTPA and $^{99m}$Tc-MAG$_3$ include radioisotopes to enable the same to be detected. Even if non-radioactive analogs (e.g., such as an analog of o-iodohippuran) or other non-radioactive substances were to be used for renal function monitoring, such monitoring would typically require the use of undesirable ultraviolet radiation for excitation of those substances.

SUMMARY

In some embodiments, the invention provides modified pyrazine derivatives containing a central pyrazine ring with two secondary amine groups attached directly to the central pyrazine ring and two amino carbonyl groups attached directly to the central pyrazine ring. The secondary amine groups are terminated by alkyl groups containing from 1 to 6 carbons. The amino carbonyl groups can be terminated by a wide range of substituents including, but not limited to, alkyl and alkylene groups, polyether groups, including polyethylene glycol) groups, secondary and tertiary amine groups, polyhydroxylated alkyl groups, amino carbonyl groups, amino thioketone groups, and combinations thereof.

In some embodiments, the invention provides modified pyrazine derivatives useful as optical agents in a wide variety of biomedical procedures, including diagnostic and imaging procedures. In an embodiment, for example, modified pyrazine derivatives are provided which are useful in monitoring organ and system functioning, for example in monitoring renal system functioning. In some embodiments, the optical and pharmacokinetic properties of compounds of the invention can be adjusted by selection of suitable modifications to substituents of the central pyrazine ring. In an aspect of this embodiment, for example, the absorption and emission spectra of compounds of the invention can be tuned by selection of suitable modifications to substituents of the central pyrazine ring. In an embodiment, for example, an absorption maxima of a compound of the invention is shifted a selected number of nanometers (e.g., 10-50 nm) toward the red region of the electromagnetic spectrum by selection of the composition of substituents of the central pyrazine group. In a further aspect of this embodiment, the clearance rate of compounds of the invention can be tuned by selection of suitable modifications to substituents of the central pyrazine ring. In an embodiment, for example, the absorption and emission spectra of compounds of the invention can be tuned by selection of suitable modifications to substituents of the central pyrazine ring to enable enhanced tissue penetration of exciting electromagnetic radiation.

In an embodiment, the invention provides compounds being of formula (FX1):

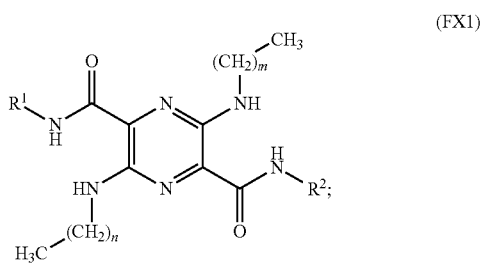

(FX1)

wherein: each of $R^1$ and $R^2$ is —$(CH_2)_a(CH_2CH_2O)_bR^3$, —$(CH_2CH_2O)_bR^3$, —$(CH_2)_c(CH_2CH_2O)_d(CH_2)_eNR^4CONR^5(CH_2)_f(CH_2CH_2O)_bR^6$, —$(CH_2)_c(CH_2CH_2O)_d(CH_2)_eNR^4CSNR^5(CH_2)_f(CH_2CH_2O)_bR^6$, —$(CH_2)_c(CH_2CH_2O)_d(CH_2)_eCONR^4(CH_2)_f(CH_2CH_2O)_bR^6$, —$(CH_2)_c(CH_2CH_2O)_d(CH_2)_eNR^4SO_2(CH_2)_f(CH_2CH_2O)_bR^6$, —$(CH_2)_c(CH_2CH_2O)_d(CH_2)_eSO_2NR^4(CH_2)_f(CH_2CH_2O)_bR^6$, —$(CH_2)_c(CH_2CH_2O)_d(CH_2)_eNR^4CO(CH_2)_f(CH_2CH_2O)_bR^6$, —$(CH_2)_c(CH_2CH_2O)_d(CH_2)_eNR^4CO_2(CH_2)_f(CH_2CH_2O)_bR^6$, —$(CH_2)_c(CH_2CH_2O)_d(CH_2)_eOC(O)NR^4(CH_2)_f(CH_2CH_2O)_bR^6$, or —$(CH_2)_aY^1$; each $Y^1$ is independently —$OR^3$, —$(CHOH)_cR^7$, —$NR^8R^9$, —$CONR^8R^9$, —$NHCO(CH_2)_a(CH_2CH_2O)_bR^6$ or —$NHCO(CHOH)_cR^7$; each of $R^3$, $R^4$, $R^5$, $R^6$ and $R^7$ is independently —H or $C_1$-$C_6$ alkyl; each of $R^8$ and $R^9$ is independently —H, $C_1$-$C_3$ alkyl, —$(CH_2)_a(CHOH)_cR^7$ or —$(CH_2)_a(CH_2CH_2O)_bR^6$; each of a, c, e and f is independently an integer from 0 to 10; each b is independently an integer from 1 to 120; each d is independently an integer from 0 to 120; and each of m and n is independently an integer from 0 to 5.

In one aspect, described herein are compounds of Formula (FX1) and their pharmaceutically acceptable salts and esters. In some embodiments, each of $R^1$ and $R^2$ is —$(CH_2)_a(CHOH)_cR^7$. In other embodiments, each of $R^1$ and $R^2$ is —$(CH_2)_aNR^8R^9$. In still other embodiments, each of $R^1$ and $R^2$ is —$(CH_2)_c(CH_2CH_2O)_d(CH_2)_eNR^4CSNR^5(CH_2)_f(CH_2CH_2O)_bR^6$. In other embodiments, each of $R^1$ and $R^2$ is —$(CH_2)_aY^1$. In still other embodiments, each of $R^1$ and $R^2$ is —$(CH_2)_aCONR^8R^9$. In still other embodiments, each of $R^1$ and $R^2$ is —$(CH_2)_c(CH_2CH_2O)_d(CH_2)_eOC(O)NR^4(CH_2)_f(CH_2CH_2O)_bR^6$. In still other embodiments, each of $R^1$ and $R^2$ is —$(CH_2CH_2O)_bR^3$. In still other embodiments, each of $R^1$ and $R^2$ is —$(CH_2)_c(CH_2CH_2O)_d(CH_2)_eNR^4SO_2(CH_2)_f(CH_2CH_2O)_bR^6$.

Still referring to compounds of Formula (FX1), in some embodiments, $R^3$, $R^4$, $R^5$, $R^6$ and $R^7$ are —H or $C_1$-$C_6$ alkyl, optionally $C_1$-$C_3$ alkyl or optionally —H. For example, in some embodiments, each occurrence of $R^5$ can independently be $C_1$-$C_6$ alkyl (e.g., each occurrence of $R^5$ is $C_1$ alkyl). In some embodiments, each of $R^3$, $R^4$, $R^5$, $R^6$ and $R^7$ is —H. In other embodiments, each of $R^3$, $R^4$, $R^5$, $R^6$ and $R^7$ is independently $C_1$-$C_6$ alkyl (e.g., each of $R^3$, $R^4$, $R^5$, $R^6$ and $R^7$ is $C_1$ alkyl).

The variable m independently varies from 0 to 5, inclusive. For instance, in some embodiments, m can be 1, 2, or 3 (e.g., m can be 3 in some embodiments). Likewise, n independently varies from 0 to 5, inclusive. For instance, in some embodiments, n can be 3 or 4 (e.g., n can be 3 in some embodiments). One of the benefits of m and n independently varying from 0 to 5 is that the pyrazine derivative can be "tuned" to absorb or luminesce at a desired wavelength or range of wavelengths. In this regard, some pyrazine derivatives having both m and n equal to 3 absorb and/or luminesce at respective electromagnetic radiation wavelengths that are greater than (e.g., about 10-15 nm greater than) that of a generally similar pyrazine derivative where both m and n are equal to 2. A similar shift in absorption and/or luminescent wavelengths of some compounds is observed moving from 3 to 4, from 4 to 5, and/or from 5 to 6. Accordingly, pyrazine derivatives described herein can be designed to absorb and/or luminesce at electromagnetic radiation wavelengths that can penetrate tissues better than that of lower electromagnetic radiation wavelengths.

Still referring to compounds of Formula (FX1), each occurrence of b independently varies from 1 to 120, inclusive. For instance, in some embodiments, each b independently varies from 2 to 50, inclusive. In other embodiments, each b independently varies from 2 to 24, inclusive. In still other embodiments, each b independently varies from 12 to 24, inclusive. In an embodiment, the invention provides a compound having formula (FX1), wherein each b is independently an integer greater than 3, preferably an integer greater than 5 for some applications, and preferably an integer greater than 10 for some applications. Still referring to compounds of Formula (FX1), each occurrence of d independently varies from 0 to 120, inclusive. For instance, in some embodiments, each d independently varies from 2 to 50, inclusive. In other embodiments, each d independently varies from 0 to 23, inclusive. In other embodiments, each d is independently 0.

With regard to the various possibilities for $R^1$ and $R^2$ in Formula (FX1), each occurrence of a, c, e, and f independently vary from 0 to 10, inclusive. For instance, in some embodiments, each occurrence of a, c, e, and f independently varies from 0 to 6, inclusive. In embodiments, each of a, c, e, and f is independently an integer from 0 to 3. For example, each occurrence of a is 3 in some embodiments.

In an embodiment, the invention provides compounds having formula (FX2):

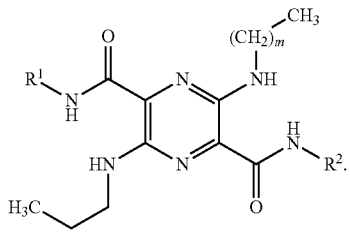
(FX2)

In an embodiment, the invention provides compounds having formula (FX3):

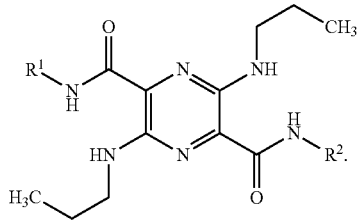
(FX3)

In an embodiment, the invention provides compounds having formula (FX4):

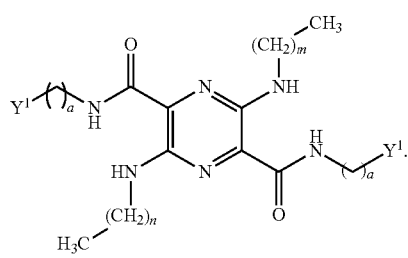
(FX4)

In an embodiment, the invention provides compounds having formula (FX5):

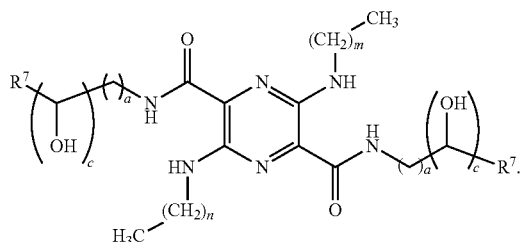
(FX5)

In an embodiment, the invention provides compounds having formula (FX6) or (FX7):

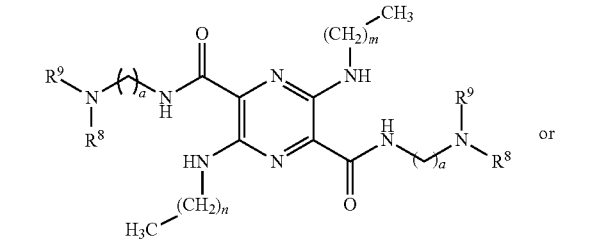
(FX6)

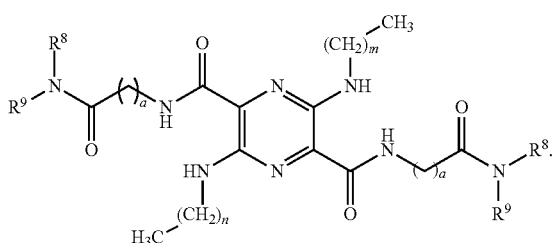
(FX7)

In an embodiment, the invention provides compounds having formula (FX6) or (FX7) wherein each a independently varies from 0 to 3, inclusive (e.g., each a is 2). In a further aspect of this embodiment, the invention provides compounds having formula (FX6) or (FX7) wherein each a is 1.

In an embodiment, the invention provides compounds having formula (FX8) or (FX9):

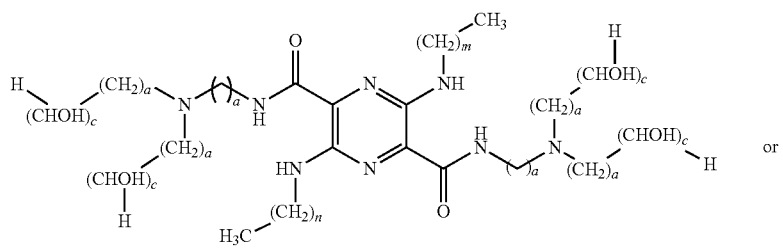
(FX8)

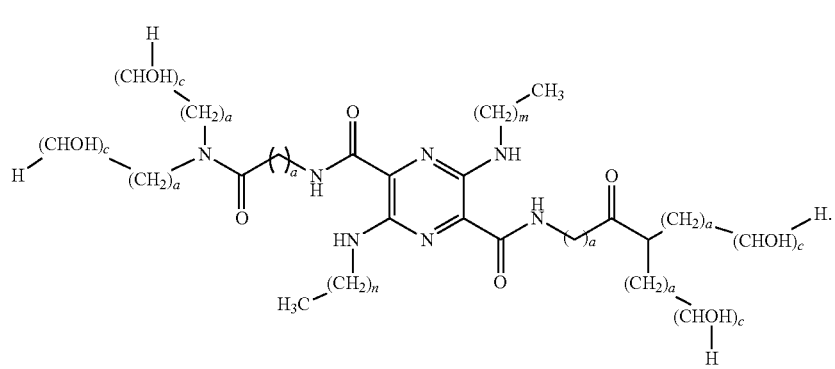
(FX9)

In an embodiment, the invention provides compounds having formula (FX8) or (FX9) wherein each a independently varies from 0 to 3, inclusive (e.g., each a is 2). In a further aspect of this embodiment, the invention provides compounds having formula (FX8) or (FX9) wherein each a is 1. In a further aspect of this embodiment, the invention provides compounds having formula (FX8) or (FX9) wherein each c independently varies from 1 to 10, inclusive (e.g., each c is 2).

In an embodiment, the invention provides compounds having formula (FX10) or (FX11):

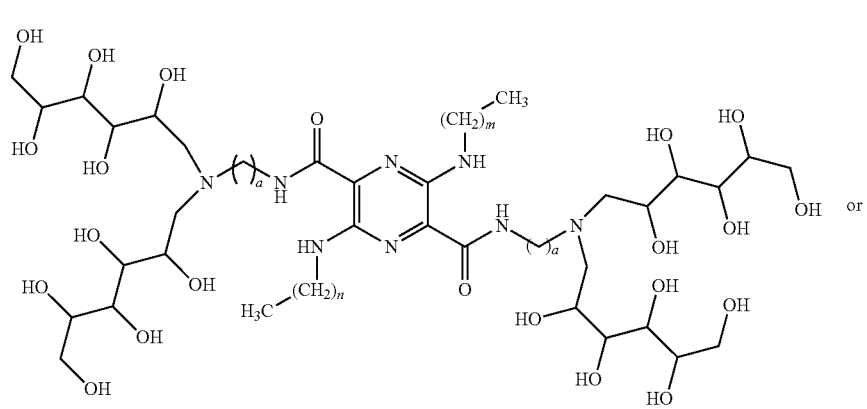
(FX10)

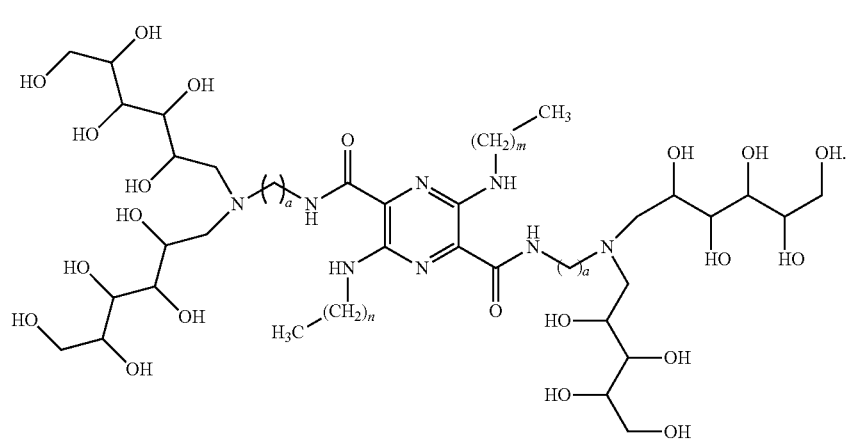
(FX11)

In an embodiment, the invention provides compounds having formula (FX12):

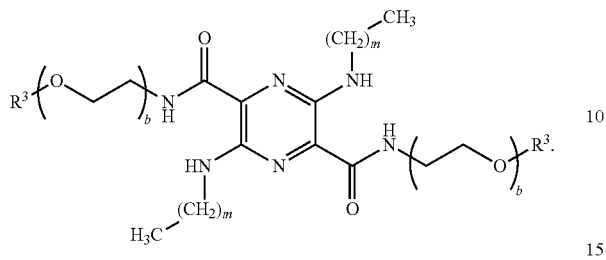

(FX12)

In an embodiment, the invention provides compounds having formula (FX13):

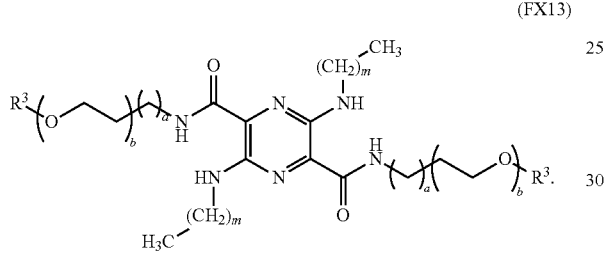

(FX13)

In an embodiment, the invention provides compounds wherein each $R^3$ is independently $C_1$-$C_6$ alkyl. In an embodiment, the invention provides compounds wherein each $R^3$ is independently $C_1$-$C_3$ alkyl. In an embodiment, the invention provides compounds wherein each $R^3$ is $C_1$ alkyl. In an embodiment, the invention provides compounds wherein each $R^3$ is —H. In an embodiment, the invention provides compounds wherein each a is independently an integer from 0 to 10 (e.g. each a is 4). In an embodiment, the invention provides compounds wherein each a is independently an integer from 0 to 6 (e.g., each a is 3).

In an embodiment, the invention provides compounds having formula (FX14):

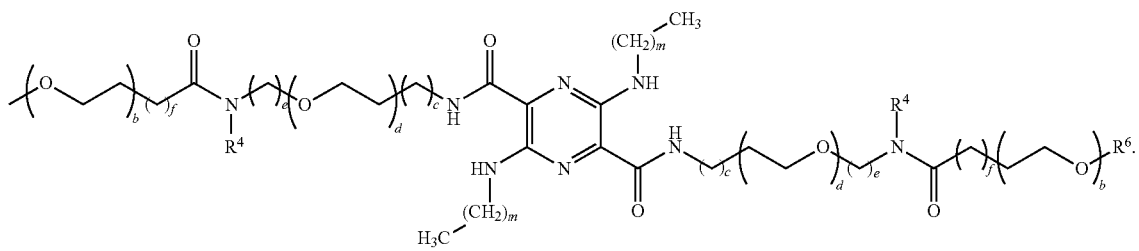

(FX14)

In an embodiment, the invention provides compounds having formula (FX15):

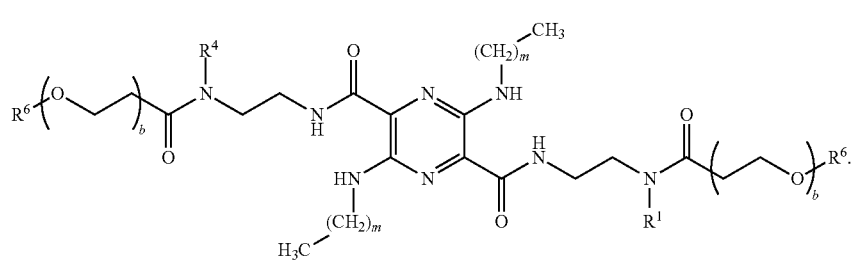

(FX15)

In an embodiment, the invention provides compounds wherein each $R^4$ is independently —H. In an embodiment, the invention provides compounds wherein each $R^4$ is independently $C_1$-$C_6$ alkyl. In an embodiment, the invention provides compounds wherein each $R^4$ is independently $C_1$-$C_3$ alkyl. In an embodiment, the invention provides compounds wherein each $R^4$ is independently $C_1$ alkyl.

In an embodiment, the invention provides compounds wherein each $R^6$ is independently —H. In an embodiment, the invention provides compounds wherein each $R^6$ is independently $C_1$-$C_6$ alkyl. In an embodiment, the invention provides compounds wherein each $R^6$ is independently $C_1$-$C_3$ alkyl. In an embodiment, the invention provides compounds wherein each $R^6$ is independently $C_1$ alkyl.

In an embodiment, the invention provides compounds wherein each b is independently an integer from 2 to 24 (e.g., each b is 12). In an embodiment, the invention provides compounds wherein each b is independently an integer from 2 to 50 (e.g., each b is 24). In an embodiment, the invention provides compounds wherein each b is independently an integer from 12 to 24 (e.g., each b is 18). In an embodiment, the invention provides compounds wherein each b is independently an integer greater than 3, preferably an integer greater than 5 for some applications, and preferably an integer greater than 10 for some applications.

In an embodiment, the invention provides compounds wherein each a is independently an integer from 0 to 10 (e.g., each a is 3). In an embodiment, the invention provides compounds wherein each a is independently an integer from 0 to 6 (e.g., each a is 4). In an embodiment, the invention provides compounds wherein each a is independently an integer from 0 to 2 (e.g., each a is 2). In an embodiment, the invention provides compounds wherein each a is 0.

In an embodiment, the invention provides compounds wherein each c is independently an integer from 0 to 10 (e.g., each c is 3). In an embodiment, the invention provides compounds wherein each c is independently an integer from 0 to 6 (e.g., each c is 4). In an embodiment, the invention provides compounds wherein each c is independently an integer from 0 to 2 (e.g., each c is 2). In an embodiment, the invention provides compounds wherein each c is 0.

In an embodiment, the invention provides compounds wherein each d is independently an integer from 0 to 24 (e.g., each d is 12). In an embodiment, the invention provides compounds wherein each d is 0.

In an embodiment, the invention provides compounds wherein each e is independently an integer from 1 to 6 (e.g., each e is 1). In an embodiment, the invention provides compounds wherein each e is independently an integer from 2 to 4 (e.g., each e is 3). In an embodiment, the invention provides compounds wherein each e is 2.

In an embodiment, the invention provides compounds wherein each f is independently an integer from 0 to 6 (e.g., each f is 1). In an embodiment, the invention provides compounds wherein each f is independently an integer from 0 to 4 (e.g., each f is 2). In an embodiment, the invention provides compounds wherein each f is 0.

In an aspect of the invention, m and n are the same integer. In an aspect of the invention, each b appearing in a formula is the same integer. In an aspect of the invention, each c appearing in a formula is the same integer. In an aspect of the invention, each a appearing in a —$(CH_2)_aY^1$ group is the same integer. In an aspect of the invention, $R^1$ and $R^2$ are the same. In an aspect of the invention, the groups that are para to each other on the pyrazine ring are the same. In an aspect of the invention, m and n are the same. In an aspect of the invention, compounds of the invention are aminopyrazine compounds having one or more poly(ethylene glycol) (PEG) groups. In an aspect of the invention, PEG groups add hydrophilic character to the pyrazine derivatives. As used herein, PEG groups are generally depicted by the formula —$(CH_2CH_2O)_b$— and are also known as repeating ethylene oxide groups.

In an embodiment, compounds of the invention comprise one or more branched or straight chain alkyl groups containing two or more hydroxyl groups. These groups can be referred to as "polyhydroxylated alkyl" or "polyhydroxyalkyl" groups in an embodiment. In an embodiment, the polyhydroxylated alkyl group has from three to six carbon atoms. In an embodiment, the polyhydroxylated alkyl group includes two or more —(CHOH) groups along with one or more methylene groups, depicted by the formula: —$(CHR^{10})_rR^{11}$ where $R^{10}$ and $R^{11}$ are each independently H, $C_1$-$C_3$ alkyl or —OH, and r is an integer from 1 to 10. In an embodiment, the hydroxyl groups can be adjacent to each other or separated by one or more methylene groups. In an embodiment, the polyhydroxylated alkyl group refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

In an aspect of the invention, there is a one to six carbon alkylene group attached to the amino groups directly attached to the pyrazine core.

In an embodiment, compounds absorb electromagnetic radiation having wavelengths in the UVA, visible and near IR portion of the spectrum. In an embodiment, compounds of the invention absorb electromagnetic radiation between 350 to 1300 nm. In an embodiment, compounds of the invention absorb electromagnetic radiation having wavelengths between 400 to 900 nm. In an embodiment, compounds of the invention absorb electromagnetic radiation having wavelengths between 300 to 500 nm. In an embodiment, the compounds of the invention exhibit luminescence between 520 to 650 nm. In an embodiment, some compounds of the invention absorb electromagnetic radiation and generate fluorescence having wavelengths between 350 to 1300 nm, optionally between 400 to 900 nm. In an aspect of the invention, it is desirable for the compounds to absorb and emit at longer wavelengths to enhance optical detection methods due to enhanced tissue penetration from minimized absorption from hemoglobin, water, lipids and other substances present in a biological system.

In an aspect of the invention, tetra-substituted pyrazine derivatives of the invention having PEG groups are hydrophilic. Increasing the number of PEG groups on the pyrazine derivatives is believed to increase the terminal half-life in circulation of the body. It is believed that lower molecular weight PEG chains (<6000 Da) are filtered by the glomerulus and not absorbed by renal tubules. These characteristics are useful in tailoring the compound to have the desired characteristics.

In an aspect of the invention, compounds of the invention have percent plasma binding of 20% or less. In an aspect of the invention, compounds of the invention have percent plasma binding of 15% or less. In an aspect of the invention, compounds of the invention have percent plasma binding of 10% or less. In an embodiment, compounds of the invention have a percent plasma binding selected over the range over 1-15%, optionally 1-10%. As used herein, "percent plasma binding" is the percentage amount of compound that binds to plasma upon administration to a subject, such as a human subject. In an embodiment of the invention, compounds of the invention are highly cleared in the urine in a patient a period of time on the order of hours. In a particular embodiment, compounds of the invention are at least 80% cleared in the urine within 10 hours after administration.

In an aspect of the present invention, a compound of the invention is used in an optical imaging, medical imaging, diagnostic, visualization, monitoring, surgical, biomedical or therapeutic procedure on a patient. In an aspect of the present invention, the invention is directed to performing an optical imaging, medical imaging, diagnostic, visualization, monitoring, surgical, biomedical or therapeutic procedure on a patient. In an aspect of the present invention, the invention is directed to a method of performing a medical imaging procedure or diagnostic procedure on a patient. The method comprises administering a diagnostically effective amount of the compound to a subject, wherein the compound is differentially separated from a bodily fluid of the subject by an organ, tissue or system in the subject; and detecting the administered compound. In an aspect, the compound can be detected chemically, where a sample of a bodily fluid is analyzed after administration of the compound and the concentration of the compound is measured. In an embodiment of this aspect of the invention, the compound is administered into a bodily fluid.

In an aspect of the present invention, the medical imaging procedure or diagnostic procedure comprises detecting electromagnetic radiation emitting or luminescing from the compound in the subject. In an aspect of the medical imaging procedure or diagnostic procedure of the present invention, exposing the compound administered to the subject to electromagnetic radiation changes an optical property of the compound. In an aspect of the invention, the change in optical property of the compound administered from exposure to electromagnetic radiation is measured or monitored.

In an aspect of the invention, the electromagnetic radiation is non-ionizing. In an aspect of the invention, exposing the administered compound to electromagnetic radiation generates luminescence from the compound, such as fluorescence. In an aspect of the invention, the procedure comprises detecting luminescence from the administered compound. In an aspect of the invention, the method comprises generating an image based, at least in part, on the luminescence from the compound. In an aspect of the invention, the luminescence is collected proximate to the subject's ear, hand, head, forehead, or finger. In an aspect of the invention, the luminescence is detected visually. In an aspect of the invention, the luminescence is detected using a camera, charged coupled device, or diode array. In an aspect of the invention, the medical imaging or diagnosing procedure comprises: administering an effective amount of a renally excretable compound of the invention to a subject; exposing a tissue of the subject's renal system having the administered compound to electromagnetic radiation, thereby generating emitted electromagnetic radiation from the compound; detecting the emitted electromagnetic radiation from the compound, thereby visualizing or imaging at least a portion of the renal system of the subject. In an aspect of the invention, the procedure comprises determining if the administered compound is substantially retained in tissue of the subject's renal system. In an aspect of the invention, provided is a compound described herein for use in a biomedical procedure for assessing physiological function of an organ, tissue or system. In an aspect of the invention, a compound of the invention is used in vivo in assessing renal function of a subject. In an aspect of the invention, a compound of the invention is used in vivo in detecting at least a portion of the urinary system of a subject in a surgical procedure. In an aspect of the invention, a portion of the urinary system comprises a ureter, bladder or urethra of the subject. In an aspect of the invention, a compound of the invention is: administered into the bloodstream of a subject; exposed to electromagnetic radiation while in the bloodstream of the subject; and detected within the bloodstream of the subject. In an aspect of the invention, provided is a pharmaceutical composition comprising a compound of the invention and a pharmaceutically acceptable excipient. In an aspect of the invention, provided is a compound of the invention and one or more additional therapeutic agents or diagnostic agents.

The present invention includes therapeutic agents for biomedical applications, including monitoring renal function, comprising purified stereoisomers (e.g., enantiomers and diastereomers), salts (including quarternary salts), and/or ionic forms (e.g., protonated and deprotonated forms) of the compounds of any of formula (FX1)-(FX17), and mixtures thereof. As will be understood by those having general skill in the art, acidic functional groups and basic functional groups of the compounds of any of formula (FX1)-(FX17) can be in protonated or deprotonated states depending on the molecular environment (e.g., pH, ionic strength, composition, etc.), for example during synthesis, formulation and/or administration.

The present invention provides methods of making and using compounds of the invention, including specifically those shown herein, in particular compounds of formulas (FX1) to (FX17). Methods of this aspect of the present invention include in vivo, in vitro and ex vivo methods for biomedical and bioanalytical applications. Methods of the present invention include photodiagnostic and phototherapeutic methods, such as optical imaging, anatomical visualization, endoscopic visualization, and image guided surgery. For some compounds for use in vivo, in vitro or ex vivo for imaging or visualizing, the tissue, organs and/or cells is a kidney, ureter, kidney cell or other portion of the renal system.

In another aspect, described herein are "kits" that include one or more compounds (or pharmaceutically acceptable salt thereof) having a formula (FX1)-(FX17) and a pharmaceutically acceptable carrier in a single package. In other words, the compound (or pharmaceutically acceptable salt thereof) and the pharmaceutically acceptable carrier are packaged together. A kit of this aspect optionally includes instructions (e.g., in the form of a paper product insert) for preparing and/or utilizing a composition that includes the compound (or pharmaceutically acceptable salt thereof) and the pharmaceutically acceptable carrier. In some embodiments, the compound (or pharmaceutically acceptable salt thereof) can have already been combined with (e.g., dissolved or suspended within) the pharmaceutically acceptable carrier prior to placing the same within the packaging. In other embodiments, the compound (or pharmaceutically acceptable salt thereof) can be disposed within a first container, and the pharmaceutically acceptable carrier can be disposed within a second container that is separate and distinct from the first container. In such embodiments, the first and second containers can be found within the same packaging.

Incorporation of a combination of the substituents on the pyrazine ring is particularly beneficial for providing compounds and optical agents having large extinction coefficients in the visible and near infrared regions of the electromagnetic spectrum (e.g., 350 nm-1300 nm, optionally 400 nm to 900 nm), emission in the visible and near infrared regions (e.g., 350 nm-1300 nm, optionally 500-900 nm), a large fluorescence quantum yield (e.g., >0.1) and a Stokes shift useful for optical detection and imaging (e.g., Stokes shift >10 nm). For example, depending on the number of methylene groups present in the substituents linked to the pyrazine ring, the Stokes shift increases by 10 nm or more for some compounds.

In an embodiment, provided herein are methods for a biomedical procedure, such as an imaging procedure, wherein the method comprises: (i) administering (e.g., via intravenous or intraarterial injection, oral administration, topical administration, subcutaneous administration, etc.) to a subject a diagnostically effective amount of the compound having any one of formula (FX1)-(FX17) and (ii) exposing the administered compound to electromagnetic radiation. In an embodiment, the administering step is carried out under conditions sufficient for contacting the compound with a bodily fluid of the subject, wherein the compound is differentially separated from the bodily fluid of the subject by an organ, tissue or system in the subject.

In an embodiment, exposing the administered compound to electromagnetic radiation generates a diagnostically effective amount of luminescence, for example an amount of luminescence allowing for optical detection, visualizing and/or imaging of the compound. In an embodiment, a method of the invention further comprises exposing the administered compound to electromagnetic radiation having sufficient power, fluence, intensity and/or dose (net number of photons provided to the target tissue) to provide optical detection, visualization and/or imaging of the compound. In an embodiment, a method of the invention further comprises generating an image of the luminescence from the compound. In an embodiment, a method of the invention further comprises visualizing the luminescence from the compound.

In an embodiment, the electromagnetic radiation exposed to the compound of any one of formulas (FX1)-(FX17) does not have wavelengths in the X-ray region of the electromagnetic spectrum. In a method, the electromagnetic radiation exposed to the compound of any one of formulas (FX1)-(FX17) does not have wavelengths in the ultraviolet region of the electromagnetic spectrum. In an embodiment, non-ionizing electromagnetic radiation is used in the present methods.

As used herein, pyrazine compounds or derivatives of the present invention include a substituted pyrazine group. For example, the invention provides a pyrazine compound of the Formula A:

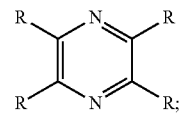

Formula A where the R variables depict "tails" or substituent groups and are further defined herein. In a specific embodiment, pyrazine compounds or derivatives of the present invention include the structure shown in Formula B:

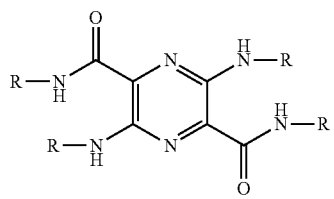

Formula B where the R variables are further defined and illustrated herein.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

BRIEF DESCRIPTION OF THE FIGURES

Those of skill in the art will understand that the figures, described below, are for illustrative purposes only. The figures are not intended to limit the scope of the present teachings in any way.

DETAILED DESCRIPTION

Figure 1:
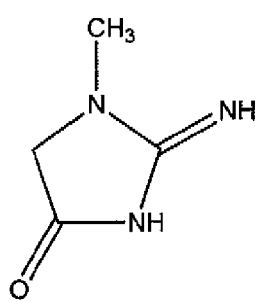
FIG. 1 provides examples of conventional imaging agents.
Figure 1:
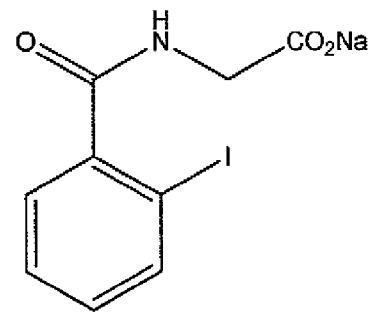
Figure 1:
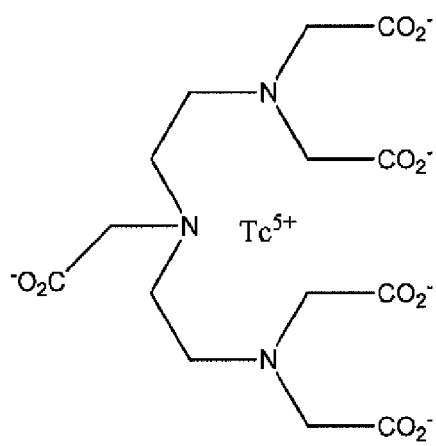
Figure 1:
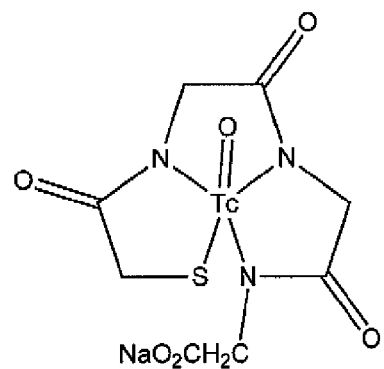

Referring to the drawings, like numerals indicate like elements and the same number appearing in more than one drawing refers to the same element. In general the terms and phrases used herein have their art-recognized meaning, which can be found by reference to standard texts, journal references and contexts known to those skilled in the art. The following definitions are provided to clarify their specific use in the context of the invention.

"Optical agent" generally refers to compounds, compositions, preparations, and/or formulations that absorb, emit, or scatter electromagnetic radiation of wavelength, generally in the range of 350-1300 nanometers, within a biologically relevant environment or condition. In some embodiments, optical agents of the invention, when excited by electromagnetic radiation, undergo emission via fluorescence or phosphorescence pathways. These pathways are useful for diagnostic imaging, visualization, or organ function monitoring. Compounds belonging to this class are commonly referred to as 'optical imaging agents' or 'optical contrast agents'. In an embodiment, an optical agent is a compound described herein.

Optical agents of the present invention can contain fluorophores. The term "fluorophore" generally refers to a component or moiety of a molecule which causes a molecule to be fluorescent. Fluorophores can be functional groups in a molecule which absorb electromagnetic radiation of first specific wavelengths and re-emit energy at second specific wavelengths. The amount and wavelengths of the emitted electromagnetic radiation depend on both the fluorophore and the chemical environment of the fluorophore.

Compounds and compositions of the invention provide optical agents including imaging agents and detectable agents; and conjugates, complexes, and derivatives thereof. Some optical agents of the invention provide detectable agents that can be administered to a subject and subsequently detected using a variety of optical techniques, including optical imaging, visualization, and one-, two-, three- and point optical detection.

Optical agents include, but are not limited to, imaging agents, detectable agents and conjugates, complexes, and derivatives thereof.

When used herein, the terms "diagnosis", "diagnostic" and other root word derivatives are as understood in the art and are further intended to include a general monitoring, characterizing and/or identifying a state of health or disease. The term is meant to encompass the concept of prognosis. For example, the diagnosis of acute renal failure can include an initial determination and/or one or more subsequent assessments regardless of the outcome of a previous finding. The term does not necessarily imply a defined level of certainty regarding the prediction of a particular status or outcome.

As defined herein, "administering" means that a compound or formulation thereof of the invention, such as an optical agent, is provided to a patient or subject, for example in a diagnosably effective amount. The invention includes methods for a biomedical procedure wherein a diagnostically effective amount of a compound having any one of formulas (FX1)-(FX17) is administered to a patient in need of diagnosis, for example to a patient suspected of having a disorder in the renal system. Administering can be carried out by a range of techniques known in the art including intravenous, intraperitoneal or subcutaneous injection or infusion, oral administration, transdermal absorption through the skin, or by inhalation.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Aryl groups include groups having one or more 5-, 6- or 7-member aromatic or heterocyclic aromatic rings. Aryl groups can contain one or more fused aromatic rings. Heterocyclic aromatic rings can include one or more N, O, or S atoms in the ring. Heterocyclic aromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following benzene, naphthalene, naphthoquinone, diphenylmethane, fluorene, anthracene, anthraquinone, phenanthrene, tetracene, naphthacenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, di valent and polyvalent radicals, of the aromatic and heterocyclic aromatic groups listed above provided in a covalently bonded configuration in the compounds of the invention. Aryl groups optionally have one or more aromatic rings or heterocyclic aromatic rings having one or more electron donating groups, electron withdrawing groups and/or other ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:
—COOR where R is a hydrogen or an alkyl group or an aryl group and more specifically where R is methyl, ethyl, propyl, butyl, or phenyl groups all of which are optionally substituted;
—COR where R is a hydrogen, or an alkyl group or an aryl groups and more specifically where R is methyl, ethyl, propyl, butyl, or phenyl groups all of which groups are optionally substituted;
—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which can contain one or more double bonds;
—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which can contain one or more double bonds;
—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which can contain one or more double bonds.
—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
—OCOOR where R is an alkyl group or an aryl groups;
—SO$_2$N(R)$_2$ where R is a hydrogen, an alkyl group, or an aryl group and R and R can form a ring;
—OR where R is H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which are optionally substituted.

As used herein, the term "alkylene" refers to a divalent radical derived from an alkyl group as defined herein. Alkylene groups in some embodiments function as attaching and/or spacer groups in the present compositions. Compounds of the invention include substituted and unsubstituted $C_1$-$C_{20}$ alkylene, $C_1$-$C_{10}$ alkylene and $C_1$-$C_5$ alkylene groups.

As used herein, the term "cycloalkenylene" refers to a divalent radical derived from a cycloalkyl group as defined herein. Cycloalkenylene groups in some embodiments function as attaching and/or spacer groups in the present compositions. Compounds of the invention include substituted and unsubstituted $C_1$-$C_{20}$ cycloalkenylene, $C_1$-$C_{10}$ cycloalkenylene and $C_1$-$C_5$ cycloalkenylene groups.

As used herein, the term "alkenylene" refers to a divalent radical derived from an alkenyl group as defined herein. Alkenylene groups in some embodiments function as attaching and/or spacer groups in the present compositions. Compounds of the invention include substituted and unsubstituted $C_1$-$C_{20}$ alkenylene, $C_1$-$C_{10}$ alkenylene and $C_1$-$C_5$ alkenylene groups.

As used herein, the term "cylcoalkenylene" refers to a divalent radical derived from a cylcoalkenyl group as defined herein. Cycloalkenylene groups in some embodiments function as attaching and/or spacer groups in the present compositions. Compounds of the invention include substituted and unsubstituted $C_1$-$C_{20}$ cylcoalkenylene, $C_1$-$C_{10}$ cylcoalkenylene and $C_1$-$C_5$ cylcoalkenylene groups.

As used herein, the term "alkynylene" refers to a divalent radical derived from an alkynyl group as defined herein. Alkynylene groups in some embodiments function as attaching and/or spacer groups in the present compositions. Compounds of the invention include substituted and unsubstituted $C_1$-$C_{20}$ alkynylene, $C_1$-$C_{10}$ alkynylene and $C_1$-$C_5$ alkynylene groups.

As used herein, the term "halo" refers to a halogen group such as a fluoro (—F), chloro (—Cl), bromo (—Br), iodo (—I) or astato (—At).

As used herein, the term "azo" refers to a group having at least one —N=N— moiety. Azo groups include cyclic and acyclic groups having an —N=N— moiety, for example: (i) aryl-azo groups having an —N=N— moiety directly or indirectly linked to one or more carbocyclic or heterocyclic aromatic rings of a $C_5$-$C_{20}$ aryl, (ii) alkyl-azo groups having an —N=N— moiety directly or indirectly linked to a $C_1$-$C_{20}$ alkyl group and (iii) alkylaryl-azo groups having an —N=N— moiety directly or indirectly linked to a $C_1$-$C_{20}$ alkyl group and one or more carbocyclic or heterocyclic aromatic rings of a $C_5$-$C_{20}$ aryl. In an embodiment, for example, an azo group of a compound of the invention includes a cyclic group having an intra-ring —N=N— group. In an embodiment, for example, an azo group of a compound of the invention includes a cyclic group wherein a carbon-carbon bond in a carbocyclic or heterocyclic ring is replaced with a nitrogen-nitrogen double bond (i.e. N=N). In an embodiment, for example, an azo compound of the invention includes a fused ring structure comprising one or more aromatic groups and one or more alicyclic groups, wherein a carbon-carbon bond in a carbocyclic or heterocyclic ring of the alicyclic group is replaced with a nitrogen-nitrogen double bond (i.e. N=N).

The term "heterocyclic" refers to ring structures containing at least one other kind of atom, in addition to carbon, in the ring. Examples of such atoms include nitrogen, oxygen and sulfur. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

The term carbocyclic refers to ring structures containing only carbon atoms in the ring. Carbon atoms of carbocyclic rings can be bonded to a wide range of other atoms and function groups.

Alicyclic refers to a ring that is not an aromatic ring. Alicyclic rings include both carbocyclic and heterocyclic rings.

Alkoxyalkyl: As used herein, the term "alkoxyalkyl" refers to a substituent of the formula alkyl-O-alkyl.

Polyalkoxyalkyl: As used herein, the term "polyalkoxyalkyl" refers to a substituent of the formula alkylalkoxy)$_n$-alkoxy wherein n is an integer from 1 to 10, preferably 1 to 4, and more preferably for some embodiments 1 to 3.

As used herein, the term "luminescence" refers to the emission of electromagnetic radiation from excited electronic states of atoms or molecules. Luminescence generally refers to electromagnetic radiation emission, such as photoluminescence, chemiluminescence, and electrochemiluminescence, among others. In photoluminescence, including fluorescence and phosphorescence, the excited electronic state is created by the absorption of electromagnetic radiation. Luminescence detection involves detection of one or more properties of the luminescence or associated luminescence process. These properties can include intensity, excitation and/or emission spectrum, polarization, lifetime, and energy transfer, among others. These properties can also include time-independent (steady-state) and/or time-dependent (time-resolved) properties of the luminescence. Representative luminescence techniques include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and bioluminescence resonance energy transfer (BRET), among others. By way of example, when an optical agent is used in the present invention, it is desirable that the wavelength be non-ionizing radiation and be such that it excites the optical agent. This excitation can also cause the molecule to emit part of the absorbed energy at a different wavelength; such emission can be detected using fluorometric techniques as described herein. One skilled in the art can readily determine the most appropriate optical detection technique based, at least in part, on the specific agent(s) administered and/or the particular use (e.g., area to be imaged).

As used herein, the term "controlled-release component" refers to an agent that facilitates the controlled-release of a compound including, but not limited to, polymers, polymer matrices, gels, permeable membranes, liposomes, microspheres, or the like, or any combination thereof. Methods for producing compounds in combination with controlled-release components are known to those of skill in the art.

As used herein, the term "pharmaceutically acceptable" means approved by a regulatory agency of an appropriate federal or state government or listed in the U.S. Pharmacopoeia or other generally recognized pharmacopoeia for use in animals, and more particularly in humans or does not impart significant deleterious or undesirable effect on a subject to whom it is administered and in the context in which it is administered.

As is customary and well known in the art, hydrogen atoms in formulas (FX1)-(FX17) are not always explicitly shown, for example, hydrogen atoms bonded to the carbon atoms of aromatic and alicyclic rings are not always explicitly shown in formulas (FX1)-(FX17). The structures provided herein, for example in the context of the description of formulas (FX1)-(FX17), are intended to convey to one of reasonable skill in the art the chemical composition of compounds of the methods and compositions of the invention, and as will be understood by one of skill in the art, the structures provided do not indicate the specific bond angles between atoms of these compounds.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood that such groups do not contain any substitution or substitution patterns which are sterically impractical and/or synthetically non-feasible. In addition, the compounds of this invention include all stereochemical isomers arising from the substitution of these compounds.

Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Pharmaceutically acceptable salts can be derived from amino acids, including but not limited to cysteine. Other pharmaceutically acceptable salts can be found, for example, in Stahl et al., Handbook of Pharmaceutical Salts Properties, Selection, and Use, Wiley-VCH; Verlag Helvetica Chimica Acta, Zürich, 2002. (ISBN 3-906390-26-8). Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^{31}$, $Br^-$), sulfate, acetates (e.g., acetate, trifluoroacetate), ascorbates, aspartates, benzoates, citrates, and lactate.

The compounds of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

Before the present methods are described, it is understood that this invention is not limited to the particular methodology, protocols and reagents described, as these can vary. It is also to be understood that the terminology used herein is for the purpose of describing particular embodiments only, and is not intended to limit the scope of the invention which will be limited only by the appended claims.

In certain embodiments, the invention encompasses administering optical agents useful in the invention to a patient or subject. A "patient" or "subject", used equivalently herein, refers to an animal. In particular, an animal refers to a mammal, preferably a human. The subject can either: (1) have a condition diagnosable by administration of an optical agent of the invention; or (2) is susceptible to a condition that is diagnosable by administering an optical agent of this invention. The patient can also be involved in a surgical procedure for treatment of a separate disorder.

Compositions of the invention includes formulations and preparations comprising one or more of the present optical agents provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

In an embodiment, the invention provides a pharmaceutical formulation having an active ingredient comprising a composition of the invention, such as a compound of any one of formulas (FX1)-(FX17). In an embodiment, the invention provides a method of synthesizing a composition of the invention or a pharmaceutical formulation thereof, such as a compound of any one of formulas (FX1)-(FX17). In an embodiment, a pharmaceutical formulation comprises one or more excipients, carriers, diluents, and/or other components as would be understood in the art. Preferably, the components meet the standards of the National Formulary ("NF"), United States Pharmacopoeia ("USP"; United States Pharmacopeial Convention Inc., Rockville, Md.), or Handbook of Pharmaceutical Manufacturing Formulations (Sarfaraz K. Niazi, all volumes, ISBN: 9780849317521, ISBN 10: 0849317525; CRC Press, 2004). See, e.g., United States Pharmacopeia and National Formulary (USP 30-NF 25), Rockville, Md.: United States Pharmacopeial Convention; 2007; and 2008, and each of any earlier editions; The Handbook of Pharmaceutical Excipients, published jointly by the American Pharmacists Association and the Pharmaceutical Press (Pharmaceutical Press (2005) (ISBN-10: 0853696187, ISBN-13: 978-0853696186); Merck Index, Merck & Co., Rahway, N.J.; and Gilman et al., (eds) (1996); Goodman and Gilman's: The Pharmacological Bases of Therapeutics, 8th Ed., Pergamon Press. In embodiments, the formulation base of the formulations of the invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopoeias (e.g. DAB, Ph. Eur., BP, NF, USP), as well as other excipients whose properties do not impair a physiological use.

In an embodiment, an effective amount of a composition of the invention is a "diagnostically effective" amount. As used herein, the phrase "diagnostically effective" qualifies the amount of compound administered in diagnosis, for example of a disease state or other pathological condition. The amount achieves the goal of being detectable while avoiding adverse side effects found with higher doses. In an embodiment, an active ingredient or other component is included in a therapeutically acceptable amount. In an embodiment, an active ingredient or other component is included in a diagnostically acceptable amount.

Variations on compositions including salts and ester forms of compounds: Compounds of this invention and compounds useful in the methods of this invention include those of the compounds and formula (s) described herein and pharmaceutically-acceptable salts and esters of those compounds. In embodiments, salts include any salts derived from the acids of the formulas herein which acceptable for use in human or veterinary applications. In embodiments, the term esters refers to hydrolyzable esters of compounds of the names and structural formulas herein. In embodiments, salts and esters of the compounds of the formulas herein can include those which have the same or better therapeutic, diagnostic, or pharmaceutical (human or veterinary) general properties as the compounds of the formulas herein. In an embodiment, a composition of the invention is a compound or salt or ester thereof suitable for pharmaceutical formulations.

In an embodiment, the invention provides a method for diagnosing a medical condition comprising administering to a subject (e.g. patient) in need thereof, a diagnostically effective amount of a composition of the invention, such as a compound of any one of formulas (FX1)-(FX17). In an embodiment, the medical condition is acute renal failure or various other diseases, injuries, and disorders, including renal system disorders such as declining renal function, liver failure, renal failure, and failure of one or more organs or aspects of the renal system.

In an embodiment, the invention provides a medicament which comprises a diagnostically effective amount of one or more compositions of the invention. In an embodiment, the invention provides a method for making a medicament for diagnosis or aiding in the diagnosis of a condition described herein, In an embodiment, the invention provides the use of one or more compositions set forth herein for the making of a medicament.

The invention contemplates pharmaceutically active compounds either chemically synthesized or formed by in vivo biotransformation to compounds set forth herein.

In accordance with the present invention, one protocol for assessing physiological function of body cells includes administering an effective amount of a compound represented by Formula (FX1) to a patient. An appropriate dosage of the compound that is administered to a patient is readily determinable by one of ordinary skill in the art and can vary according to the clinical procedure contemplated, generally ranging from about 1 nanomolar to about 100 micromolar. The administration of the compound to the patient can occur in any of a number of appropriate fashions including, but not limited to: (1) intravenous, intraperitoneal, or subcutaneous injection or infusion; (2) oral administration; (3) transdermal absorption through the skin; and (4) inhalation.

Compounds of this invention can be administered as solutions in most pharmaceutically acceptable intravenous carriers known in the art. Pharmaceutically acceptable carriers that are well known to those skilled in the art include, but are not limited to, 0.01-0.1M phosphate buffer or 0.8% saline. Additionally, pharmaceutically acceptable carriers can be aqueous or non-aqueous solutions, suspensions, emulsions, or appropriate combinations thereof. Examples of non-aqueous solvents are propylene glycol, polyethylene glycol, vegetable oils such as olive oil, and injectable organic esters such as ethyl oleate. Examples of aqueous carriers are water, alcoholic/aqueous solutions, emulsions or suspensions, including saline and buffered media. Exemplary parenteral vehicles include sodium chloride solution, Ringer's dextrose, dextrose and sodium chloride, lactated Ringer's or fixed oils. Exemplary intravenous vehicles include fluid and nutrient replenishers, electrolyte replenishers such as those based on Ringer's dextrose, and the like. Preservatives and other additives can also be present, such as, for example, antimicrobials, antioxidants, collating agents, inert gases, and the like.

Suitable diluents, preservatives, solubilizers, emulsifiers, adjuvant and/or excipients are also suitable carriers. Such carriers are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such carriers can influence the physical state, solubility, stability, rate of in vivo release, and/or rate of in vivo clearance.

Still referring to the above-mentioned protocol, the compound can be exposed to visible and/or near infrared light. This exposure of the compound to light can occur at any appropriate time but preferably occurs while the compound is located in the body (e.g., within the bloodstream and/or urinary system). Due to this exposure of the compound to the visible and/or near infrared light, the compound luminesces, emitting spectral energy (e.g., visible and/or near infrared light) that can be detected by appropriate detection equipment. The luminescence from the compound tends to exhibit a wavelength range greater than a wavelength range absorbed by the compound during excitation. For example, if an embodiment of the compound absorbs light of about 700 nm, the compound can luminesce, emitting light of about 745 nm.

Detection of the compound (or more particularly, the luminescence therefrom) can be achieved through optical fluorescence, absorbance or light scattering procedures known in the art. In one embodiment, this detection of the luminesced spectral energy can be characterized as a collection of the luminesced spectral energy and a generation of electrical signal indicative of the collected spectral energy. The mechanism(s) utilized to detect the luminescence from the compound that is present in the body can be designed to detect only selected wavelengths (or wavelength ranges) and/or can include one or more appropriate spectral filters. Various catheters, endoscopes, ear clips, hand bands, head bands, surface coils, finger probes and the like can be utilized to expose the compound to light and/or to detect the light luminesced therefrom [30]. This detection of luminescence can be accomplished at one or more times intermittently or can be substantially continuous.

Compounds of this invention can be provided in the form of a kit comprising a compound packaged in a container. In some embodiments, the compound can be dissolved a pharmaceutically acceptable carrier and provided in a single container. The pharmaceutically acceptable carrier can comprise any suitable vehicle, diluent, preservative, solubilizer, emulsifier, adjuvant, excipient and/or the like such as is known in the art and/or as is described above. In some embodiments, the compound can be in one container (e.g., in a dried or lyophilized form), and the pharmaceutically acceptable carrier can be in a separate container, all of which are packaged together in the kit. Kits of the invention can also include a package insert providing instructions for use.

Renal function of a patient can be determined based on the detected luminescence. This can be achieved by using data indicative of the detected luminescence and generating an intensity/time profile indicative of a clearance of the compound from the body. This profile can be correlated to a physiological or pathological condition. For example, the patient's clearance profiles and/or clearance rates can be compared to known clearance profiles and/or rates to assess the patient's renal function and to diagnose the patient's physiological condition. In the case of analyzing the presence of the compound in bodily fluids, concentration/time curves can be generated and analyzed (preferably in real time) using an appropriate microprocessor to diagnose renal function.

Physiological function can be assessed by: (1) comparing differences in manners in which normal and impaired cells and/or tissues remove a compound of the invention from the bloodstream; (2) measuring a rate or an accumulation of a compound of the invention in organs or tissues; and/or (3) obtaining tomographic images of organs or tissues having a compound of the invention associated therewith.

In an embodiment, a composition of the invention is isolated or purified. In an embodiment, an isolated or purified compound can be at least partially isolated or purified as would be understood in the art.

The invention is further detailed in the following Examples, which are offered by way of illustration and are not intended to limit the scope of the invention in any manner.

General Experimental Conditions: Unless otherwise noted, all reagents are used as supplied. All discrete (mono disperse) methoxy terminated poly (ethylene glycol) (PEG) reagents are purchased from Quanta BioDesign, Ltd., Powell, Ohio. RP-LC/MS (ESI, positive ion mode) analyses re carried out on a Waters Micromass ZQ system equipped with a PDA detector using a ThermoElectron Hypersil Gold C18 3 μm (4.6 mm×50 mm) column (gradient: 5-95% B/6 min; flow rate: 1 mL/min; mobile phase A: 0.05% TFA in $H_2O$; mobile phase B: 0.05% TFA in $CH_3CN$). Preparative RP-HPLC is carried out using a Waters Dual Pump system equipped with a Liquid Handler and a PDA detector [column: Waters XBridge™ or Sunfire™ Prep C18 OBD™ 5 μm 30×150 mm; $\lambda_{max}$: PDA (200-600 nm); flow: 50 mL/min; gradient: 5-20 to 5-95% B/10 min; mobile phase A: 0.1% TFA in $H_2O$; mobile phase B: 0.1% TFA in $CH_3CN$]. RP-HPLC analyses are carried out on Agilent 1200 series system equipped with a UV detector [(column: Phenomenex Luna 5 μm C18(2) 100 Å 250×4.6 mm; flow: 1 mL/min; gradient: 20-80% B/20 min; mobile phase A: 0.1% TFA in $H_2O$; mobile phase B: 0.1% TFA in $CH_3CN$)]. $^1$NMR spectra re recorded on either a Varian Gemini-300 or a VNMRS-500 spectrometer and chemical shifts are expressed in parts per million (δ) relative to TMS (δ=0) as an internal standard. HRMS (ESI) data is obtained on a Thermo Scientific LTQ-Orbitrap mass spectrometer equipped with an IonMax electrospray ionization source in FTMS (Fourier Transform) mode with resolution ≥30K.

Statement Regarding Correlation of Formula Identification Numbers

Certain compounds described herein are meant to correspond to the compounds of Example 1 and Example 2, below. The compound having formula (FX16), for example, is intended to correspond to compound 1 of Example 1. Additionally, the compound having formula (FX17) is intended to correspond to the compound 4 of Example 2. Should any discrepancy exist between formula (FX16) and compound 1, or formula (FX17) and compound 4, it is intended that all compounds that are encompassed by the structures and description disclosed herein are included.

Example 1

$N^2,N^5$-Bis(38-oxo-2,5,8,11,14,17,20,23,26,29,32,35-dodecaoxa-39-azahentetracontan-41-yl)-3,6-bis(propylamino)pyrazine-2,5-dicarboxamide (1)

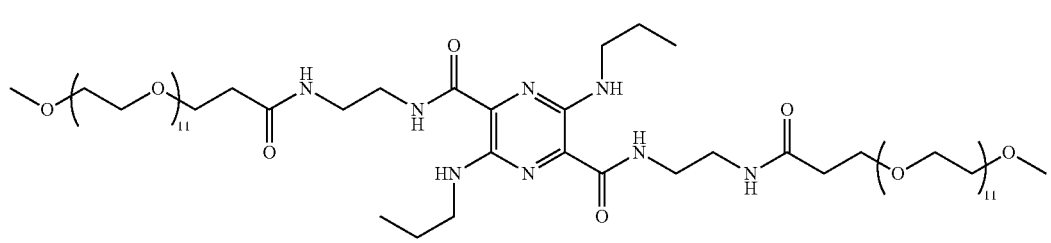

1

Step 1. Synthesis of $N^2,N^5$-bis[2-(tert-butoxycarbonyl)aminoethyl]-3,6-bis(propylamino)pyrazine-2,5-dicarboxamide (2).

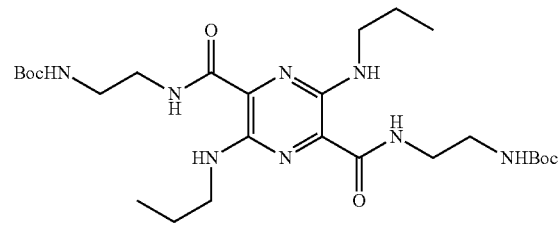

2

Figure 2:
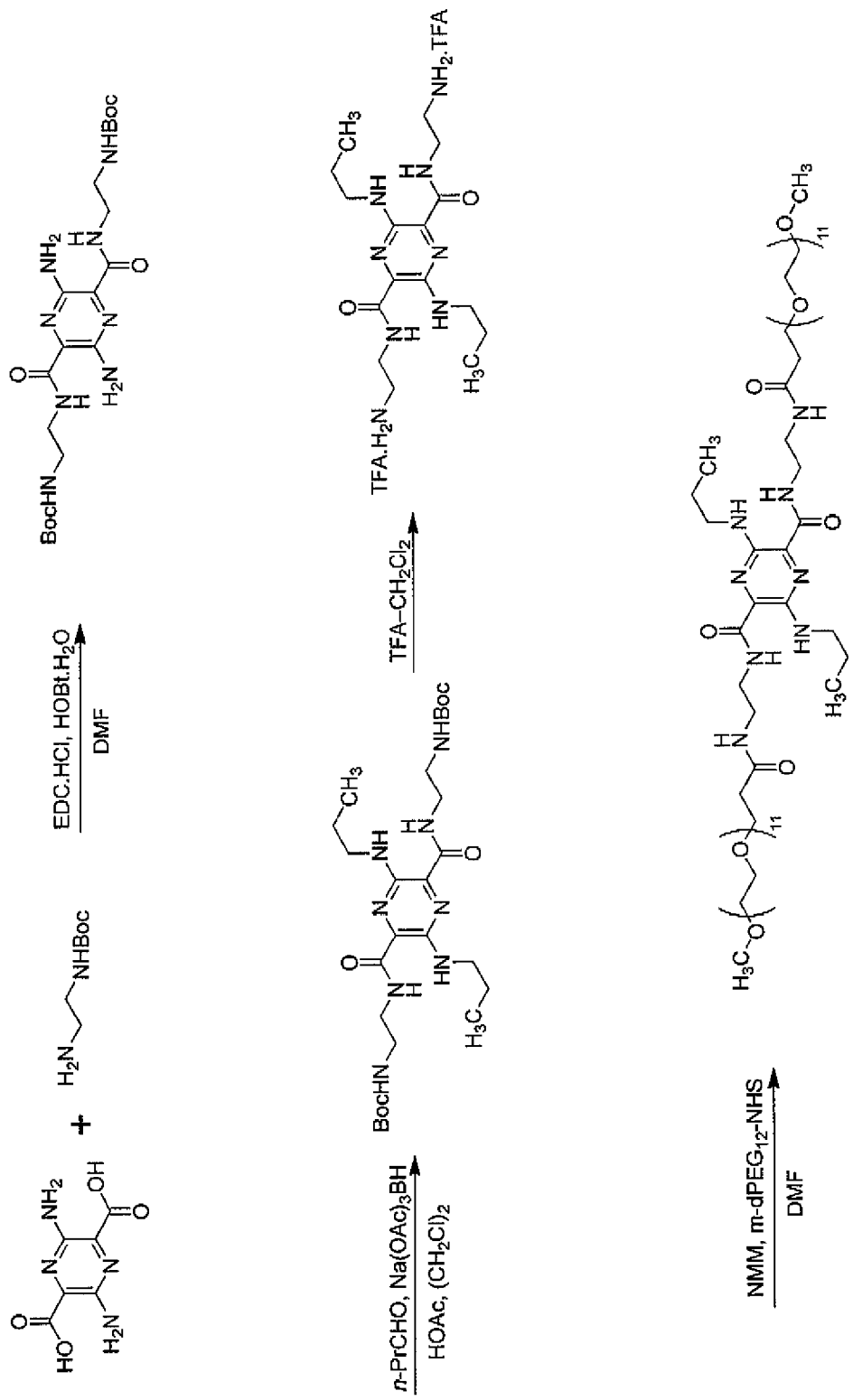
FIG. 2 provides a synthetic scheme for the compound of Example 1.

This compound was prepared from 3,6-diaminopyrazine-2,5-dicarboxylic acid in 62% yield in two steps in the manner set forth in U.S. Provisional Patent Application No. 61/082,296, the disclosure of which is incorporated herein in its entirety. A synthetic scheme is also provided in FIG. 2.

Step 2. $N^2,N^5$-Bis(2-aminoethyl)-3,6-bis(propylamino) pyrazine-2,5-dicarboxamide bis-TFA salt (3).

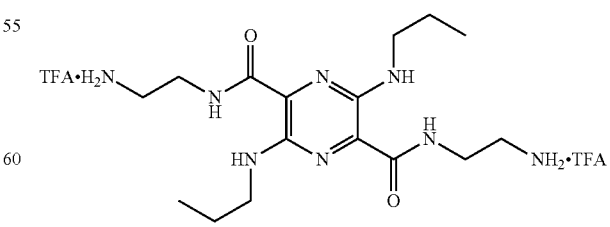

3

To a solution of $N^2,N^5$-bis[2-(tert-butoxycarbonyl)aminoethyl]-3,6-bis(propylamino)pyrazine-2,5-dicarboxamide (2, 0.430 g, 0.759 mmol) in anhydrous $CH_2Cl_2$ (5 mL), was added TFA (5 mL) carefully while stirring at ice-bath temperature. After few minutes the reaction mixture was slowly allowed to warm to room temperature in an atmosphere of argon. The reaction mixture was concentrated in vacuo, the viscous residue was co-evaporated with $CH_2Cl_2$ (4×20 mL), and then dried overnight under high vacuum to give bis-TFA salt 3 (quantitative): RP-LC/MS (ESI) m/z 367.3 $(M+H)^+$ ($t_R$=3.36 min).

Step 3. To a solution of the above bis-TFA salt 3 (0.759 mmol) in anhydrous DMF (7 mL), 4-methylmorpholine NMM (0.835 mL, 7.59 mmol) was added at 0° C., and stirred for 30 min in an atmosphere of argon. Then a solution of m-dPEG$_{12}$-NHS (1.25 g, 1.82 mmol) in anhydrous $CH_2Cl_2$ (3 mL) was added and the reaction mixture was stirred overnight at ambient temperature. Most of the solvents were removed under high vacuum and the crude product (1.82 g) was subjected to purification by preparative RP-HPLC (XBrdige, 20-50% B/10 min). The pure fractions were concentrated in vacuo, the residue was co-evaporated with $CH_3CN$ (3×10 mL), and then dried under high vacuum to give 1 (0.481 g, 42%) as a brick-red sticky solid: $^1H$ NMR (DMSO-$d_6$) characteristic br s at δ 3.50 and s at δ 3.23 for poly(ethylene glycol) moiety; HPLC (264 nm) 90% ($t_R$=17.63 min); LC/MS (ESI) m/z 1508.9 $(M+H)^+$. HRMS (ESI) m/z calculated for $C_{68}H_{132}N_8O_{28}$ $(M+2H)^{2+}$ 754.4570. found 754.4568. calculated for $C_{68}H_{131}N_8O_{28}$ $(M+H)^+$ 1507.9067. found 1507.9055.

Example 2

3,6-Bis(propylamino)-$N^2,N^5$-di(2,5,8,11,14,17,20,23,26,29,32,35,38,41,44,47,50,53,56,59,62,65,68,71-tetracosaoxatriheptacontan-73-yl)pyrazine-2,5-dicarboxamide (4)

4

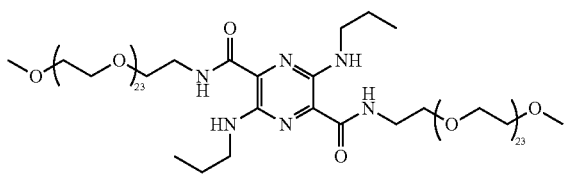

Figure 3:
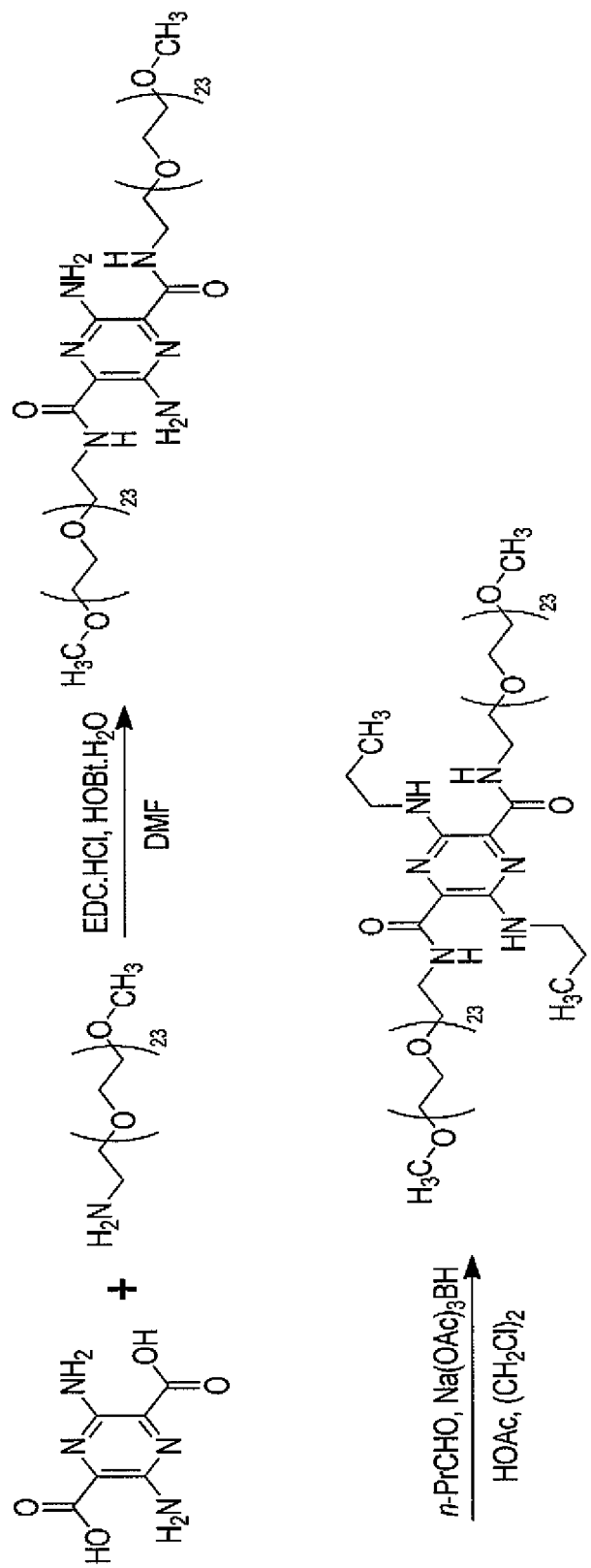
FIG. 3 provides a synthetic scheme for the compound of Example 2.

Step 1. Synthesis of 3,6-diamino-$N^2,N^5$-di(2,5,8,11,14,17,20,23,26,29,32,35,38,41,44,47,-50,53,56,59,62,65,68,71-tetracosaoxatriheptacontan-73-yl)pyrazine-2,5-dicarboxamide (5). A synthetic scheme is also provided in FIG. 3.

5

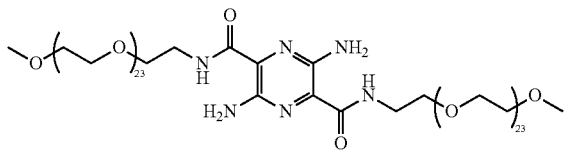

To a mixture of 3,6-diaminopyrazine-2,5-dicarboxylic acid (0.073 g, 0.367 mmol) and m-dPEG™24 amine (1.00 g, 0.919 mmol) in anhyd DMF (20 mL), HOBt.$H_2O$ (0.136 g, 0.888 mmol) and EDC.HCl (0.194 g, 1.01 mmol) were added with stirring at 0° C. in an atmosphere of argon. Then the reaction mixture was slowly allowed to warm to r.t. and stirred overnight. Most of the DMF was removed under high vacuum, the viscous residue was dissolved in $CHCl_3$ (150 mL), and successively washed with water (×2) and brine (50 mL portions). Solvent was removed and the residue was dried under high vacuum to give the crude bis-amide 5 (2.15 g): RP-LC/MS (ESI) m/z 780.3 $(M+3H)^{3+}$, 1169.6 $(M+2H)^{2+}$ ($t_R$=3.62 min).

Step 2. To a solution of the above bis-amide 5 (crude, 2.15 g, 0.367 mmol) in anhyd 1,2-dichloroethane (20 mL), propionaldehyde (0.265 mL, 3.67 mmol) and HOAc (0.263 mL, 4.56 mmol) were added at ice-bath temperature while stirring in an atmosphere of argon. Then sodium triacetoxyborohydride (0.779 g, 3.68 mmol) was added in small portions over a 15 min period, resulting reddish suspension was slowly allowed to warm to room temperature and stirred overnight under argon. The reaction was quenched by a slow addition of saturated $NaHCO_3$ (20 mL) at 0° C. The biphasic mixture was stirred for 15 min and extracted with $CHCl_3$ (3×25 mL). The combined organic extracts were washed with water and brine (50 mL each) and then dried over $Na_2SO_4$. Solvents were removed in vacuo and the crude product (0.945 g) was subjected purification by preparative RP-HPLC (Sunfire, 5-95% B/10 min). The pure fractions were concentrated in vacuo, the residue was co-evaporated with $CH_3CN$ (3×10 mL), and then dried under high vacuum to give 4 (0.281 g, 33%) as a brick-red sticky solid: $^1H$ NMR ($CDCl_3$) characteristic br s at δ 3.64 for poly(ethylene glycol) moiety; RP-HPLC (264 nm) 91% ($t_R$=19.2 min); RP-LC/MS (ESI) m/z 567.4 $(M+H)^+$, 589.4 $(M+Na)^+$ ($t_R$=5.17 min). HRMS (ESI) m/z calculated for $C_{110}H_{218}N_6O_{56}$ $(M+2H)^{2+}$ 1211.7345, found 1211.7343; calculated for $C_{110}H_{217}N_6O_{56}Na$ $(M+H+Na)^{2+}$ 1222.7254, found 1222.7256; calculated for $C_{110}H_{216}N_6O_{56}Na_2$ $(M+2Na)^{2+}$ 1233.7164, found 1233.7173.

Example 3

Figure 4:
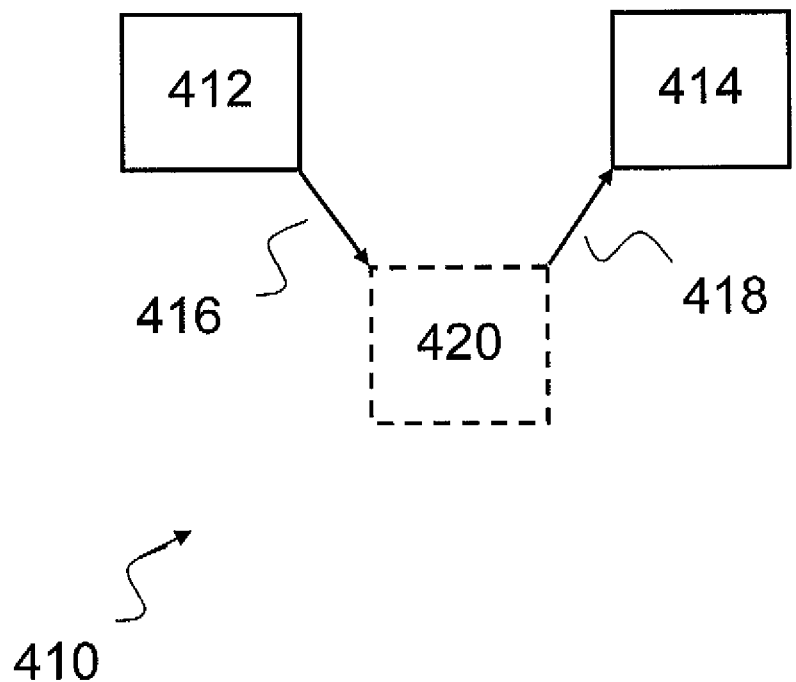
FIG. 4 provides a block diagram of an assembly for assessing renal function.

Protocols for Assessing Renal Function 3.1 General procedures An example of an in vivo renal monitoring assembly 410 is shown in FIG. 4 and includes a light source 412 and a data processing system 414. The light source 412 generally includes or is interconnected with an appropriate device for exposing at least a portion of a patient's body to light therefrom. Examples of appropriate devices that can be interconnected with or be a part of the light source 412 include, but are not limited to, catheters, endoscopes, fiber optics, ear clips, hand bands, head bands, forehead sensors, surface coils, and finger probes. Indeed, any of a number of devices capable of emitting visible and/or near infrared light of the light source can be employed in the renal monitoring assembly 410.

Still referring to FIG. 4, the data processing system 414 of the renal monitoring assembly 410 can be any appropriate system capable of detecting spectral energy and processing data indicative of the spectral energy. For instance, the data processing system 414 can include one or more lenses (e.g., to direct and/or focus spectral energy), one or more filters (e.g., to filter out undesired wavelengths of spectral energy), a photodiode (e.g., to collect the spectral energy and convert the same into electrical signal indicative of the detected spectral energy), an amplifier (e.g., to amplify electrical signal from the photodiode), and a processing unit (e.g., to process the electrical signal from the photodiode). This data processing system 414 is preferably configured to manipulate collected spectral data and generate an intensity/time profile and/or a concentration/time curve indicative of renal clearance of a compound of the present invention from the patient 420.

Indeed, the data processing system 414 can be configured to generate appropriate renal function data by comparing differences in manners in which normal and impaired cells remove a compound of the invention from the bloodstream, to determine a rate or an accumulation of the compound in organs or tissues of the patient 420, and/or to provide tomographic images of organs or tissues having the compound associated therewith.

In one protocol for determining renal function, an effective amount of a compound of the invention is administered to the patient (e.g., in the form of a pharmaceutically acceptable composition). At least a portion of the body of the patient 420 is exposed to visible and/or near infrared light from the light source 412 as indicated by arrow 416. For instance, the light from the light source 412 can be delivered via a fiber optic that is affixed to an ear of the patient 420. The patient can be exposed to the light from the light source 412 before and/or after administration of the compound to the patient 420. In some cases, it can be beneficial to generate a background or baseline reading of light being emitted from the body of the patient 420 (due to exposure to the light from the light source 412) before administering the compound to the patient 420. When the compound that is in the body of the patient 420 is exposed to the light from the light source 412, the compound luminesces, emitting light (indicated by arrow 418) that is detected/collected by the data processing system 414. Initially, administration of the compound to the patient 420 generally enables an initial spectral signal indicative of the initial content of the compound in the patient 420. The spectral signal then tends to decay as a function of time as the compound is cleared from the patient 420. This decay in the spectral signal as a function of time is indicative of the patient's renal function. For example, in a first patient exhibiting healthy/normal renal function, the spectral signal can decay back to a baseline in a time of T. However, a spectral signal indicative of a second patient exhibiting deficient renal function can decay back to a baseline in a time of T+4 hours. As such, the patient 420 can be exposed to the light from the light source 412 for any amount of time appropriate for providing the desired renal function data. Likewise, the data processing system 414 can be allowed to collect/detect spectral energy for any amount of time appropriate for providing the desired renal function data.

Figure 5:
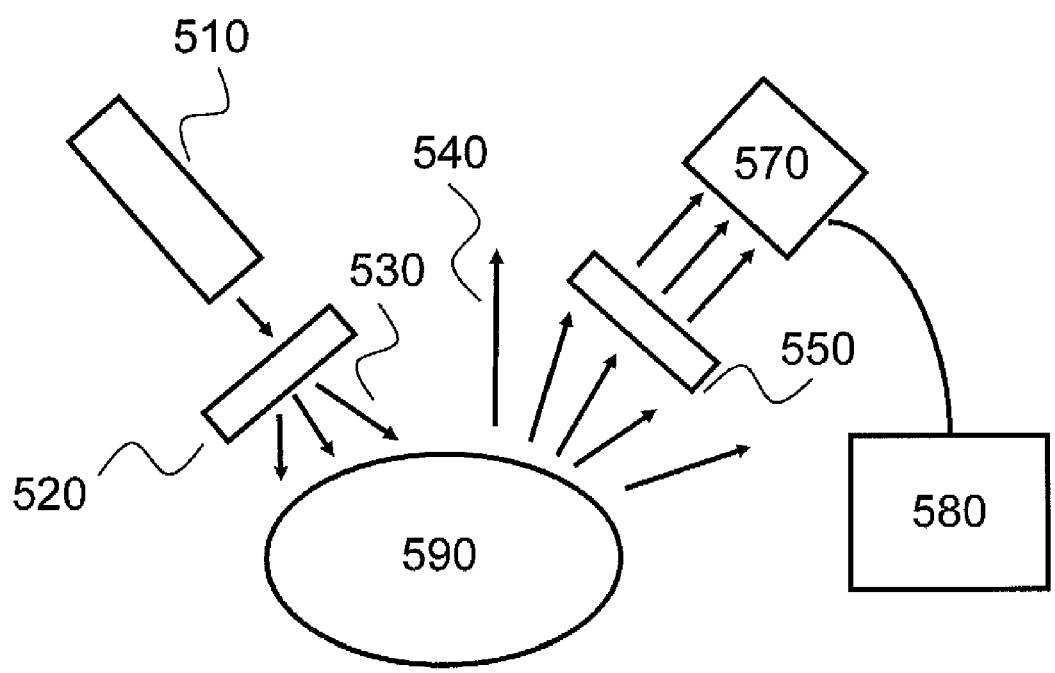
FIG. 5 provides a block diagram of an assembly for optical organ function monitoring.

Referring now to FIG. 5, an example of an in vivo monitoring assembly includes a source of electromagnetic radiation 510, an electromagnetic radiation detector 570 and a data processing system 580. The electromagnetic radiation source 510 generally includes or is interconnected with an appropriate device or devices 520 for exposing at least a portion of a subject's body to electromagnetic radiation 530. Examples of appropriate devices 520 that can be operatively connected to, or be a part of, the electromagnetic radiation source 510 include, but are not limited to, catheters, endoscopes, fiber optics, ear clips, hand bands, head bands, forehead sensors, surface coils, and finger probes. Indeed, any of a number of devices capable of emitting visible and/or near infrared electromagnetic radiation can be employed in a monitoring assembly.

The electromagnetic radiation detector 570 of the monitoring assembly can be any appropriate system capable of collecting and detecting electromagnetic radiation emitted from a subject 590. The electromagnetic radiation detector 570 can be operatively connected to, for example, one or more optical collection elements 550. The optical collection elements 550 of the monitoring assembly can include, among other elements, lenses, mirrors, filters, and fiber optics. Electromagnetic radiation detectors 570 suitable for use with the monitoring assembly include, but are not limited to, CCD detectors, CMOS detectors, photodiode detectors, photodiode array detectors, and photomultiplier tube detectors.

The data processing system 580 of the monitoring assembly can be any appropriate system capable of processing data obtained from the electromagnetic radiation detector 570. For instance, the data processing system 580 can include an amplifier (e.g., to amplify an electrical signal from the detector 570), and a processing unit (e.g., to process the electrical signal from the detector 570). The data processing system 580 is preferably configured to manipulate collected electromagnetic radiation data and generate an intensity as a function of time profile and/or a concentration as a function of time curve indicative of clearance of a detectable agent, such as a compound having formula (FX1)-(FX17), for example a compound of the formula (FX1), from a subject 590. Indeed, the data processing system 580 can be configured to generate appropriate data by comparing amount or concentration of the composition in the bloodstream or bodily fluid, to determine a rate of excretion or an accumulation of the composition in cells, organs or tissues of the subject 590, and/or to provide tomographic images of cells, organs or tissues having the optically functional composition associated therewith.

In one protocol for monitoring, an effective amount of a composition, such as a compound of the formula (FX1), is administered to the subject 590. At least a portion of the body of the subject 590 is exposed to electromagnetic radiation 530 from the electromagnetic radiation source 510. For instance, the electromagnetic radiation 530 from the electromagnetic radiation source 510 can be delivered via a fiber optic 520 that is affixed to an ear of the subject 590. The subject 590 can be exposed to the electromagnetic radiation 530 from the electromagnetic radiation source 510 before, after or during administration of the composition to the subject 590. In some cases, it can be beneficial to generate a background or baseline reading of electromagnetic radiation 540 being emitted from the body of the subject 590, due to exposure to the electromagnetic radiation 530 from the electromagnetic radiation source 510, before administering the composition to the subject 590. When the optically functional composition that is in the body of the subject 590 is exposed to the electromagnetic radiation 530 from the electromagnetic radiation source 510, the optically functional compositions emit electromagnetic radiation 540 that is collected by the optical collection elements 550 and detected by the electromagnetic radiation detector 570. The signal from the electromagnetic radiation detector 570 is then analyzed by the data processing system 580.

3.2. Photophysical properties and protein binding. In general, renally excretable compounds are dissolved in PBS buffer to form a 2 mM stock solution. The UV absorbance properties are determined on a 100 μM solution in PBS using a UV-3101PC UV-Vis-NIR Scanning spectrophotometer system from Shimadzu. The fluorescence properties ($\lambda_{ex}$, $\lambda_{em}$, and CPS at $\lambda_{em}$) are determined on a 10 μM solution in PBS using a Fluorolog-3 spectrofluorometer system from Jobin Yvon Horiba. The percent plasma protein binding are determined on a 20 μM compound solution in rat plasma incubated at 37° C. for 1 h. The separation of free from bound is made using an Amicon Centrifree YM-30 device (Regenerated Cellulose 30,000 MWCO) and a Z400K Refrigerated Universal Centrifuge from Hermle. The concentration of protein-free is determined via HPLC analysis using a set of external calibration standards and fluorescence detection.

3.3. Urine elimination studies. Rat urine elimination studies are conducted in either conscious or anesthetized Sprague-Dawley rats. The test compound (1 mL, 2 mM in PBS) is administered by tail vein injection into conscious, restrained rats, with subsequent collection of urine at the time points of 2, 4 and 6 h post injection. The metabolic cages are washed with water to maximize the recovery of urine discharged at each time point. Alternatively, rats are anesthetized with 100 mg/kg Inactin intraperitoneally, a trachea tube is inserted to maintain adequate respiration, and 1 mL of test compound is injected into the lateral tail vein. Rats are placed on 37° C. heating pad during the entire experiment. At 6 h post injection, the abdomen is opened, and the urine is removed from the bladder using a 21 gauge needle and a 3 cc syringe. Quantitation of each compound in urine is performed via HPLC analysis using a set of external calibration standards and fluorescence detection. The percent recovery of compound in urine at each time point is calculated based on the balance of mass.

Figure 6:
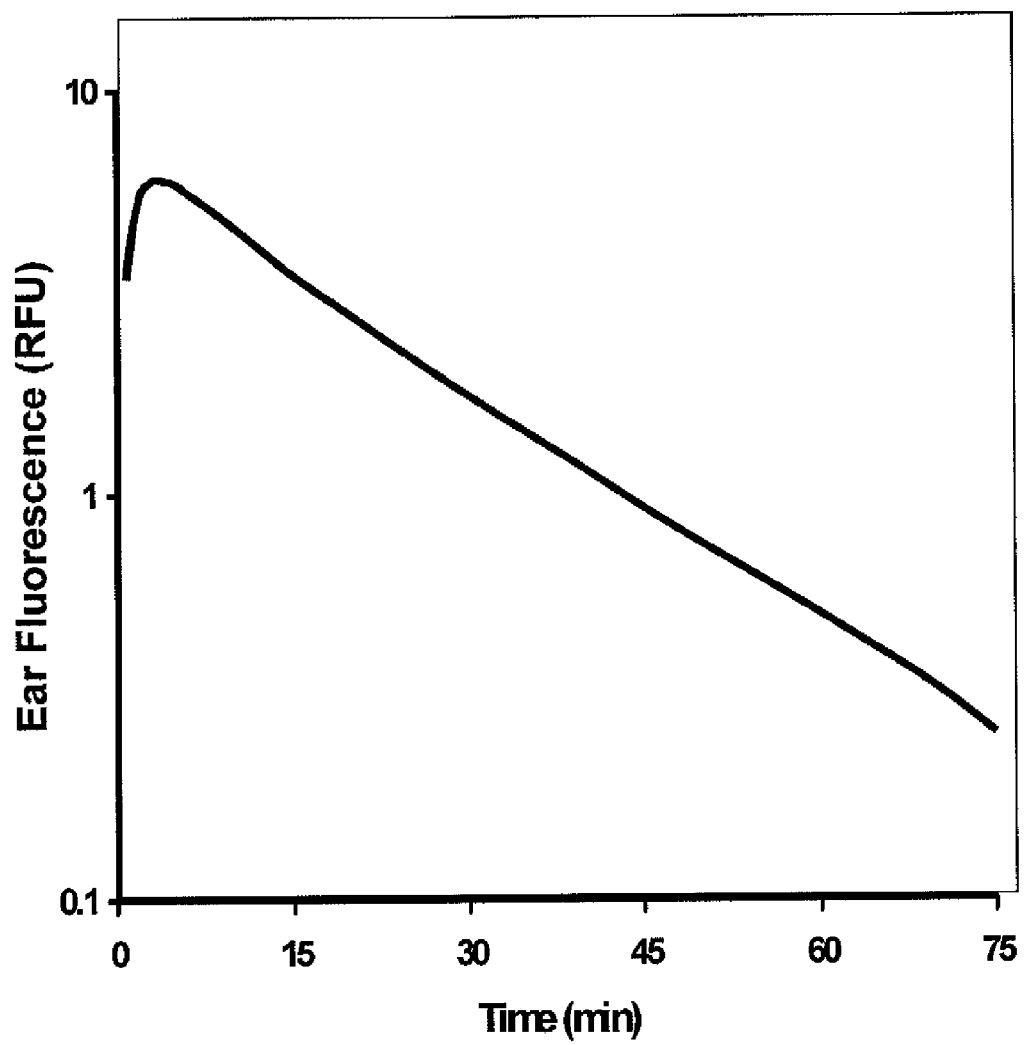
FIG. 6 provides a plot illustrating non-invasive in vivo fluorescence as a function of time following delivery of a renally excretable compound.

3.4. Non-Invasive optical pharmacokinetic studies. Male Sprague-Dawley rats (330-380 g) are anesthetized by Inactin (I.P.) or 2% Isoflurane gas anesthesia delivered by a small rodent gas anesthesia machine (RC2, Vetequip, Pleasanton, Calif.). The animals are placed on a heated board where temperature is maintained between 36-38° C. One ear lobe is glued flat to a glass slide positioned approximately 2 mm beneath a fiber optic bundle for recording fluorescence from a test compound passing through the ear. After a 100 second baseline recording, 1 mL of a 2 mM solution is injected into the tail-vein of the rat and the fluorescence signal corresponding to plasma and tissue distribution and subsequent renal clearance of the compound is monitored at the ear. The pharmacokinetic parameters of the compounds are analyzed using WinNonLin pharmacokinetic modeling software (Pharsight, Mountain View, Calif.) and Microsoft (Redmond, Wash.) Excel. This method is used to detect renally excretable compounds of the invention and FIG. 6 provides a plot illustrating non-invasive in vivo fluorescence as a function of time following delivery of a renally excretable compound.

Figure 7:
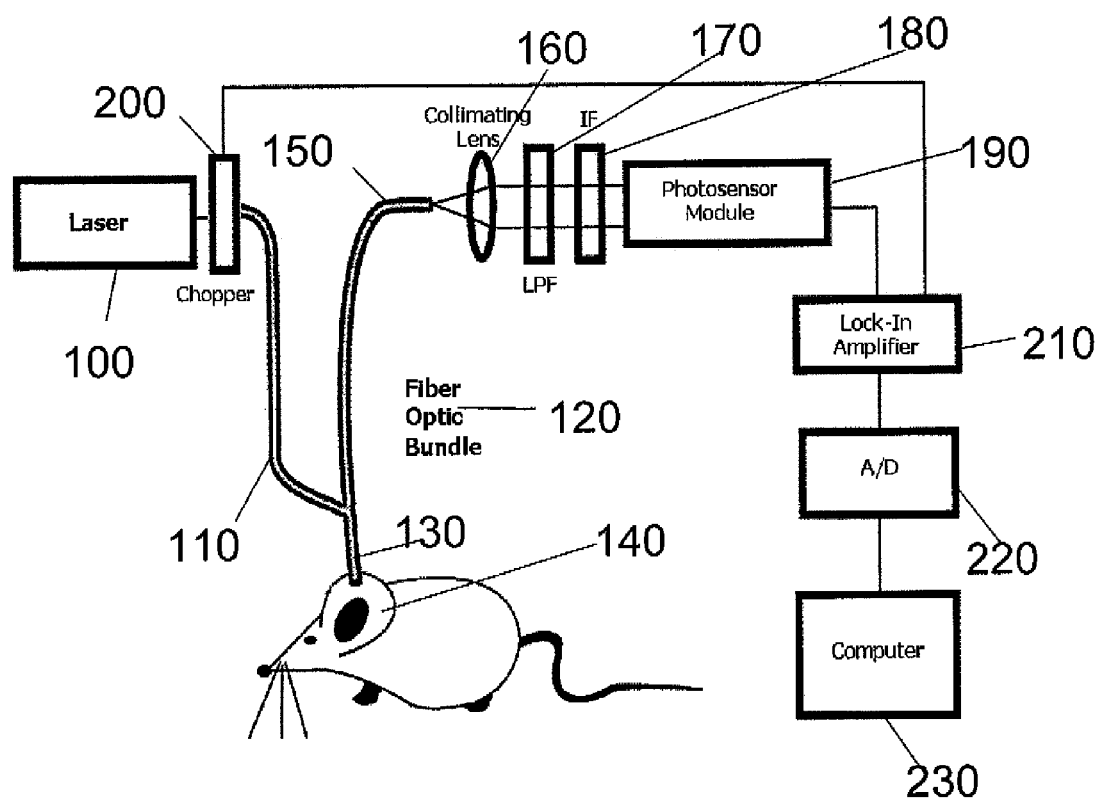
FIG. 7 provides an apparatus for non-invasive in vivo detection of fluorescence.

3.5. Optical monitoring apparatus and protocol. A schematic of the apparatus for non-invasive in vivo detection of fluorescence is shown in FIG. 7. A nominal 473 nm solid state laser source (100) is employed (Power Technology model LDCU12/7314). The laser source (100) is directed into one leg (110) of a silica bifurcated fiber optic bundle (120) (Oriel #77565). The common end of this bifurcated bundle (130) is placed approximately 2 mm from the rat ear (140). The second leg of the bifurcated fiber optic bundle (150) is fitted with a collimating beam probe (160) (Oriel #77644). A long pass filter (170) (Semrock LP02-488RS-25) and narrow band interference filter (180) (Semrock FF01-593/40-25) are placed in front of a photomultiplier tube (190) (Hamamatsu photosensor module H7827-011).

A chopper (200) (Stanford Research Systems model SR540) is placed after the laser (100) and before the launch into the bifurcated cable (120). The output of the photosensor is connected to a lock-in amplifier (210) (Stanford Research Systems model SR830). The lock-in output is digitized (220) (National Instruments NI-USB-6211) and the digitized data is acquired by computer using LabVIEW® data acquisition software (230).

Figure 8:
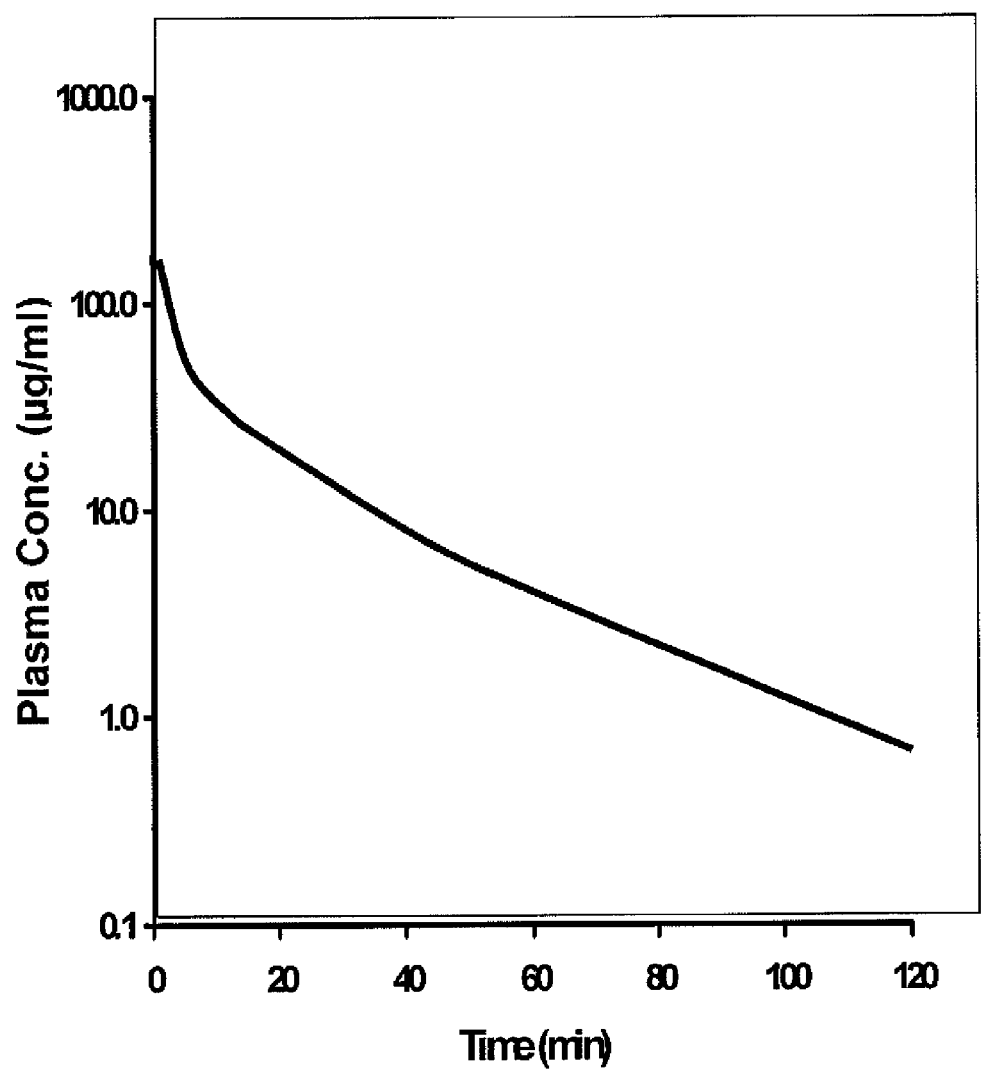
FIG. 8 provides a plot illustrating invasive PK (plasma concentration) as a function of time following delivery of a renally excretable compound.

3.6. Invasive pharmacokinetic (PK) studies. Male Sprague-Dawley rats (330-380 g) are anesthetized by Inactin (I.P.). Rats are surgically instrumented with a trachea tube (PE-190) to facilitate breathing and femoral artery and vein catheters (PE-50 filled with 20 units/mL heparinized saline) for blood sampling and drug administration respectively. After administration of 1 mL of a 2 mM solution of agent, approximately 200 μL of blood is sampled and placed into a heparinized tube (Microtainer Brand Tube w/Lithium Heparin, BD 365971) at 0, 1, 6, 12, 18, 30, 45, 60, 90, 120 min. The concentration of compound in each centrifuged plasma sample is determined via HPLC analysis using a set of external calibration standards and fluorescence detection. The resulting pharmacokinetic parameters of the compound are analyzed using WinNonLin pharmacokinetic modeling software (Pharsight, Mountain View, Calif.). This method is used to detect renally excretable compounds of the invention and FIG. 8 provides a plot illustrating invasive PK (plasma concentration) as a function of time following delivery of a renally excretable compound.

3.7. Probenecid inhibition studies. Six male Sprague-Dawley rats are treated in the same manner as described above in the invasive pharmacokinetic studies. These 6 rats receive 70 mg/kg Probenecid (Sigma-Aldrich; St. Louis, Mo.) 10 min prior to the test compound; this administration is flushed with 0.2 ml NaCl. An additional 6 rats are treated in the same fashion but do not receive probenecid.

Figure 9:
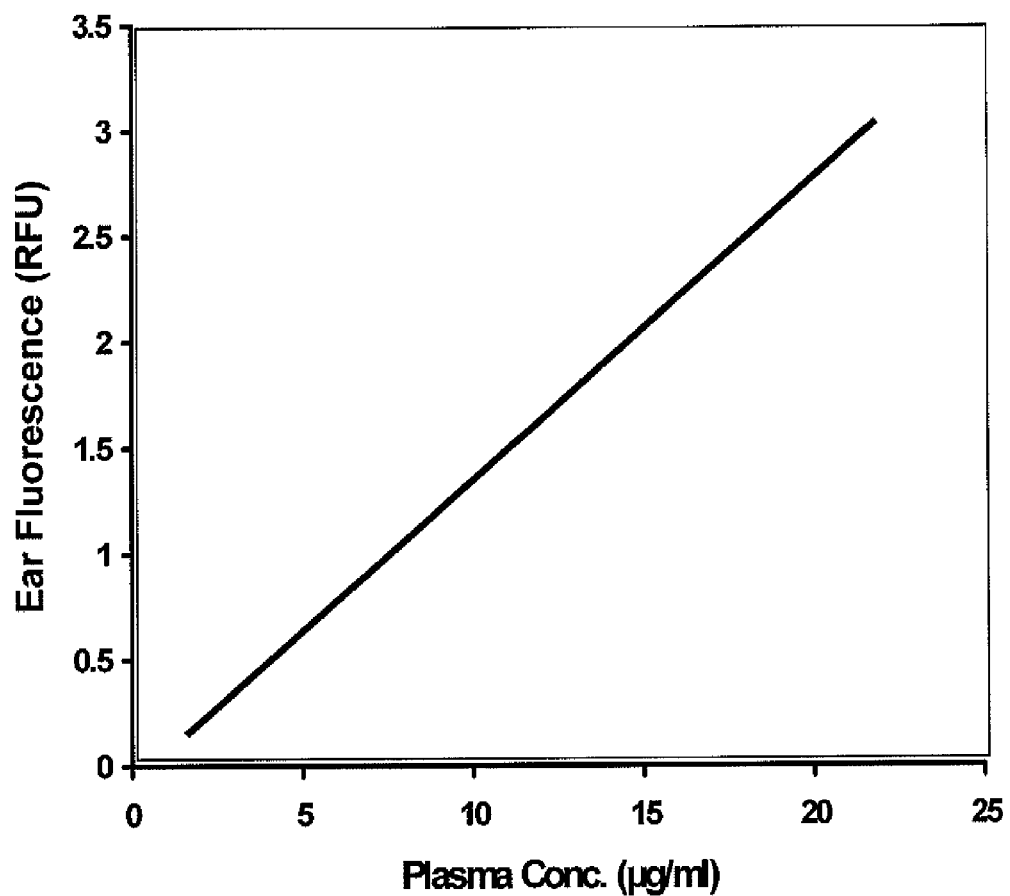
FIG. 9 provides a plot illustrating a linear correlation between the concentration of a renally excretable compound from FIGS. 6 and 8.

3.8. Non-invasive and invasive concentration correlation. Time course data from an invasive plasma pharmacokinetic (PK) experiment and a non-invasive optical monitoring experiment are used to correlate in vivo fluorescence with plasma concentration. By plotting the average relative fluorescence unit response from three optical monitoring runs versus concentration values from an invasive PK experiment for each time point, a good correlation can be demonstrated for a renally excretable compound. FIG. 9 provides a plot illustrating such a linear correlation. PK parameters are determined from the optical clearance data. Glomerular filtration rate (GFR) is estimated with reasonable accuracy from the pharmacokinetic clearance value derived from direct analysis of the non-invasive optical monitoring data.

Example 4

Photophysical and Renal Clearance Properties of Exemplary Compounds

Spectral and pharmacokinetic properties, photophysical properties, urine percentages, tissue clearance (optical) and plasma pharmacokinetic clearances of some compounds were measured according to the methods described below and herein. Table 1 shows the results of these measurements.

TABLE 1

Photophysical properties, urine clearance, optical monitoring, and pharmacokinetic data of the compounds of Example 1 and Example 2

| Compd. | Photophysical Properties | | Percent in Urine[a] (6 hrs) | Tissue clearance (Optical) $T_{1/2}\beta^a$(min) | Plasma PK | |
|---|---|---|---|---|---|---|
| | Excitation $\lambda_{max}$ (nm) | Emission $\lambda_{max}$ (nm) | | | Clearance $T_{1/2}\beta^a$(min) | Clearance[a] (mL/min) |
| 1 | 498 | 613 | | | 21.7 ± 1.3 (3)[b] | 3.0 ± 0.2 (3) |
| 4 | 501 | 611 | 85 ± 2 (3) | 20.5 ± 2.5 (3) | 15.2 ± 6.7 (2) | 4.3 ± 1.1 (2) |

[a]Given as mean ± SEM.
[b]Numbers in parentheses indicate number of test animals.

Example 5

Modified Pyrazine Derivatives and Uses Thereof

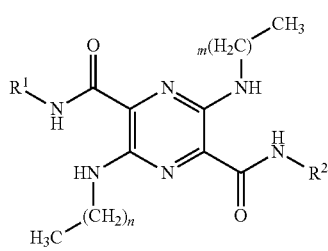

Formula I

In an embodiment, the present invention is directed to compounds of Formula I and their pharmaceutically acceptable salts. With regard to Formula I, each of $R^1$ and $R^2$ is independently —$(CH_2)_a(CH_2CH_2O)_bR^3$, —$(CH_2CH_2O)_bR^3$, or $C_3$-$C_6$ polyhydroxylated alkyl, —$(CH_2)_c(CH_2CH_2O)_d(CH_2)_eNR^4CONR^5(CH_2)_f(CH_2CH_2O)_bR^6$, —$(CH_2)_c(CH_2CH_2O)_d(CH_2)_eNR^4CSNR^5(CH_2)_f(CH_2CH_2O)_bR^6$, —$(CH_2)_c(CH_2CH_2O)_d(CH_2)_eCONR^4(CH_2)_f(CH_2CH_2O)_bR^6$, —$(CH_2)_c(CH_2CH_2O)_d(CH_2)_eNR^4SO_2(CH_2)_f(CH_2CH_2O)_bR^6$, —$(CH_2)_c(CH_2CH_2O)_d(CH_2)_eSO_2NR^4(CH_2)_f(CH_2CH_2O)_bR^6$, —$(CH_2)_c(CH_2CH_2O)_d(CH_2)_eNR^4CO(CH_2)_f(CH_2CH_2O)_bR^6$, —$(CH_2)_c(CH_2CH_2O)_d(CH_2)_eNR^4CO_2(CH_2)_f(CH_2CH_2O)_bR^6$, or —$(CH_2)_c(CH_2CH_2O)_d(CH_2)_eOC(O)NR^4(CH_2)_f(CH_2CH_2O)_bR^6$.

For instance, in some embodiments, each of $R^1$ and $R^2$ is —$(CH_2CH_2O)_bR^3$. In other embodiments, each of $R^1$ and $R^2$ is $C_3$-$C_6$ polyhydroxylated alkyl (e.g., each is $C_3$ polyhydroxylated alkyl, or each is $C_3$ or $C_4$ polyhydroxylated alkyl). In still other embodiments, each of $R^1$ and $R^2$ is —$(CH_2)_a(CH_2CH_2O)_bR^3$. In yet other embodiments, each of $R^1$ and $R^2$ is —$(CH_2)_c(CH_2CH_2O)_d(CH_2)_eNR^4CO(CH_2)_f(CH_2CH_2O)_bR^6$.

Still referring to compounds of Formula I, each occurrence of $R^3$, $R^4$, $R^5$, and $R^6$ is independently —H or $C_1$-$C_3$ alkyl. For example, in some embodiments, each occurrence of $R^3$ can be $C_1$-$C_3$ alkyl (e.g., each occurrence of $R^3$ can be $C_1$ alkyl). In other embodiments, each occurrence of $R^3$ can be —H. Further, in some embodiments, each occurrence of $R^3$ can be —H. In some embodiments, each occurrence of $R^6$ can be $C_1$-$C_3$ alkyl (e.g., each occurrence of $R^6$ can be $C_1$ alkyl).

'm' independently varies from 0 to 5, inclusive (i.e., 'm' can be 0, 1, 2, 3, 4, or 5). For instance, in some embodiments, 'm' can be from 1 to 3, inclusive (e.g., 'm' can be 2 in some embodiments). Likewise, 'n' independently varies from 0 to 5, inclusive (i.e., 'n' can be 0, 1, 2, 3, 4, or 5). For instance, in some embodiments, 'n' can be 1 to 3, inclusive (e.g., 'n' can be 2 in some embodiments). One of the benefits of 'm' and 'n' independently varying from 0 to 5 is that disclosed pyrazine derivatives can be "tuned" to a desired wavelength. In this regard, a pyrazine derivative having both 'm' and 'n' equal to 1 can absorb and/or luminesce at respective light wavelengths that are greater than (e.g., about 10-15 nm greater than) that of a generally similar pyrazine derivative where both 'm' and 'n' are equal to 0. A similar phenomenon could potentially be observed moving from 1 to 2, from 2 to 3, and so on. Accordingly, pyrazine derivatives of Formula I can be designed to absorb and/or luminesce at light wavelengths that can penetrate tissues better than that of lower light wavelengths.

Still referring to compounds of Formula I, each occurrence of 'a' independently varies from 1 to 10, inclusive (i.e., 'a' can be 1, 2, 3, 4, 5, 6, 7, 8, 9, or 10). For instance, in some embodiments, each occurrence of 'a' can independently be 1, 2, 3, 4, 5 or 6. In other embodiments, each occurrence of 'a' can independently be 1, 2, 3, or 4.

Each occurrence of 'b' in compounds of Formula I is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. For example, in some embodiments, each occurrence of 'b' can independently be 1, 2, 3, 4, 5, 6, 7, 8, 9, 10, 11, 12, 13, 14, 15, 16, 17, 18, 19, 20, 21, 22, 23, or 24. In other embodiments, each occurrence of 'b' can independently be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In still other embodiments, each occurrence of b' can independently be 12, 13, 14, 15, 16, 17, 18, 19, 20, 21, 22, 23, or 24.

In compounds of Formula I, each occurrence of 'c' is independently 0, 1, 2, 3, 4, 5, 6, 7, 8, 9, or 10. For example, in some embodiments, each occurrence of 'c' can independently be 0, 1, 2, 3, 4, 5, or 6. In other embodiments, each occurrence of 'c' can independently be 0, 1, 2, 3, or 4. In yet other embodiments, each occurrence of 'c' can be 0.

Still referring to compounds of Formula I, each occurrence of 'd' is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. For example, in some embodiments, each occurrence of 'd' can independently be 0, 1, 2, 3, 4, 5, 6, 7, 8, 9, 10, 11, 12, 13, 14, 15, 16, 17, 18, 19, or 20. In other embodiments, each occurrence of 'd' can independently be 6, 7, 8, 9, 10, 11, 12, 13, 14, 15, 16, 17, 18, 19, 20, 21, 22, 23, or 24. In yet other embodiments, each occurrence of 'd' can be 0.

Each occurrence of 'e' in a compound of Formula I is independently 1, 2, 3, 4, 5, 6, 7, 8, 9, or 10. For instance, in some embodiments, each occurrence of 'e' can independently be 1, 2, 3, 4, 5, or 6. In other embodiments, each occurrence of 'e' can independently be 1, 2, or 3. In yet other embodiments, each occurrence of 'e' can be 2.

Still referring to compounds of Formula I, each occurrence of 'f' is independently 0, 1, 2, 3, 4, 5, 6, 7, 8, 9, or 10. For example, in some embodiments, each occurrence of 'f' can independently be 0, 1, 2, 3, 4, 5, or 6. In other embodiments, each occurrence of 'f' can independently be 0, 1, 2, 3, or 4. In yet other embodiments, each occurrence of 'f' can be 0.

In accordance with the present invention, one protocol for assessing physiological function of body cells includes administering an effective amount of a compound represented by Formula I to a patient. An appropriate dosage of the compound that is administered to a patient is readily determinable by one of ordinary skill in the art and can vary according to the clinical procedure contemplated, generally ranging from about 1 nanomolar to about 100 micromolar. The administration of the compound to the patient can occur in any of a number of appropriate fashions including, but not limited to: (1) intravenous, intraperitoneal, or subcutaneous injection or infusion; (2) oral administration; (3) transdermal absorption through the skin; and (4) inhalation.

Example 6

Surgical Use of Modified Pyrazine Derivatives

The invention includes methods of using the compounds of any of formula (FX1)-(FX17) in a surgical procedure to visualize bodily fluids, organs or tissues. The compounds of any of formula (FX1)-(FX17), for example, can be administered to a subject and allowed to collect in selected bodily fluids, organs, tissues or systems, such as urine and the renal system. The surgical area can then be illuminated with electromagnetic radiation that is absorbed by the compound, for example, electromagnetic radiation of wavelength selected over the range of 350 nanometers to 900 nanometers. The surgeon is then be able to see luminescence, such as fluorescence, from the administered compound, thereby allowing visualization of bodily fluids, organs, or tissue useful for conducting a surgical procedure. For example if a bodily fluid, such as urine, containing the administered compound is exposed to the illuminating electromagnetic radiation, the surgeon will see luminescence resulting therefrom.

Once administered to a subject, the compounds of any of formula (FX1)-(FX17) allow for more successful surgical outcomes, for example due to the ability of a surgeon to identify those bodily fluids, tissue and organs, such as organs and tissue of the renal system, which contain the administered compounds. Identification of these fluids, tissue and/or organs enables the surgeon to avoid unwanted damage to non-target organs and tissues during surgery. If, however, an organ or tissue comprising the administered compound is damaged, for example, the luminescence from the administered compound in bodily fluids at or near the damage site will alert the surgeon to the damage. The surgeon can then take remedial measures and thereby reduce the extent of the damage to the subject.

Example 7

Optical Imaging Using Pyrazine Compounds

In general, molecules absorbing, emitting, or scattering in the visible or NIR region of the electromagnetic spectrum are useful for optical measurement. The high sensitivity associated with fluorescence permits detection without the negative effects of radioactivity or ionizing radiation. Pyrazine compounds of the invention absorb strongly in the red and NIR regions. Furthermore, the electronic properties of these systems are very sensitive to substitution patterns in the ring of the pyrazine compound and allows for "tuning" the absorption and emission properties using the information described herein.

In an embodiment of this aspect, the invention provides a method of using an optical agent, for example, in a biomedical procedure for optically imaging or visualizing a target tissue or a class of target tissues. The present methods include tissue selective imaging and visualization methods, such as imaging or visualization of renal tissue. A method of this aspect comprises the step of administering a diagnostically effective amount of a compound to a subject, wherein the compound is a compound having any of formulae (FX1) to (FX17) or a pharmaceutical preparation thereof. The present methods are useful for imaging or visualizing aspects of the renal system, for example.

In methods of this aspect, the compound that has been administered to the subject then is exposed in vivo to electromagnetic radiation and electromagnetic radiation emitted or scattered by the compound is then detected. In some embodiments, fluorescence is excited from the compound (e.g., due to the electromagnetic radiation exposure), optionally via multiphoton excitation processes. In an embodiment particularly useful for imaging and/or visualization, the method of this aspect further comprises: (i) exposing a compound, such as a compound having any one of formula (FX1) to (FX17), administered to the subject to electromagnetic radiation capable of exciting emission from the compound; and (ii) measuring the emission from the compound. In some embodiments, the methods of the present invention use fluorescence excitation via exposure to electromagnetic radiation having wavelengths selected over the range of 400-1300 nm. For example, optical coherence tomography (OCT) is an optical imaging technique compatible with the present compounds that allows high resolution cross-sectional imaging of tissue microstructure. OCT methods use wavelengths of about 1280 nm. Use of electromagnetic radiation having wavelengths selected over the range of 700 nanometers to 1300 nanometers can be useful for some in situ optical imaging methods of the present invention, including biomedical applications for imaging organs, tissue and/or tumors, anatomical visualization, optical guided surgery and endoscopic procedures. Compounds in present methods can function as contrast agents, optical probes and/or tracer elements. The methods of the present invention include in vivo, in vitro and ex vivo imaging and visualization. The present invention provides methods for a range of clinical procedures, including optical imaging methods and/or visualization guided surgery and/or endoscopic diagnostic and therapeutic procedures.

The techniques utilized to detect the spectral energy from the pyrazine derivative that is present in the body can be designed to detect only selected wavelengths (or wavelength ranges) and/or can include one or more appropriate spectral filters. Various catheters, endoscopes, ear clips, headbands, surface coils, finger probes, and the like can be utilized to expose the pyrazine derivative to light and/or to detect light emitting therefrom. This detection of spectral energy can be accomplished at one or more times intermittently or can be substantially continuous.

Preferably, non-ionizing electromagnetic radiation is provided to a compound of the invention administered to the subject or sample for detecting or imaging a biological sample. As used herein, the term "non-ionizing energy" generally refers to electromagnetic radiation that does not carry enough energy to completely remove at least one electron from an atom or molecule of the patient's body. For example, in some embodiments, non-ionizing energy can include spectral energy ranging in wavelength from about 350 nm to about 1200 nm. In some embodiments, non-ionizing energy can simply include visible and/or near infrared light.

In one embodiment, the spectral properties of the compounds of the invention can be tuned to desired wavelength ranges for excitation and/or emission. This can be useful, for example, in developing a particular imaging technique using a known excitation source.

Example 8

Methods of Monitoring Organ Function Using Pyrazine Compounds

The invention provides compositions and methods for monitoring organ function in a subject. In an embodiment, the present invention provides a method of using a detectable agent, the method comprising:

(i) administering a diagnostically effective amount of a detectable agent to a subject, for example by administering the detectable agent into a bodily fluid of the subject, wherein the detectable agent is differentially separated from the bodily fluid by the organ or tissue; the detectable agent comprising a compound having formula (FX1), or a pharmaceutically acceptable salt or ester thereof:

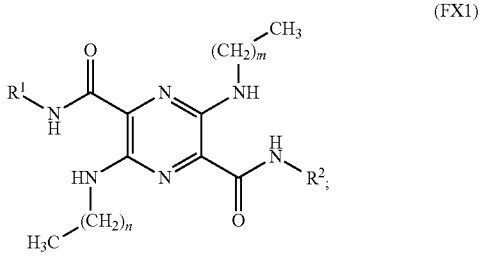

(FX1)

wherein: each of $R^1$ and $R^2$ is —$(CH_2)_a(CH_2CH_2O)_bR^3$, —$(CH_2CH_2O)_bR^3$, —$(CH_2)_c(CH_2CH_2O)_d(CH_2)_eNR^4CONR^5(CH_2)_f(CH_2CH_2O)_bR^6$, —$(CH_2)_c(CH_2CH_2O)_d(CH_2)_eNR^4CSNR^5(CH_2)_f(CH_2CH_2O)_bR^6$, —$(CH_2)_c(CH_2CH_2O)_d(CH_2)_eCONR^4(CH_2)_f(CH_2CH_2O)_bR^6$, —$(CH_2)_c(CH_2CH_2O)_d(CH_2)_eNR^4SO_2(CH_2)_f(CH_2CH_2O)_bR^6$, —$(CH_2)_c(CH_2CH_2O)_d(CH_2)_eSO_2NR^4(CH_2)_f(CH_2CH_2O)_bR^6$, —$(CH_2)_c(CH_2CH_2O)_d(CH_2)_eNR^4CO(CH_2)_f(CH_2CH_2O)_bR^6$, —$(CH_2)_c(CH_2CH_2O)_d(CH_2)_eNR^4CO_2(CH_2)_f(CH_2CH_2O)_bR^6$, —$(CH_2)_c(CH_2CH_2O)_d(CH_2)_eOC(O)NR^4(CH_2)_f(CH_2CH_2O)_bR^6$, or —$(CH_2)_aY^1$; each $Y^1$ is independently —$OR^3$, —$(CHOH)_cR^7$, —$NR^8R^9$, —$CONR^8R^9$, —$NHCO(CH_2)_d(CH_2CH_2O)_bR^6$ or —$NHCO(CHOH)_cR^7$; each of $R^3$, $R^4$, $R^5$, $R^6$ and $R^7$ is independently —H or $C_1$-$C_6$ alkyl; each of $R^8$ and $R^9$ is independently —H, $C_1$-$C_3$ alkyl, —$(CH_2)_a(CHOH)_cR^7$ or —$(CH_2)_a(CH_2CH_2O)_bR^6$; each of a, c, e and f is independently an integer from 0 to 10; each b is independently an integer from 1 to 120; each d is independently an integer from 0 to 120; and each of m and n is independently an integer from 0 to 5;

(ii) exposing the detectable agent in the bodily fluid to electromagnetic radiation for exciting emission from the detectable agent;

(iii) measuring the emission from the detectable agent that is in the bodily fluid; and (iv) determining the physiological function of the organ or tissue of the subject based on measurement of the emission. In an embodiment, for example, the organ or tissue is a kidney, or tissue or cells thereof, of the subject. In an embodiment, for example, the organ or tissue is a liver, or tissue or cells thereof, of the subject.

In an embodiment, a method of monitoring organ function of the invention comprise administering to a patient a compound having any one of formula selected from (FX1)-(FX17), including any of the specific compositions classes and compounds described in connection with formula (FX1)-(FX17). As will be understood by one of skill in the art, the present methods of monitoring organ function expressly include methods of using optical agents wherein the detectable agent includes the compound classes, compounds, and all variations thereof, described herein, including the compound classes, compounds and variations described in connection with any one of formulae (FX1)-(FX17).

In an embodiment, for example, the method further comprises exciting and measuring fluorescence from the detectable agent in the subject for a plurality of times after administration of the detectable agent. In an embodiment, a temporal profile of fluorescence from the detectable agent administered to the subject is determined and evaluated with respect to characterizing organ functioning, for example, by measuring a rate of change in fluorescence (e.g., a decrease in fluorescence) as a function of time, and optionally comparing the measured rate of change in fluorescence to a rate of change characteristic of a subject having a healthy organ or a subject having a known disease condition. Organ function can be assessed in the present methods by comparing differences in the manner in which normal and impaired cells remove the detectable agent (also referred to as a tracer in this context) from the bloodstream, by measuring the clearance or accumulation of these tracers in the organs or tissues, and/or by obtaining tomographic images of the organs or tissues. Blood pool clearance can be measured non-invasively from convenient surface capillaries such as those found in an ear lobe or a finger or can be measured invasively using an endovascular catheter. Accumulation of the tracer within the cells of interest can be assessed in a similar fashion. The clearance of the tracer compounds can be determined by selecting excitation wavelengths and filters for the emitted photons. The concentration versus time curves and/or fluorescence intensity versus time curves can be analyzed (preferably, but not necessarily in real time) by a microprocessor or the like.

Systems and methods of the present invention can optionally include an optical monitoring assembly or device for detecting optical agents of the invention. An example of an in vivo disease state optical monitoring assembly includes a source of electromagnetic radiation, an electromagnetic radiation detector and a data processing system. The electromagnetic radiation source generally includes or is interconnected with an appropriate device or devices for exposing at least a portion of a patient's body to electromagnetic radiation therefrom. Examples of appropriate devices that can be operatively connected to, or be a part of, the electromagnetic radiation source include, but are not limited to, catheters, endoscopes, fiber optics, ear clips, hand bands, head bands, forehead sensors, surface coils, and finger probes. Indeed, any of a number of devices capable of emitting visible and/or near infrared electromagnetic radiation can be employed in an optical monitoring assembly.

The electromagnetic radiation detector of the optical monitoring assembly can be any appropriate system capable of collecting, detecting and measuring the intensity of electromagnetic radiation emitted from a subject. The electromagnetic radiation detector can be operatively connected to, for example, one or more optical collection elements. The optical collection elements of the optical monitoring assembly can include, among other elements, lenses, mirrors, optical filters (e.g., band pass filters and cut off filters), and fiber optics. Electromagnetic radiation detectors suitable for use with the disease state optical monitoring assembly include, but are not limited to, CCD detectors, CMOS detectors, photodiode detectors, photodiode array detectors, and photomultiplier tube detectors.

The data processing system of the optical monitoring assembly can be any appropriate system capable of processing data obtained from the electromagnetic radiation detector. For instance, the data processing system can include an amplifier (e.g., to amplify an electrical signal from the detector), and a processing unit (e.g., to process the electrical signal from the detector). The data processing system is preferably configured to manipulate collected electromagnetic radiation data and generate an intensity as a function of time profile and/or a concentration as a function of time curve indicative of clearance of an optical agent, conjugate, bioconjugate or integrated bioconjugate composition of the present invention from a subject. Indeed, the data processing system can be configured to generate appropriate disease state or health state data by comparing differences in amount of normal and impaired cells in the bloodstream, to determine a rate or an accumulation of the composition in cells, organs or tissues of the subject, and/or to provide tomographic images of cells, organs or tissues having the optical agent, conjugate, bioconjugate or integrated bioconjugate composition associated therewith.

In one protocol for optical monitoring, an effective amount of a composition having formula (FX1)-(FX17) including an optical agent, conjugate, bioconjugate or integrated bioconjugate of the invention is administered to the subject. At least a portion of the body of the subject is exposed to visible and/or near infrared electromagnetic radiation from the electromagnetic radiation source. For instance, the electromagnetic radiation from the electromagnetic radiation source can be delivered via a fiber optic that is affixed to an ear of the subject. The subject can be exposed to electromagnetic radiation from the electromagnetic radiation source before, during or after administration of the composition to the subject. In some cases, it can be beneficial to generate a background or baseline reading of electromagnetic radiation being emitted from the body of the subject, due to exposure to the electromagnetic radiation from the electromagnetic radiation source, before administering the composition to the subject. When the optical agents, conjugates, bioconjugates or integrated bioconjugates of the composition that are in the body of the subject are exposed to the electromagnetic radiation from the electromagnetic radiation source, the optical agents, conjugates, bioconjugates or integrated bioconjugates emit electromagnetic radiation that is collected by optical collection elements and detected by the electromagnetic radiation detector. The signal from the electromagnetic radiation detector is then analyzed by the data processing system.

Initially, administration of the composition to the subject generally enables an electromagnetic radiation signal indicative of the content of the optical agent(s), conjugate(s), bioconjugate(s) or integrated bioconjugate(s) in the subject. In some embodiments, the electromagnetic radiation signal tends to decay as a function of time as the optical agent(s), conjugate(s), bioconjugate(s) or integrated bioconjugate(s) is cleared from the subject. In a subject with a healthy disease state, the electromagnetic radiation signal will decay to near the baseline level as the optical agent(s), conjugate(s), bioconjugate(s) or integrated bioconjugate(s) is cleared from the subject. In a subject with an unhealthy disease condition, the optical agent(s), conjugate(s), bioconjugate(s) or integrated bioconjugate(s) will not be cleared by the subject during the time scale of the monitoring, or will be cleared at a rate which differs from the healthy disease state clearance rate. As a result, the electromagnetic radiation signal can decay at a different rate. Alternatively, the electromagnetic radiation signal can not decrease to the baseline level, but will remain at an elevated level. The difference between this increased electromagnetic radiation signal level (or decay rate) and the baseline level (or decay rate) can be indicative of a disease state in the subject. Some methods of the present invention further comprise comparing the rate of decay of fluorescence intensity at a number of different times so as to assess the state of organ function. As such, the subject can be exposed to the electromagnetic radiation from the electromagnetic radiation source for any amount of time appropriate for providing the desired disease state monitoring data. Likewise, the electromagnetic radiation collection, detection, and data processing systems can be allowed to collect and detect electromagnetic radiation for any amount of time appropriate for providing the desired disease state monitoring data.

In addition to noninvasive techniques, a modified pulmonary artery catheter that can be used to make desired measurements has been developed. This is a distinct improvement over current pulmonary artery catheters that measure only intravascular pressures, cardiac output and other derived measures of blood flow. Currently critically ill patients are managed using these parameters but rely on intermittent blood sampling and testing for assessment of renal function. These laboratory parameters represent discontinuous data and are frequently misleading in many patient populations. Yet, importantly, they are relied upon heavily for patient assessment, treatment decisions, and drug dosing.

The modified pulmonary artery catheter incorporates an optical sensor into the tip of a standard pulmonary artery catheter. This wavelength-specific optical sensor can monitor the organ and/or system function specific elimination of a designed optically detectable chemical entity. Thus, by a method substantially analogous to a dye dilution curve, real-time organ and/or system function can be monitored by the disappearance of the optically detected compound. Appropriate modification of a standard pulmonary artery catheter generally includes making the fiber optic sensor wavelength-specific. Catheters that incorporate fiber optic technology for measuring mixed venous oxygen saturation exist currently.

In an embodiment of this aspect, the present invention provides a method of monitoring a physiological state or condition of a patient undergoing treatment. In this method, an effective amount of an optical agent of the present invention is administered to a mammal (e.g., a patient undergoing treatment). Further, the optical agent that has been administered is exposed to electromagnetic radiation. In addition, electromagnetic radiation transmitted, scattered or emitted by the optical agent is detected. In some embodiments, a change in the wavelengths or intensities of electromagnetic radiation emitted by the optical agent that has been administered to the mammal can be detected and/or measured, optionally as a function of time. Methods of this aspect of the present invention include in situ, real time methods of monitoring renal function in the mammal, wherein the optical agent is cleared by the renal system of the subject.

In an embodiment particularly useful for monitoring physiological function of an organ or tissue of a subject, the method of this aspect further comprises: (i) exposing the detectable agent in the bodily fluid to electromagnetic radiation for exciting emission from the detectable agent; (ii) measuring the emission from the detectable agent that is in the bodily fluid; and (iii) determining the physiological function of the organ or tissue of the subject based on measurement of the emission. The present invention includes fluorescence detection of an agent which is cleared from the bloodstream by the kidneys. Thus, assessment of renal function by in vivo fluorescence detection is encompassed within the scope of the invention. The invention can also be used to monitor the efficiency of hemodialysis. The organ or tissue in some methods is a kidney, or tissue or cells thereof, of the subject, wherein the present invention provides methods for monitoring renal function of the subject.

Methods of this aspect of the present invention can further comprise a variety of optional steps, including analysis of the measured emission from the optical agent as a function of time, such as over a period ranging from 10 minutes to 48 hours. In an embodiment, for example, the method further comprises measuring a blood clearance parameter or profile of the detectable agent administered to the subject. A method of this aspect further comprises comparing the blood clearance parameter or profile of the detectable agent administered to the subject to a reference blood clearance parameter or profile. Useful blood clearance parameters for this aspect of the invention include instantaneous and/or average rates of clearance of the detectable agent. A method of this aspect further comprises comparing the emission from the subject or function thereof with one or more emission reference values or a function thereof of a reference subject. In some embodiments, measuring the emission from the detectable agent comprises measuring emission from the detectable agent in the bodily fluid at a plurality of different times. The clearance of a plurality of separate tracers can be determined simultaneously by selecting excitation wavelengths and filters for the emitted electromagnetic radiation. The concentration versus time or fluorescence intensity versus time curves can be analyzed in real time by a microprocessor. The resulting clearance rates can be calculated and displayed for immediate clinical impact. In cases where unlabeled competing compounds are present, a single blood sample can be analyzed for the concentration of these competing compounds and the results used to calculate a flux (micromoles/minute) through the clearance pathways.

In accordance with one embodiment of the present invention, a method is disclosed for determining cell and/or organ function by measuring the blood pool clearance of an optical agent, sometimes referred to herein as a tracer. The cell and/or organ function can be determined by the rate these cells remove the tracer from the bloodstream. Function can also be assessed by measuring the rate the cells of interest accumulate the tracer or convert it into an active or other form. The agent can be targeted to a group of cells or organ which is a high capacity clearance system. The agent can be an optical agent comprising a pyrazine compound, or derivative or conjugate thereof including bioconjugate, such as the compositions provided in formulae (FX1)-(FX17). For optical agents containing a pyrazine component, blood pool clearance can be measured using a light source-photodetector device that measures tissue absorbance or fluorescence in a non-target site, such as an ear lobe, finger, brain or retina. Accumulation of the tracer within the cells of interest can be assessed in a similar fashion. The detection of such accumulation can be facilitated by using fluorophores which emit in the near infrared wavelengths since body tissues are relatively transparent at these wavelengths.

The present invention can be used for rapid bedside evaluation of biologic functions. For example, data on renal function can be obtained in less than sixty minutes at the bedside after a single intravenous injection. In accordance with one embodiment, a patient can receive a bolus injection of a plurality (e.g., three) of different compounds, each containing a different optical agent (e.g., fluorophore, dye, chromophore).

In an embodiment, the method comprises exposing the detectable agent in the bodily fluid to electromagnetic radiation having wavelengths selected over the range of 350 nm to 1300 nm. Optionally, excitation is achieved using electromagnetic radiation substantially free (e.g., less than about 10% of total radiant energy), of ultraviolet radiation for example to minimize exposure of the subject to electromagnetic radiation capable of causing unwanted cell or tissue damage. Excitation of optical agents can be provided by a wide range of techniques and optical sources as known in the art, including use of laser, fiber optic and/or endoscopic optical sources and methods. The present invention includes methods using multiphoton excitation of optical agents. In an embodiment, the method comprises measuring fluorescence from the detectable agent having wavelengths selected over the range of 350 nm to 1300 nm. Detection of emission, including fluorescence, can be achieved by a wide range of techniques and detection systems as known in the art, including detection by eye (e.g., visualization) and two-dimensional or three-dimensional detection.

Example 9

Pharmaceutical Formulations

Therapeutically Effective Amount

Toxicity and diagnostic efficacy of compounds of the invention can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds that exhibit large therapeutic indices are preferred. While compounds exhibiting toxic side effects can be used, care should be taken to design a delivery system that minimizes potential damage to cells and reduce side effects.

The data obtained from the cell culture assays and animal studies can be used in formulating a range of dosages for use in humans and other mammals. The dosage of such compounds lies preferably within a range of circulating plasma or other bodily fluid concentrations that include the $ED_{50}$ and provides effective imaging results (i.e., ability to image or diagnose a condition or system). The dosage can vary within this range depending upon the dosage form employed and the route of administration utilized. For any compound of the present invention, the visually effective amount can be estimated initially from cell culture assays. A dosage can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful dosages in humans and other mammals. Compound levels in plasma can be measured, for example, by high performance liquid chromatography.

As used herein, a "bodily fluid" is a liquid originating inside a living organism. A bodily fluid can be excretable or secretable from the body. Blood or blood components are particular examples of bodily fluids.

As used herein, "proximate" means near or on. For example, a sensor is located proximate to a light emission source if the sensor can detect the light emission. As used herein, "renal function" is a measure of the functioning of the renal system or component thereof. The renal system includes the kidneys, renal artery, and urinary system.

An amount of a compound that can be combined with a pharmaceutically acceptable carrier to produce a single dosage form will vary depending upon the host treated and the particular mode of administration. It will be appreciated by those skilled in the art that the unit content of a compound contained in an individual dose of each dosage form need not in itself constitute effective imaging amount, as the necessary imaging effective amount could be reached by administration of a number of individual doses. The selection of dosage depends upon the dosage form utilized, and the particular purpose to be achieved according to the determination of those skilled in the art.

The dosage and dosage regime for imaging a disease or condition can be selected in accordance with a variety of factors, including the type, age, weight, sex, diet and/or medical condition of the patient, the route of administration, pharmacological considerations such as activity, efficacy, pharmacokinetic and/or toxicology profiles of the particular compound employed, whether a compound delivery system is utilized, and/or whether the compound is administered as a pro-drug or part of a drug combination. Thus, the dosage regime actually employed can vary widely from subject to subject, or disease to disease and different routes of administration can be employed in different clinical settings.

Subjects are preferably animals (e.g., mammals, reptiles and/or avians), more preferably humans, horses, cows, dogs, cats, sheep, pigs, and/or chickens, and most preferably humans.

In an embodiment, the invention provides a medicament which comprises an imaging or diagnostically effective amount of one or more compositions of the invention, such as a compound of any one of formulas (FX1)-(FX17). In an embodiment, the invention provides a method for making a medicament for imaging or diagnosing of a condition described herein such as renal failure or renal system disorder. In an embodiment, the invention provides a method for making a medicament for diagnosis or aiding in the diagnosis of a condition described herein. In an embodiment, the invention provides the use of one or more compositions set forth herein for the making of a medicament.

Compounds of the invention can have prodrug forms. Prodrugs of the compounds of the invention are useful in embodiments including compositions and methods. Any compound that will be converted in vivo to provide a biologically, pharmaceutically, or diagnostically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug can represent prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of a compound described herein, for example, by hydrolysis in blood or by other cell, tissue, organ, or system processes. Further discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds set forth herein.

In an embodiment, a composition of the invention is isolated or purified. In an embodiment, an isolated or purified compound can be at least partially isolated or purified as would be understood in the art. In an embodiment, the composition of the invention has a chemical purity of 95%, optionally for some applications 99%, optionally for some applications 99.9%, optionally for some applications 99.99% pure, and optionally for some applications 99.999% pure.

Typically, a compound of the invention, or pharmaceutically acceptable salt thereof, is administered to a subject in a diagnostically or imaging effective amount. One skilled in the art generally can determine an appropriate dosage. Factors affecting a particular dosage regimen (including the amount of compound delivered, frequency of administration, and whether administration is continuous or intermittent) include, for example, the type, age, weight, sex, diet, and condition of the subject; the type of pathological condition and its severity; and the nature of the desired therapeutic effect. Pharmacological considerations include compound activity, efficacy, pharmacokinetic, and toxicology profiles of the particular compound used; the route of administration and whether a drug delivery system is utilized; and whether the compound is administered as part of a combination therapy (e.g., whether the agent is administered in combination with one or more other active compounds, other agents, radiation, and the like).

Compositions for oral administration can be, for example, prepared in a manner such that a single dose in one or more oral preparations contains at least about 20 mg of the pyrazine compound per square meter of subject body surface area, or at least about 50, 100, 150, 200, 300, 400, or 500 mg of the pyrazine compound per square meter of subject body surface area (the average body surface area for a human is, for example, 1.8 square meters). In particular, a single dose of a composition for oral administration can contain from about 20 to about 600 mg, and in certain aspects from about 20 to about 400 mg, in another aspect from about 20 to about 300 mg, and in yet another aspect from about 20 to about 200 mg of the pyrazine compound per square meter of subject body surface area. Compositions for parenteral administration can be prepared in a manner such that a single dose contains at least about 20 mg of the pyrazine compound per square meter of subject body surface area, or at least about 40, 50, 100, 150, 200, 300, 400, or 500 mg of the pyrazine compound per square meter of subject body surface area. In particular, a single dose in one or more parenteral preparations contains from about 20 to about 500 mg, and in certain aspects from about 20 to about 400 mg, and in another aspect from about 20 to about 450 mg, and in yet another aspect from about 20 to about 350 mg of the pyrazine compound per square meter of subject body surface area. It should be recognized that these oral and parenteral dosage ranges represent generally preferred dosage ranges, and are not intended to limit the invention. The dosage regimen actually employed can vary widely, and, therefore, can deviate from the generally preferred dosage regimen. It is contemplated that one skilled in the art will tailor these ranges to the individual subject.

It is further contemplated that the pyrazine compounds and salts of this invention can be used in the form of a kit that is suitable for use in performing the methods described herein, packaged in a container. The kit can contain the pyrazine compounds and, optionally, appropriate diluents, devices or device components suitable for administration and instructions for use in accordance with the methods of the invention. The devices can include parenteral injection devices, such as syringes or transdermal patch or the like. Device components can include cartridges for use in injection devices and the like. In one aspect, the kit includes a first dosage form including a pyrazine compound or salt of this invention and a second dosage form including another active ingredient in quantities sufficient to carry out the methods of the invention. The first dosage form and the second dosage form together can include a diagnostically effective amount of the compounds for imaging or diagnosing the targeted condition(s).

This invention also is directed, in part, to pharmaceutical compositions including a diagnostically effective amount of a compound or salt of this invention, as well as processes for making such compositions. Such compositions generally include one or more pharmaceutically acceptable carriers (e.g., excipients, vehicles, auxiliaries, adjuvants, diluents) and can include other active ingredients. Formulation of these compositions can be achieved by various methods known in the art. A general discussion of these methods can be found in, for example, Hoover, John E., Remington's Pharmaceutical Sciences (Mack Publishing Co., Easton, Pa.: 1975). See also, Lachman, L, eds., Pharmaceutical Dosage Forms (Marcel Decker, New York, N.Y., 1980).

The preferred composition depends on the route of administration. Any route of administration can be used as long as the target of the compound or pharmaceutically acceptable salt is available via that route. Suitable routes of administration include, for example, oral, intravenous, parenteral, inhalation, rectal, nasal, topical (e.g., transdermal and intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration.

Pharmaceutically acceptable carriers that can be used in conjunction with the compounds of the invention are well known to those of ordinary skill in the art. Carriers can be selected based on a number of factors including, for example, the particular pyrazine compound(s) or pharmaceutically acceptable salt(s) used; the compound's concentration, stability, and intended bioavailability; the condition being treated; the subject's age, size, and general condition; the route of administration; etc. A general discussion related to carriers can be found in, for example, J. G. Nairn, Remington's Pharmaceutical Science, pp. 1492-1517 (A. Gennaro, ed., Mack Publishing Co., Easton, Pa. (1985)).

Solid dosage forms for oral administration include, for example, capsules, tablets, gelcaps, pills, dragees, troches, powders, granules, and lozenges. In such solid dosage forms, the compounds or pharmaceutically acceptable salts thereof can be combined with one or more pharmaceutically acceptable carriers. The compounds and pharmaceutically acceptable salts thereof can be mixed with carriers including, but not limited to, lactose, sucrose, starch powder, corn starch, potato starch, magnesium carbonate, microcrystalline cellulose, cellulose esters of alkanoic acids, cellulose alkyl esters, talc, stearic acid, magnesium stearate, magnesium oxide, sodium and calcium salts of phosphoric and sulfuric acids, sodium carbonate, agar, mannitol, sorbitol, sodium saccharin, gelatin, acacia gum, alginic acid, sodium alginate, tragacanth, colloidal silicon dioxide, croscarmellose sodium, polyvinylpyrrolidone, and/or polyvinyl alcohol, and then tableted or encapsulated for convenient administration. Such capsules or tablets can contain a controlled-release formulation, as can be provided in a dispersion of the compound or salt in hydroxypropylmethyl cellulose. In the case of capsules, tablets, and pills, the dosage forms also can include buffering agents, such as sodium citrate, or magnesium or calcium carbonate or bicarbonate. Tablets and pills additionally can, for example, include a coating (e.g., an enteric coating) to delay disintegration and absorption. The concentration of the pyrazine compound in a solid oral dosage form can be from about 5 to about 50%, and in certain aspects from about 8 to about 40%, and in another aspect from about 10 to about 30% by weight based on the total weight of the composition.

Liquid dosage forms of the compounds of the invention for oral administration include, for example, pharmaceutically acceptable emulsions, solutions, suspensions, syrups, and elixirs containing inert diluents commonly used in the art (e.g., water). Such compositions also can include adjuvants, such as wetting, emulsifying, suspending, flavoring (e.g., sweetening), and/or perfuming agents. The concentration of the pyrazine compound in the liquid dosage form can be from about 0.01 to about 5 mg, and in certain aspects from about 0.01 to about 1 mg, and in another aspect from about 0.01 to about 0.5 mg per ml of the composition. Low concentrations of the compounds of the invention in liquid dosage form can be prepared in the case that the pyrazine compound is more soluble at low concentrations. Techniques for making oral dosage forms useful in the invention are generally described in, for example, Modern Pharmaceutics, Chapters 9 and 10 (Banker & Rhodes, Editors (1979)). See also, Lieberman et al., Pharmaceutical Dosage Forms: Tablets (1981). See also, Ansel, Introduction to Pharmaceutical Dosage Forms (2nd Edition (1976)).

In some aspects of the invention, tablets or powders for oral administration can be prepared by dissolving the pyrazine compound in a pharmaceutically acceptable solvent capable of dissolving the compound to form a solution and then evaporating when the solution is dried under vacuum. A carrier can also be added to the solution before drying. The resulting solution can be dried under vacuum to form a glass. The glass can then mix with a binder to form a powder. This powder can be mixed with fillers or other conventional tableting agents, and then processed to form a tablet. Alternatively, the powder can be added to a liquid carrier to form a solution, emulsion, suspension, or the like.

In some aspects, solutions for oral administration are prepared by dissolving the pyrazine compound in a pharmaceutically acceptable solvent capable of dissolving the compound to form a solution. An appropriate volume of a carrier is added to the solution while stirring to form a pharmaceutically acceptable solution for oral administration.

"Parenteral administration" includes subcutaneous injections, intravenous injections, intraarterial injections, intraorbital injections, intracapsular injections, intraspinal injections, intraperitoneal injections, intramuscular injections, intrasternal injections, and infusion. Dosage forms suitable for parenteral administration include solutions, suspensions, dispersions, emulsions, and any other dosage form that can be administered parenterally.

Injectable preparations (e.g., sterile injectable aqueous or oleaginous suspensions) can be formulated according to the known art using suitable dispersing, wetting agents, and/or suspending agents. Acceptable vehicles for parenteral use include both aqueous and nonaqueous pharmaceutically-acceptable solvents. Suitable pharmaceutically acceptable aqueous solvents include, for example, water, saline solutions, dextrose solutions (e.g., such as DW5), electrolyte solutions, etc.

In one embodiment, the present pyrazine compounds are formulated as nanoparticles or microparticles. Use of such nanoparticle or microparticle formulations can be beneficial for some applications to enhance delivery, localization, target specificity, administration, etc. of the pyrazine compound. Potentially useful nanoparticles and microparticles include, but are not limited to, micelles, liposomes, microemulsions, nanoemulsions, vesicles, tubular micelles, cylindrical micelles, bilayers, folded sheets structures, globular aggregates, swollen micelles, inclusion complex, encapsulated droplets, microcapsules, nanocapsules or the like. As will be understood by those having skill in the art, the present pyrazine compounds can be located inside the nanoparticle or microparticle, within a membrane or wall of the nanoparticle or microparticle, or outside of (but bonded to or otherwise associated with) the nanoparticle or microparticle. The agent formulated in nanoparticles or microparticles can be administered by any of the routes previously described. In a formulation applied topically, the pyrazine compound is slowly released over time. In an injectable formulation, the liposome, micelle, capsule, etc., circulates in the bloodstream and is delivered to the desired site (e.g., renal system).

Preparation and loading of nanoparticles and microparticles are well known in the art. As one example, liposomes can be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, Liposome Dermatics, Springer-Verlag, Berlin (1992), pp. 69 81; 91 117 which is expressly incorporated by reference herein). Polycaprolactone, poly(glycolic) acid, poly(lactic) acid, polyanhydride or lipids can be formulated as microspheres. As an illustrative example, the present pyrazine compounds can be mixed with polyvinyl alcohol (PVA), the mixture then dried and coated with ethylene vinyl acetate, then cooled again with PVA. In a liposome, the present pyrazine compounds can be within one or both lipid bilayers, in the aqueous between the bilayers, or within the center or core. Liposomes can be modified with other molecules and lipids to form a cationic liposome. Liposomes can also be modified with lipids to render their surface more hydrophilic which increases their circulation time in the bloodstream. The thus-modified liposome has been termed a "stealth" liposome, or a long-lived liposome, as described in U.S. Pat. No. 6,258,378, and in Stealth Liposomes, Lasic and Martin (Eds.) 1995 CRC Press, London, which are expressly incorporated by reference herein. Encapsulation methods include detergent dialysis, freeze drying, film forming, injection, as known to one skilled in the art and disclosed in, for example, U.S. Pat. No. 6,406, 713 which is expressly incorporated by reference herein in its entirety. Optionally, the present compositions and methods include a micelle delivery system, for example, involving one or more PEG-based amphiphilic polymers developed for drug delivery including PEG-poly(s-caprolactone), PEG-poly (amino acid), PEG-polylactide or a PEG-phospholid constructs; a cross linked poly(acrylic acid) polymer system, a phospholipid-based system and/or block copolymer systems comprising one or more of the following polymer blocks a poly(lactic acid) polymer block, a poly(propylene glycol) polymer block; a poly(amino acid) polymer block; a poly (ester) polymer block; and a poly (ε-caprolactone) polymer block, a poly(ethylene glycol) block, a poly(acrylic acid) block, a polylactide block, a polyester block, a polyamide block, a polyanhydride block, a polyurethane block, a polyimine block, a polyurea block, a polyacetal block, a polysaccharide block and a polysiloxane block.

Suitable pharmaceutically-acceptable nonaqueous solvents include, but are not limited to, the following (as well as mixtures thereof): alcohols (these include, for example, o-glycerol formal, β-glycerol formal, 1,3-butyleneglycol, aliphatic or aromatic alcohols having from 2 to about 30 carbons (e.g., methanol, ethanol, propanol, isopropanol, butanol, t-butanol, hexanol, octanol, amylene hydrate, benzyl alcohol, glycerin (glycerol), glycol, hexylene, glycol, tetrahydrofuranyl alcohol, cetyl alcohol, and stearyl alcohol), fatty acid esters of fatty alcohols (e.g., polyalkylene glycols, such as polypropylene glycol and polyethylene glycol), sorbitan, sucrose, and cholesterol); amides (these include, for example, dimethylacetamide (DMA), benzyl benzoate DMA, dimethylformamide, N-hydroxyethyO-lactamide, N,N-dimethylac- etamide-amides, 2-pyrrolidinone, 1-methyl-2-pyrrolidinone, and polyvinylpyrrolidone); esters (these include, for example, acetate esters (e.g., monoacetin, diacetin, and triacetin), aliphatic and aromatic esters (e.g., ethyl caprylate or octanoate, alkyl oleate, benzyl benzoate, or benzyl acetate), dimethylsulfoxide (DMSO), esters of glycerin (e.g., mono, di, and tri-glyceryl citrates and tartrates), ethyl benzoate, ethyl acetate, ethyl carbonate, ethyl lactate, ethyl oleate, fatty acid esters of sorbitan, glyceryl monostearate, glyceride esters (e.g., mono, di, or tri-glycerides), fatty acid esters (e.g., isopropyl myristrate), fatty acid derived PEG esters (e.g., PEG-hydroxyoleate and PEG-hydroxystearate), N-methyl pyrrolidinone, pluronic 60, polyoxyethylene sorbitol oleic polyesters (e.g., poly(ethoxylated)$_{30-60}$ sorbitol poly(oleate)$_{2-4}$, Poly(oxyethylene)$_{15-20}$ monooleate, poly (oxyethylene)$_{15-20}$ mono 12-hydroxystearate, and poly(oxyethylene)$_{15-20}$ mono ricinoleate), polyoxyethylene sorbitan esters (e.g., polyoxyethylene-sorbitan monooleate, polyoxyethylene-sorbitan monopalmitate, polyoxyethylene-sorbitan monolaurate, polyoxyethylene-sorbitan monostearate, and POLYSORBATE 20, 40, 60, and 80 (from ICI Americas, Wilmington, Del.)), polyvinylpyrrolidone, alkyleneoxy modified fatty acid esters (e.g., polyoxyl 40 hydrogenated castor oil and polyoxyethylated castor oils, such as CREMOPHOR EL solution or CREMOPHOR RH 40 solution), saccharide fatty acid esters (i.e., the condensation product of a monosaccharide (e.g., pentoses, such as, ribose, ribulose, arabinose, xylose, lyxose, and xylulose; hexoses, such as glucose, fructose, galactose, mannose, and sorbose; trioses; tetroses; heptoses; and octoses), disaccharide (e.g., sucrose, maltose, lactose, and trehalose), oligosaccharide, or a mixture thereof with one or more $C_4$-$C_{22}$ fatty acids (e.g., saturated fatty acids, such as caprylic acid, capric acid, lauric acid, myristic acid, palmitic acid, and stearic acid; and unsaturated fatty acids, such as palmitoleic acid, oleic acid, elaidic acid, erucic acid, and linoleic acid), and steroidal esters); ethers (these are typically alkyl, aryl, and cyclic ethers having from 2 to about 30 carbons. Examples include diethyl ether, tetrahydrofuran, dimethyl isosorbide, diethylene glycol monoethyl ether), and glycofurol (tetrahydrofurfuranyl alcohol polyethylene glycol ether); ketones (these typically have from about 3 to about 30 carbons. Examples include acetone, methyl ethyl ketone, methyl isobutyl ketone); hydrocarbons (these are typically aliphatic, cycloaliphatic, and aromatic hydrocarbons having from about 4 to about 30 carbons). Examples include benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO); and tetramethylene sulfoxide; oils (these include oils of mineral, vegetable, animal, essential, or synthetic origin). These include mineral oils, such as aliphatic and wax-based hydrocarbons, aromatic hydrocarbons, mixed aliphatic and aromatic based hydrocarbons, and refined paraffin oil; vegetable oils, such as linseed, tung, safflower, soybean, castor, cottonseed, groundnut, rapeseed, coconut, palm, olive, corn, corn germ, sesame, persic, and peanut oil; glycerides, such as mono-, di-, and triglycerides; animal oils, such as fish, marine, sperm, cod-liver, haliver, squaiene, squalane, and shark liver oil; oleic oils; and polyoxyethylated castor oil); alkyl, alkenyl, or aryl halides (these include alkyl or aryl halides having from 1 to about 30 carbons and one or more halogen substituents. Examples include methylene chloride); monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (SOLUTOL HS-15, from BASF, Ludwigshafen, Germany); polyoxyethylene glycerol; sodium laurate; sodium oleate; and sorbitan monooleate. Other pharmaceutically acceptable solvents for use in the invention are well known to those of ordinary skill in the art. General discussion relating to such solvents can be found in, for example, The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics 3d ed., (G. Banker et. al., eds., Marcel Dekker, Inc., New York, N.Y. (1995)), The Pharmacological Basis of Therapeutics, (Goodman & Gilman, McGraw Hill Publishing), Pharmaceutical Dosage Forms, (H. Lieberman et. al., eds., Marcel Dekker, Inc., New York, N.Y. (1980)), Remington's Pharmaceutical Sciences, 19th ed., (A. Gennaro, ed., Mack Publishing, Easton, Pa., (1995)), The United States Pharmacopeia 24, The National Formulary 19, (National Publishing, Philadelphia, Pa. (2000)); Spiegel, A. J., et al., "Use of Nonaqueous Solvents in Parenteral Products," J. Pharma. Sciences, Vol. 52, No. 10, pp. 917-927 (1963).

Solvents useful in the invention include, but are not limited to, those known to stabilize the pyrazine compounds or pharmaceutically acceptable salts thereof. These typically include, for example, oils rich in triglycerides, such as safflower oil, soybean oil, and mixtures thereof; and alkyleneoxy-modified fatty acid esters, such as polyoxyl 40 hydrogenated castor oil and polyoxyethylated castor oils (e.g., CREMOPHOR EL solution or CREMOPHOR RH 40 solution). Commercially available triglycerides include INTRALIPID emulsified soybean oil (Kabi-Pharmacia Inc., Stockholm, Sweden), NUTRALIPID emulsion (McGaw, Irvine, Calif.), LIPOSYN II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), LIPOSYN III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels of from about 25 to about 100% (by weight based on the total fatty acid content) (DHASCO from Martek Biosciences Corp., Columbia, Md.; DHA MAGURO from Daito Enterprises, Los Angeles, Calif.; SOYACAL; and TRAVEMULSION). Ethanol in particular is a useful solvent for dissolving a pyrazine compound or pharmaceutically acceptable salt thereof to form solutions, emulsions, and the like.

Additional components can be included in the compositions of this invention for various purposes generally known in the pharmaceutical industry. These components tend to impart properties that, for example, enhance retention of the pyrazine compound or salt at the site of administration, protect the stability of the composition, control the pH, and facilitate processing of the pyrazine compound or salt into pharmaceutical formulations, and the like. Specific examples of such components include cryoprotective agents; agents for preventing reprecipitation of the pyrazine compound or salt surface; active, wetting, or emulsifying agents (e.g., lecithin, polysorbate-80, TWEEN 80, pluronic 60, and polyoxyethylene stearate); preservatives (e.g., ethyl-p-hydroxybenzoate); microbial preservatives (e.g., benzyl alcohol, phenol, m-cresol, chlorobutanol, sorbic acid, thimerosal, and paraben); agents for adjusting pH or buffering agents (e.g., acids, bases, sodium acetate, sorbitan monolaurate, etc.); agents for adjusting osmolarity (e.g., glycerin); thickeners (e.g., aluminum monostearate, stearic acid, cetyl alcohol, stearyl alcohol, guar gum, methyl cellulose, hydroxypropylcellulose, tristearin, cetyl wax esters, polyethylene glycol, etc.); colorants; dyes; flow aids; non-volatile silicones (e.g., cyclomethicone); clays (e.g., bentonites); adhesives; bulking agents; flavorings; sweeteners; adsorbents; fillers (e.g., sugars such as lactose, sucrose, mannitol, sorbitol, cellulose, calcium phosphate, etc.); diluents (e.g., water, saline, electrolyte solutions, etc.); binders (e.g., gelatin; gum tragacanth; methyl cellulose; hydroxypropyl methylcellulose; sodium carboxymethyl cellulose; polyvinylpyrrolidone; sugars; polymers; acacia; starches, such as maize starch, wheat starch, rice starch, and potato starch; etc.); disintegrating agents (e.g., starches, such as maize starch, wheat starch, rice starch, potato starch, and carboxymethyl starch; cross-linked polyvinyl pyrrolidone; agar; alginic acid or a salt thereof, such as sodium alginate; croscarmellose sodium; crospovidone; etc); lubricants (e.g., silica; talc; stearic acid and salts thereof, such as magnesium stearate; polyethylene glycol; etc.); coating agents (e.g., concentrated sugar solutions including gum arabic, talc, polyvinyl pyrrolidone, carbopol gel, polyethylene glycol, titanium dioxide, etc.); and antioxidants (e.g., sodium metabisulfite, sodium bisulfite, sodium sulfite, dextrose, phenols, thiophenols, etc.). Techniques and compositions for making parenteral dosage forms are generally known in the art. Formulations for parenteral administration can be prepared from one or more sterile powders and/or granules having a compound or salt of this invention and one or more of the carriers or diluents mentioned for use in the formulations for oral administration. The powder or granule typically is added to an appropriate volume of a solvent (typically while agitating (e.g., stirring) the solvent) that is capable of dissolving the powder or granule. Particular solvents useful in the invention include, for example, water, polyethylene glycol, propylene glycol, ethanol, corn oil, cottonseed oil, peanut oil, sesame oil, benzyl alcohol, sodium chloride, and/or various buffers.

Emulsions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the emulsion. Solutions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the solution.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, cocoa butter; synthetic mono-, di-, or triglycerides; fatty acids; and/or polyethylene glycols.

"Topical administration" includes the use of transdermal administration, such as transdermal patches or iontophoresis devices.

If desired, the emulsions or solutions described above for oral or parenteral administration can be packaged in IV bags, vials, or other conventional containers in concentrated form, and then diluted with a pharmaceutically acceptable liquid (e.g., saline) to form an acceptable pyrazine compound concentration before use.

It is understood that this invention is not limited to the particular compounds, methodology, protocols, and reagents described, as these can vary. It is also to be understood that the terminology used herein is for the purpose of describing particular embodiments only, and is not intended to limit the scope of the invention which will be limited only by the appended claims.

Compositions of the invention include formulations and preparations comprising one or more of the present compounds provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

Formulations and Use

Compounds and bioconjugates of the present invention can be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. An individual compound/bioconjugate can be administered in combination with one or more additional compounds/bioconjugates of the present invention and/or together with other biologically active or biologically inert agents. Such biologically active or inert agents can be in fluid or mechanical communication with the compound(s)/bioconjugate(s) or attached to the compound(s)/bioconjugate(s) by ionic, covalent, Van der Waals, hydrophobic, hydrophilic or other physical forces. Administration can optionally be localized in a subject. Administration can optionally be systemic.

Compounds and bioconjugates of the present invention can be formulated by any conventional manner using one or more pharmaceutically acceptable carriers. Thus, the compounds/bioconjugates and their pharmaceutically acceptable salts and solvates can be specifically formulated for administration, e.g., by inhalation or insufflation (either through the mouth or the nose) or oral, buccal, parenteral or rectal administration. The compounds/bioconjugates can take the form of charged, neutral and/or other pharmaceutically acceptable salt forms. Examples of pharmaceutically acceptable carriers include, but are not limited to, those described in REMINGTON'S PHARMACEUTICAL SCIENCES (A. R. Gennaro, Ed.), 20th edition, Williams & Wilkins PA, USA (2000).

Compounds and bioconjugates of the present invention can be formulated in the form of solutions, suspensions, emulsions, tablets, pills, capsules, powders, controlled- or sustained-release formulations and the like. Such formulations will contain a therapeutically effective amount of the compound/bioconjugate, preferably in purified form, together with a suitable amount of carrier so as to provide the form for proper administration to the patient. The formulation should suit the mode of administration.

Parenteral Administration

Compounds and bioconjugates of the present invention can be formulated for parenteral administration by injection (e.g., by bolus injection or continuous infusion). Formulations for injection can be presented in unit dosage form in ampoules or in multi-dose containers with an optional preservative added. The parenteral preparation can be enclosed in ampoules, disposable syringes or multiple dose vials made of glass, plastic or the like. The formulation can take such forms as suspensions, solutions or emulsions in oily or aqueous vehicles, and can contain formulatory agents such as suspending, stabilizing and/or dispersing agents.

For example, a parenteral preparation can be a sterile injectable solution or suspension in a nontoxic parenterally acceptable diluent or solvent (e.g., as a solution in 1,3-butanediol). Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid can be used in the parenteral preparation.

Alternatively, compounds and bioconjugates of the present invention can be formulated in powder form for constitution with a suitable vehicle, such as sterile pyrogen-free water, before use. For example, a compound/bioconjugate suitable for parenteral administration can include a sterile isotonic saline solution containing between 0.1 percent and 90 percent weight per volume of the compound/bioconjugate. By way of example, a solution can contain from about 5 percent to about 20 percent, more preferably from about 5 percent to about 17 percent, more preferably from about 8 to about 14 percent, and still more preferably about 10 percent of the compound/bioconjugate. The solution or powder preparation can also include a solubilizing agent and a local anesthetic such as lignocaine to ease pain at the site of the injection. Other methods of parenteral delivery of compounds/bioconjugates will be known to the skilled artisan and are within the scope of the invention.

Oral Administration

For oral administration, a compound/bioconjugate of the invention can be formulated to take the form of tablets or capsules prepared by conventional means with one or more pharmaceutically acceptable carriers (e.g., excipients such as binding agents, fillers, lubricants and disintegrants):

A. Binding Agents

Binding agents include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof. Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., USA). An exemplary suitable binder is a mixture of microcrystalline cellulose and sodium carboxymethyl cellulose sold as AVICEL RC-581 by FMC Corporation.

B. Fillers

Fillers include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, and mixtures thereof.

C. Lubricants

Lubricants include, but are not limited to, calcium stearate, magnesium stearate, mineral oil, electromagnetic radiation mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md., USA), a coagulated aerosol of synthetic silica (marketed by Deaussa Co. of Plano, Tex., USA), CAB-O-SIL (a pyrogenic silicon dioxide product sold by Cabot Co. of Boston, Mass., USA), and mixtures thereof.

D. Disintegrants

Disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

The tablets or capsules can optionally be coated by methods well known in the art. If binders and/or fillers are used with a compound/bioconjugate of the invention, they are typically formulated as about 50 to about 99 weight percent of the compound/bioconjugate. In one aspect, about 0.5 to about 15 weight percent of disintegrant, and particularly about 1 to about 5 weight percent of disintegrant, can be used in combination with the compound. A lubricant can optionally be added, typically in an amount of less than about 1 weight percent of the compound/bioconjugate. Techniques and pharmaceutically acceptable additives for making solid oral dosage forms are described in Marshall, SOLID ORAL DOSAGE FORMS, Modern Pharmaceutics (Banker and Rhodes, Eds.), 7:359-427 (1979). Other less typical formulations are known in the art.

Liquid preparations for oral administration can take the form of solutions, syrups or suspensions. Alternatively, the liquid preparations can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations can also contain buffer salts, flavoring, coloring, perfuming and sweetening agents as appropriate. Preparations for oral administration can also be formulated to achieve controlled release of the compound/bioconjugate. Oral formulations preferably contain 10% to 95% compound/bioconjugate. In addition, a compound/bioconjugate of the present invention can be formulated for buccal administration in the form of tablets or lozenges formulated in a conventional manner. Other methods of oral delivery of compounds/bioconjugates of the invention will be known to the skilled artisan and are within the scope of the invention.

Controlled-Release Administration

Controlled-release (or sustained-release) preparations can be formulated to extend the activity of a compound/bioconjugate and reduce dosage frequency. Controlled-release preparations can also be used to effect the time of onset of action or other characteristics, such as blood levels of the compound/bioconjugate, and consequently affect the occurrence of side effects.

Controlled-release preparations can be designed to initially release an amount of a compound/bioconjugate that produces the desired therapeutic effect, and gradually and continually release other amounts of the compound/bioconjugate to maintain the level of therapeutic effect over an extended period of time. In order to maintain a near-constant level of a compound/bioconjugate in the body, the compound/bioconjugate can be released from the dosage form at a rate that will replace the amount of compound/bioconjugate being metabolized and/or excreted from the body. The controlled-release of a compound/bioconjugate can be stimulated by various inducers, e.g., change in pH, change in temperature, enzymes, water, and/or other physiological conditions or molecules.

Controlled-release systems can include, for example, an infusion pump which can be used to administer the compound/bioconjugate in a manner similar to that used for delivering insulin or chemotherapy to the body generally, or to specific organs or tumors. Typically, using such a system, the compound/bioconjugate is administered in combination with a biodegradable, biocompatible polymeric implant that releases the compound/bioconjugate over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target (e.g., organ, tissue, or group of cells), thus requiring only a fraction of a systemic dosage.

Compounds/bioconjugates of the invention can be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds/bioconjugates will be known to the skilled artisan and are within the scope of the invention.

Inhalation Administration

Compounds/bioconjugates of the invention can be administered directly to the lung of a patient/subject by inhalation. For administration by inhalation, a compound/bioconjugate can be conveniently delivered to the lung by a number of different devices. For example, a Metered Dose Inhaler ("MDI") which utilizes canisters that contain a suitable low boiling point propellant, e.g., dichlorodifluoromethane, trichlorofluoromethane, dichlorotetrafluoroethane, carbon dioxide or other suitable gas can be used to deliver a compound/bioconjugate directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a compound/bioconjugate to the lung. DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound/bioconjugate and a suitable powder base such as lactose or starch for these systems. Exemplary formulations that include compounds/bioconjugates of the present invention are described herein (the compounds/bioconjugates of the present invention are indicated in some embodiments as an "active ingredient", but those of skill in the art will recognize that pro-drugs and compound combinations are also meant to be encompassed by this term).

Another type of device that can be used to deliver a compound/bioconjugate to the lung is a liquid spray device supplied, for example, by Aradigm Corporation. Liquid spray systems use extremely small nozzle holes to aerosolize liquid compound/bioconjugate formulations that can then be directly inhaled into the lung. For example, a nebulizer device can be used to deliver a compound/bioconjugate to the lung. Nebulizers create aerosols from liquid compound/bioconjugate formulations by using, for example, ultrasonic energy to form fine particles that can be readily inhaled. Examples of nebulizers include devices supplied by Sheffield/Systemic Pulmonary Delivery Ltd., Aventis and Batelle Pulmonary Therapeutics.

In another example, an electrohydrodynamic ("EHD") aerosol device can be used to deliver a compound/bioconjugate to the lung. EHD aerosol devices use electrical energy to aerosolize liquid compound/bioconjugate solutions or suspensions. The electrochemical properties of the compound/bioconjugate formulation are important parameters to optimize when delivering this compound/bioconjugate to the lung with an EHD aerosol device. Such optimization is routinely performed by one of skill in the art. Other methods of intra-pulmonary delivery of compounds/bioconjugates will be known to the skilled artisan and are within the scope of the invention.

Liquid compound/bioconjugate formulations suitable for use with nebulizers and liquid spray devices and EHD aerosol devices will typically include the compound/bioconjugate with a pharmaceutically acceptable carrier. In one exemplary embodiment, the pharmaceutically acceptable carrier is a liquid such as alcohol, water, polyethylene glycol or a perfluorocarbon. Optionally, another material can be added to alter the aerosol properties of the solution or suspension of the compound/bioconjugate. For example, this material can be a liquid such as an alcohol, glycol, polyglycol or a fatty acid. Other methods of formulating liquid compound/bioconjugate solutions or suspensions suitable for use in aerosol devices are known to those of skill in the art.

Depot Administration

A compound/bioconjugate of the invention can be formulated as a depot preparation. Such long-acting formulations can be administered by implantation (e.g., subcutaneously or intramuscularly) or by intramuscular injection. Accordingly, the compound/bioconjugate can be formulated with suitable polymeric or hydrophobic materials such as an emulsion in an acceptable oil or ion exchange resins, or as sparingly soluble derivatives such as a sparingly soluble salt. Other methods of depot delivery of compounds/bioconjugates will be known to the skilled artisan and are within the scope of the invention.

Topical Administration

For topical application, a compound/bioconjugate can be combined with a pharmaceutically acceptable carrier so that an effective dosage is delivered, based on the desired activity ranging from an effective dosage, for example, of 1.0 μM to 1.0 mM. In one aspect of the invention, a topical formulation of a compound/bioconjugate can be applied to the skin. The pharmaceutically acceptable carrier can be in the form of, for example, and not by way of limitation, an ointment, cream, gel, paste, foam, aerosol, suppository, pad or gelled stick.

A topical formulation can include a therapeutically effective amount of a compound/bioconjugate in an ophthalmologically acceptable excipient such as buffered saline, mineral oil, vegetable oils such as corn or arachis oil, petroleum jelly, Miglyol 182, alcohol solutions, or liposomes or liposome-like products. Any of these formulations of such compounds/bioconjugates can include preservatives, antioxidants, antibiotics, immunosuppressants, and other biologically or pharmaceutically effective agents that do not exert a significant detrimental effect on the compound/bioconjugate. Other methods of topical delivery of compounds/bioconjugates will be known to the skilled artisan and are within the scope of the invention.

Rectal Administration

Compounds/bioconjugates of the invention can be formulated in rectal formulations such as suppositories or retention enemas that include conventional suppository bases such as cocoa butter or other glycerides and/or binders and/or carriers such as triglycerides, microcrystalline cellulose, gum tragacanth or gelatin. Rectal formulations can contain a compound/bioconjugate in the range of 0.5% to 10% by weight. Other methods of rectal delivery of compounds/bioconjugates will be known to the skilled artisan and are within the scope of the invention.

Other Systems of Administration

Various other delivery systems are known in the art and can be used to administer the compounds/bioconjugates of the invention. Moreover, these and other delivery systems can be combined and/or modified to promote optimization of the administration of compounds/bioconjugates of the present invention.

Kits

Various embodiments of the present invention include kits. Such kits can include a compound/bioconjugate of the present invention, optionally one or more ingredients for preparing a pharmaceutically acceptable formulation of the compound/bioconjugate, and instructions for use (e.g., administration). When supplied as a kit, different components of a compound/bioconjugate formulation can be packaged in separate containers and admixed immediately before use. Such packaging of the components separately can, if desired, be presented in a pack or dispenser device which can contain one or more unit dosage forms containing the compound/bioconjugate. The pack can, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

Kits can include reagents in separate containers such as, for example, sterile water or saline to be added to a lyophilized active component packaged separately. For example, sealed glass ampules can contain lyophilized compounds and in a separate ampule, sterile water, sterile saline or sterile each of which has been packaged under a neutral non-reacting gas, such as nitrogen. Ampules can consist of any suitable material, such as glass, organic polymers, such as polycarbonate, polystyrene, ceramic, metal or any other material typically employed to hold reagents. Other examples of suitable containers include bottles that can be fabricated from similar substances as ampules, and envelopes that can consist of foil-lined interiors, such as aluminum or an alloy. Other containers include test tubes, vials, flasks, bottles, syringes, and the like. Containers can have a sterile access port, such as a bottle having a stopper that can be pierced by a hypodermic injection needle. Other containers can have two compartments that are separated by a readily removable membrane that upon removal permits the components to mix. Removable membranes can be glass, plastic, rubber, and the like.

In certain embodiments, kits can be supplied with instructional materials. Instructions can be printed on paper or other substrate, and/or can be supplied as an electronic-readable medium, such as a floppy disc, mini-CD-ROM, CD-ROM, DVD-ROM, Zip disc, videotape, audio tape, and the like.

Detailed instructions can not be physically associated with the kit; instead, a user can be directed to an Internet web site specified by the manufacturer or distributor of the kit, or supplied as electronic mail.

Statements Regarding Incorporation by Reference and Variations

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt can result in increased or decreased solubility of that salt.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the invention, the preferred methods and materials are now described. Nothing herein is to be construed as an admission that the invention is not entitled to antedate such disclosure by virtue of prior invention.

In some embodiments, a liposome or micelle can be utilized as a carrier or vehicle for the composition.

Every formulation or combination of components described or exemplified herein can be used to practice the invention, unless otherwise stated.

The present compositions, preparations and formulations can be formulated into diagnostic compositions for enteral, parenteral, topical, aerosol, inhalation, or cutaneous administration. Topical or cutaneous delivery of the compositions, preparations and formulations can also include aerosol formulation, creams, gels, solutions, etc. The present compositions, preparations and formulations are administered in doses effective to achieve the desired diagnostic and/or therapeutic effect. Such doses can vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations can also optionally include stabilizing agents and skin penetration enhancing agents.

Methods of this invention comprise the step of administering an "effective amount" of the present diagnostic compositions, formulations and preparations containing the present compounds, to diagnosis, image, monitor, or evaluate a biological condition and/or disease state in a patient. The term "effective amount," as used herein, refers to the amount of the diagnostic formulation, that, when administered to the individual is effective to diagnose, image, monitor, or evaluate a biological condition and/or disease state. As is understood in the art, the effective amount of a given composition or formulation will depend at least in part upon the mode of administration (e.g. intravenous, oral, topical administration), any carrier or vehicle employed, and the specific individual to whom the formulation is to be administered (age, weight, condition, sex, etc.). The dosage requirements needed to achieve the "effective amount" vary with the particular formulations employed, the route of administration, and clinical objectives. Based on the results obtained in standard pharmacological test procedures, projected daily dosages of active compound can be determined as is understood in the art.

Any suitable form of administration can be employed in connection with the diagnostic formulations of the invention. The diagnostic formulations of this invention can be administered intravenously, in oral dosage forms, intraperitoneally, subcutaneously, or intramuscularly, all using dosage forms well known to those of ordinary skill in the pharmaceutical arts.

The diagnostic formulations of this invention can be administered alone, but can be administered with a pharmaceutical carrier selected upon the basis of the chosen route of administration and standard pharmaceutical practice.

The diagnostic formulations of this invention and medicaments of this invention can further comprise one or more pharmaceutically acceptable carrier, excipient, buffer, emulsifier, surfactant, electrolyte or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985).

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

REFERENCES

1. Nally, J. V. Acute renal failure in hospitalized patients. *Cleveland Clinic Journal of Medicine* 2002, 69(7), 569-574.
2. C. A. Rabito, L. S. T. Fang, and A. G. Waltman. Renal function in patients at risk with contrast material-induced acute renal failure: Noninvasive real-time monitoring. *Radiology* 1993, 186, 851-854.
3. N. L. Tilney, and J. M. Lazarus. Acute renal failure in surgical patients: Causes, clinical patterns, and care. *Surgical Clinics of North America* 1983, 63, 357-377.
4. B. E. VanZee, W. E. Hoy, and J. R. Jaenike. Renal injury associated with intravenous pyelography in non-diabetic and diabetic patients. *Annals of Internal Medicine* 1978, 89, 51-54.
5. S. Lundqvist, G. Edbom, S. Groth, U. Stendahl, and S. -O. Hietala. Iohexyl clearance for renal function measurement in gynecologic cancer patients. *Acta Radiologica* 1996, 37, 582-586.
6. P. Guesry, L. Kaufman, S. Orloff, J. A. Nelson, S. Swann, and M. Holliday. Measurement of glomerular filtration rate by fluorescent excitation of non-radioactive meglumine iothalamate. *Clinical Nephrology* 1975, 3, 134-138.
7. C. C. Baker et al. Epidemiology of Trauma Deaths. *American Journal of Surgery* 1980, 144-150.
8. R. G. Lobenhoffer et al. Treatment Results of Patients with Multiple Traumas: An Analysis of 3406 Cases Treated Between 1972 and 1991 at a German Level I Trauma Center. *Journal of Trauma* 1995, 38, 70-77.
9. J. Coalson, Pathology of Sepsis, Septic Shock, and Multiple Organ Failure. In *New Horizons: Multiple Organ Failure*, D. J. Bihari and F. B. Cerra, (Eds). Society of Critical Care Medicine, Fullerton, Calif., 1986, pp. 27-59.
10. F. B. Cerra, Multiple Organ Failure Syndrome. In *New Horizons: Multiple Organ Failure*, D. J. Bihari and F. B. Cerra, (Eds). Society of Critical Care Medicine, Fullerton, Calif., 1989, pp. 1-24.
11. R. Muller-Suur, and C. Muller-Suur. Glomerular filtration and tubular secretion of $MAG_3$ in rat kidney. *Journal of Nuclear Medicine* 1989, 30, 1986-1991.
12. P. D. Dollan, E. L. Alpen, and G. B. Theil. A clinical appraisal of the plasma concentration and endogenous clearance of creatinine. *American Journal of Medicine* 1962, 32, 65-79.
13. J. B. Henry (Ed). Clinical Diagnosis and Management by Laboratory Methods, 17th Edition, W. B. Saunders, Philadelphia, Pa., 1984.
14. F. Roch-Ramel, K. Besseghir, and H. Murer. Renal excretion and tubular transport of organic anions and cations. In *Handbook of Physiology, Section 8, Neurological Physiology, Vol. II*, E. E. Windhager, Editor, pp. 2189-2262. Oxford University Press: New York, 1992
15. D. L. Nosco and J. A. Beaty-Nosco. Chemistry of technetium radiopharmaceuticals 1: Chemistry behind the development of technetium-99m compounds to determine kidney function. *Coordination Chemistry Reviews* 1999, 184, 91-123.

16. P. L. Choyke, H. A. Austin, and J. A. Frank. Hydrated clearance of gadolinium-DTPA as a measurement of glomerular filtration rate. *Kidney International* 1992, 41, 1595-1598.

17. N. Lewis, R. Kerr, and C. Van Buren. Comparative evaluation of urographic contrast media, inulin, and $^{99m}$Tc-DTPA clearance methods for determination of glomerular filtration rate in clinical transplantation. *Transplantation* 1989, 48, 790-796.

18. W. N. Tauxe. Tubular Function. In *Nuclear Medicine in Clinical Urology and Nephrology*, W. N. Tauxe and E. V. Dubovsky, Editors, pp. 77-105, Appleton Century Crofts: East Norwalk, 1985.

19. A. R. Fritzberg et al. Mercaptoacetylglycylglycyglycine. *Journal of Nuclear Medicine* 1986, 27, 111-120.

20. G. Ekanoyan and N. W. Levin. In Clinical Practice Guidelines for Chronic Kidney Disease: Evaluation, Classification, and Stratification (K/DOQI). National Kidney Foundation: Washington, D.C. 2002, pp. 1-22.

21. Ozaki, H. et al. Sensitization of europium (III) luminescence by DTPA derivatives. *Chemistry Letters* 2000, 312-313.

22. Rabito, C. Fluorescent agents for real-time measurement of organ function. U.S. Pat. No. 2002; 6,440,389.

23. R. Rajagopalan, R. et al. Polyionic fluorescent bioconjugates as composition agents for continuous monitoring of renal function. In *Molecular Imaging: Reporters, Dyes, Markers, and Instrumentation*, A. Priezzhev, T. Asakura, and J. D. Briers, Editors, Proceedings of SPIE, 2000, 3924.

24. Dorshow, R. B. et al. Noninvasive renal function assessment by fluorescence detection. In *Biomedical Optical Spectroscopy and Diagnostics, Trends in Optics and Photonics Series* 22, E. M Sevick-Muraca, J. A. Izatt, and M. N. Ediger, Editors, pp. 54-56, Optical Society of America, Washington D.C., 1998.

25. Shirai, K. et al Synthesis and fluorescent properties of 2,5-diamino-3,6-dicyanopyrazine dyes. *Dyes and Pigments* 1998, 39(1), 49-68.

26. Kim, J. H. et al. Self-assembling of aminopyrazine fluorescent dyes and their solid state spectra. *Dyes and Pigments* 1998, 39(4), 341-357.

27. Barlin, G. B. The pyrazines. In The Chemistry of Heterocyclic Compounds. A. Weissberger and E. C. Taylor, Eds. John Wiley & Sons, New York: 1982.

28. Donald, D. S. Synthesis of 3,5-diaminopyrazinoic acid from 3,5-diamino-2,6-dicyanopyrazine and intermediates. U.S. Pat. No. 1976; 3,948,895.

29. Donald, D. S. Diaminosubstituted dicyanopyrzines and process. U.S. Pat. No. 1974; 3,814,757.

30. Muller et al. Eds, *Medical Optical Tomography, SPIE* Volume 1511, 1993.

31. R. B. Dorshow et al. Non-Invasive Fluorescence Detection of Hepatic and Renal Function, *Bull. Am. Phys. Soc.* 1997, 42, 681.

32. R. B. Dorshow et al. Monitoring Physiological Function by Detection of Exogenous Fluorescent Contrast Agents. In *Optical Diagnostics of Biological Fluids IV*, A. Priezzhevand T. Asakura, Editors, Proceedings of SPIE 1999, 3599, 2-8.

33. Stahl et al., Handbook of Pharmaceutical Salts: Properties, Selection, and Use, Wiley-VCH; Verlag Helvetica Chimica Acta, Zürich, 2002. (ISBN 3-906390-26-8)

What is claimed is:

1. A compound being of the formula (FX1):

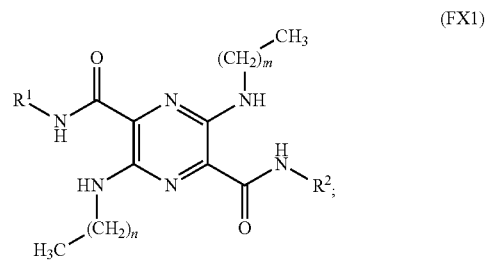

(FX1)

wherein:

each of $R^1$ and $R^2$ is $-(CH_2)_a(CH_2CH_2O)_bR^3$, $-(CH_2CH_2O)_bR^3$, $-(CH_2)_c(CH_2CH_2O)_d(CH_2)_eNR^4$ $CONR^5(CH_2)_f(CH_2CH_2O)_bR^6$, $-(CH_2)_c(CH_2CH_2O)_d$ $(CH_2)_eNR^4CSNR^5(CH_2)_f(CH_2CH_2O)_bR^6$, $-(CH_2)_c$ $(CH_2CH_2O)_d(CH_2)_eCONR^4(CH_2)_f(CH_2CH_2O)_bR^6$, $-(CH_2)_c(CH_2CH_2O)_d(CH_2)_eNR^4SO_2(CH_2)_f(CH_2$ $CH_2O)_bR^6$, $-(CH_2)_c(CH_2CH_2O)_d(CH_2)_eSO_2NR^4$ $(CH_2)_f(CH_2CH_2O)_bR^6$, $-(CH_2)_c(CH_2CH_2O)_d(CH_2)_e$ $NR^4CO(CH_2)_f(CH_2CH_2O)_bR^6$, $-(CH_2)_c(CH_2CH_2O)_d$ $(CH_2)_eNR^4CO_2(CH_2)_f(CH_2CH_2O)_bR^6$, $-(CH_2)_c$ $(CH_2CH_2O)_d(CH_2)_eOC(O)NR^4(CH_2)_f(CH_2CH_2O)_bR^6$, or $-(CH_2)_aY^1$;

each $Y^1$ is independently $-OR^3$, $-(CHOH)_cR^7$, $-NR^8R^9$, $-CONR^8R^9$, $-NHCO(CH_2)_a(CH_2CH_2O)_bR^6$ or $-NHCO(CHOH)_cR^7$;

each of $R^3$, $R^4$, $R^5$, $R^6$ and $R^7$ is independently $-H$ or $C_1$-$C_6$ alkyl;

each of $R^8$ and $R^9$ is independently $-H$, $C_1$-$C_3$ alkyl, $-(CH_2)_a(CHOH)_cR^7$ or $-(CH_2)_a(CH_2CH_2O)_bR^6$;

each of a, c, e and f is independently an integer from 0 to 10;

each b is independently an integer from 1 to 120;

each d is independently an integer from 0 to 120; and each of m and n is independently an integer from 0 to 5.

2. The compound of claim 1, wherein m is 1, 2, or 3.

3. The compound of claim 1 having formula (FX2), (FX3), (FX12), or (FX13):

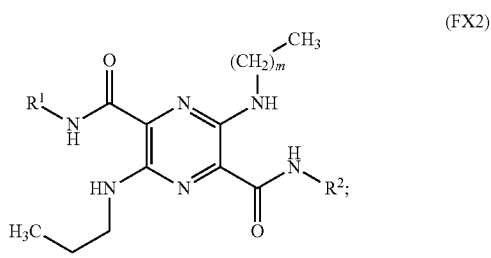

(FX2)

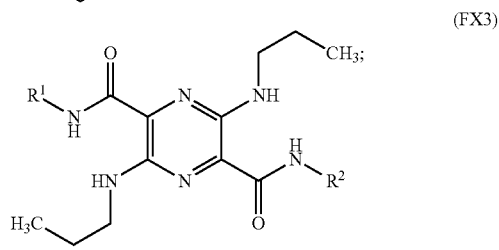

(FX3)

(FX12)
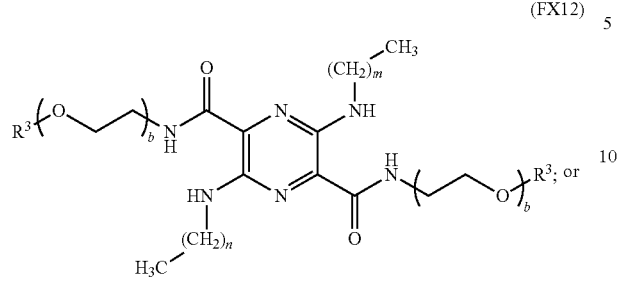
; or
(FX13)
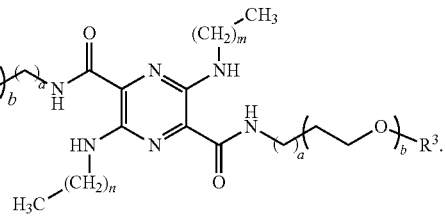
4. The compound of claim 1, having formula (FX4), (FX5), (FX6), (FX7), (FX8), (FX9), (FX10), or (FX11):
(FX4)
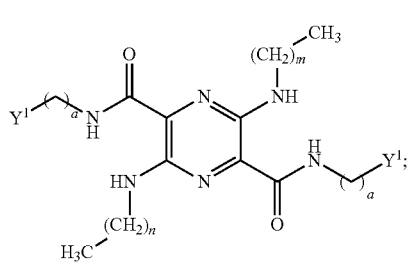
(FX5)
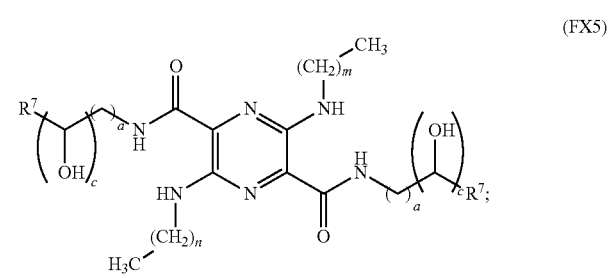
(FX6)
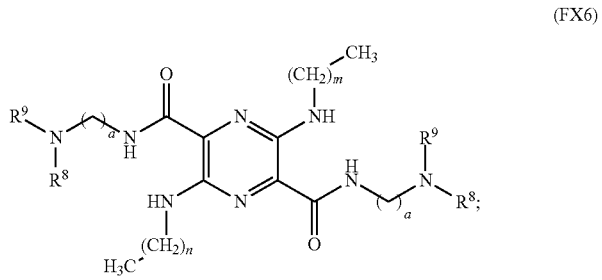
(FX7)
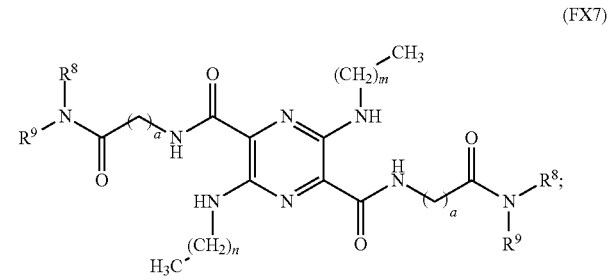
(FX8)
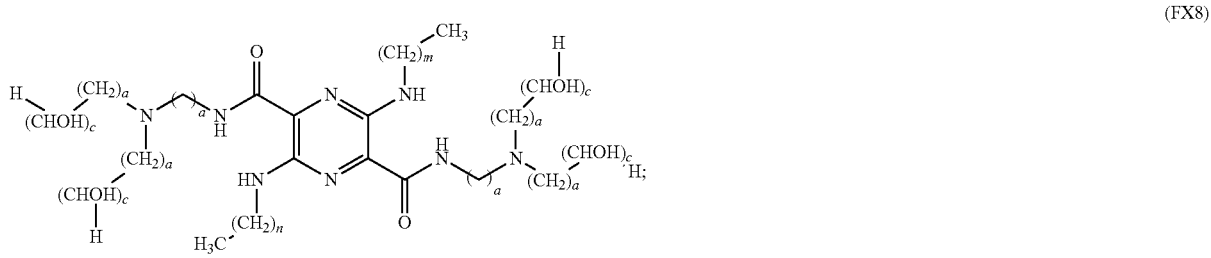

-continued
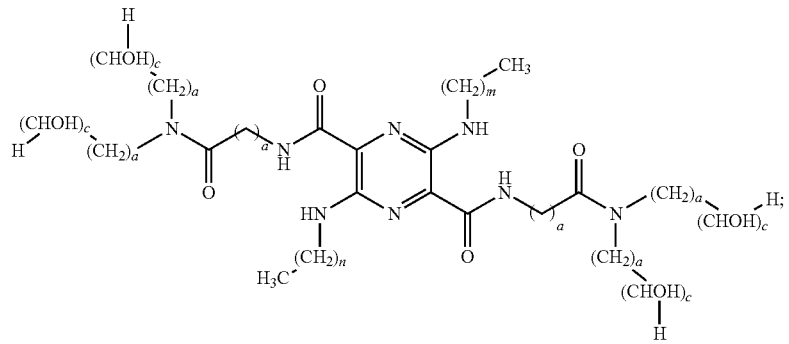
(FX9)
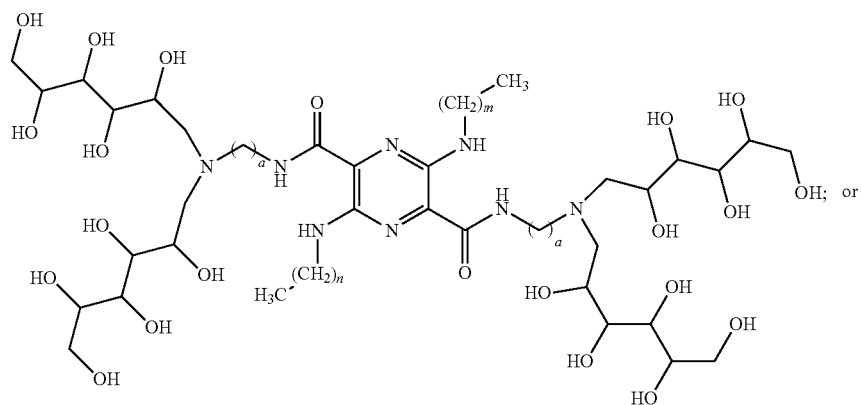
(FX10)
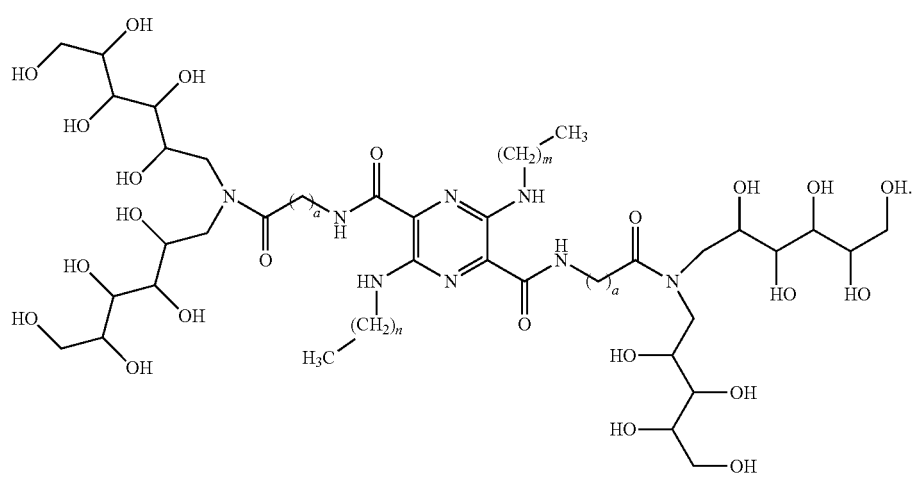
(FX11)

5. The compound of claim 1, wherein each $R^3$ is independently $C_1$-$C_3$ alkyl.

6. The compound of claim 1, wherein each $R^3$ is $C_1$ alkyl.

7. The compound of claim 1, having formula (FX14) or (FX15):

(FX14)
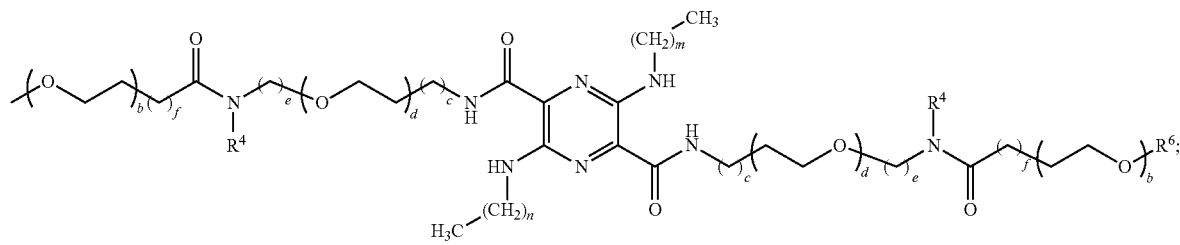

(FX15)
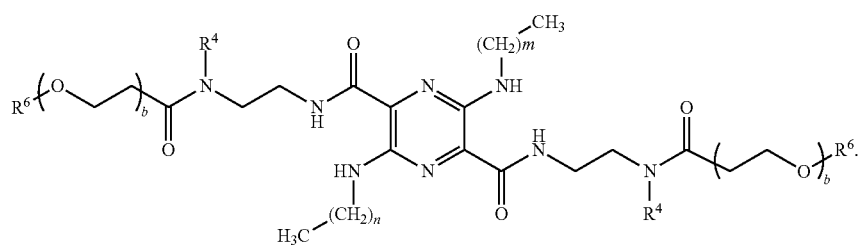

8. The compound of claim 1, wherein each $R^4$ is independently —H.

9. The compound of claim 1, wherein each $R^6$ is independently $C_1$-$C_3$ alkyl.

10. The compound of claim 1, wherein each b or d is independently an integer from 2 to 50.

11. The compound of claim 1, wherein each a, c, e or f is independently an integer from 0 to 6.

12. The compound of claim 1 having formula (FX16) or (FX17):

13. A method of using a compound of claim 1 in an optical imaging, diagnostic, visualization, monitoring, surgical, biomedical or therapeutic procedure, wherein the procedure comprises:

(i) administering a diagnostically effective amount of the compound to a subject, wherein the compound is differentially separated from a bodily fluid of the subject by an organ, tissue or system in the subject; and (ii) detecting the administered compound.

14. A method of using a compound of claim 1 in an optical imaging, diagnostic, visualization, monitoring, surgical, biomedical or therapeutic procedure, wherein the procedure comprises:

administering an effective amount of a renally excretable compound of claim 1 to a subject;

(FX16)
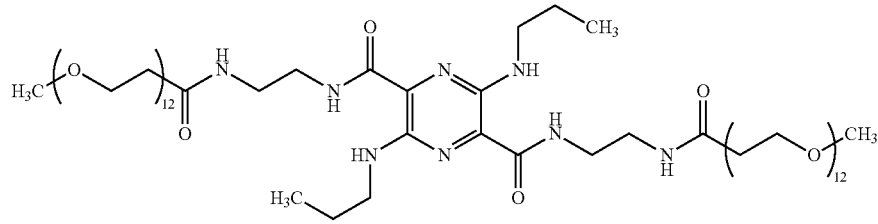

or (FX17)
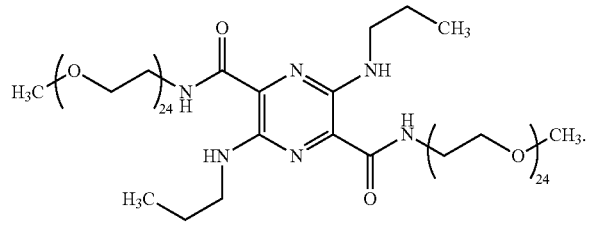

exposing a tissue of the subject's renal system having the administered compound to electromagnetic radiation, thereby generating emitted electromagnetic radiation from the compound;

detecting the emitted electromagnetic radiation from the compound, thereby visualizing or imaging at least a portion of the renal system of the subject.

15. The compound of claim 1, wherein the compound has plasma binding of less than 10%.

16. The compound of claim 1 for use in a biomedical procedure for assessing physiological function of an organ, tissue or system.

17. The compound of claim 14, wherein the at least a portion of the renal system comprises a ureter, bladder or urethra of the subject.

18. A pharmaceutical composition comprising:
the compound of claim 1; and
a pharmaceutically acceptable excipient.

19. A pharmaceutical composition comprising:
the compound of claim 1; and one or more additional therapeutic agents or diagnostic agents.

20. The method of claim 14, wherein the compound has plasma binding of less than 10%.

\* \* \* \* \*